US009441224B1

(12) United States Patent
Kim et al.

(10) Patent No.: US 9,441,224 B1
(45) Date of Patent: Sep. 13, 2016

(54) LONG NONCODING RNAS AND CELL REPROGRAMMING AND DIFFERENTIATION

(71) Applicant: CALIFORNIA INSTITUTE OF TECHNOLOGY, Pasadena, CA (US)

(72) Inventors: Daniel H. Kim, Los Angeles, CA (US); Barbara J. Wold, San Marino, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/120,786

(22) Filed: Jun. 27, 2014

Related U.S. Application Data

(60) Provisional application No. 61/840,306, filed on Jun. 27, 2013.

(51) Int. Cl.
| | | |
|---|---|---|
| C12N 15/11 | (2006.01) | |
| C12N 15/113 | (2010.01) | |
| A61K 31/713 | (2006.01) | |

(52) U.S. Cl.
CPC ............ *C12N 15/113* (2013.01); *A61K 31/713* (2013.01); *C12N 2310/14* (2013.01); *C12N 2310/18* (2013.01)

(58) Field of Classification Search
None
See application file for complete search history.

(56) References Cited

U.S. PATENT DOCUMENTS

2014/0142160 A1* 5/2014 Lee ...................... C12N 15/113
514/44 A

OTHER PUBLICATIONS

Ameres, Stefan L. et al.; "Target RNA-directed trimming and tailing of small silencing RNAs"; Science; Jun. 18, 2010; 328(5985); pp. 1534-1539.
Anders, Simon et al.; "Differential expression analysis for sequence count data"; Genome Biology 2010; 11:R106; 12pp.
Aravin, Alexei A. et al.; "A piRNA pathway primed by individual transposons is linked to de novo DNA methylation in mice"; Mol Cell.; Sep. 26, 2008; 31(6); pp. 785-799.
Aravin, Alexei A. et al.; "Developmentally Regulated piRNA Clusters Implicate MILI in Transposon Control"; Science; May 4, 2007; 316(5825); pp. 744-747.
Boyle, Elizabeth I. et al.; "GO::TermFinder—open source software for accessing Gene Ontology information and finding significantly enriched Gene Ontology terms associated with a list of genes"; Bioinformatics; Dec. 12, 2004; 20(18); pp. 3710-3715.
Buganim, Yosef et al.; "Single-cell gene expression analyses of cellular reprogramming reveal a stochastic early and hierarchic late phase"; Cell; Sep. 14, 2012; 150(6); pp. 1209-1222.
Carey, Bryce W. et al.; "A single-gene transgenic mouse strain for reprogramming adult somatic cells"; Nat Methods; Jan. 2010; 7(1); pp. 56-59.
Chang, Gang et al; "High-throughput sequencing reveals the disruption of methylation of imprinted gene in induced pluripotent stem cells"; Cell Research; 2014; 24; pp. 293-306.
De Hoon, M.J.L. et al.; "Open source clustering software"; Bioinformatics; vol. 20; No. 9; 2004; pp. 1453-1454.
Eppig, Janan T. et al.; "The Mouse Genome Database (MGD): comprehensive resource for genetics and genomics of the laboratory mouse"; Nucleic Acids Research; 2012; vol. 40; pp. D881-D886.
Guttman, Mitchell et al.; "lincRNAs act in the circuitry controlling pluripotency and differentiation"; Nature; 477(7364); pp. 295-300 (29pp.).
Hanna, Jacob et al.; "Direct cell reprogramming is a stochastic process amenable to acceleration"; Nature; Dec. 3, 2009; 462(7273); pp. 595-601.
Hayashi, Katsuhiko et al.; "Dynamic equilibrium and heterogeneity of mouse pluripotent stem cells with distinct functional and epigenetic states"; Cell Stem Cell; Oct. 9, 2008; 3(4); 21pp.
Hayashi, Katsuhiko et al.; "Resetting the epigenome beyond pluripotency in the germline"; Cell Stem Cell; 4; Jun. 5, 2009; pp. 493-498.
Johnson, David S. et al.; "Genome-Wide Mapping of in Vivo Protein-DNA Interactions"; Science; vol. 316; Jun. 8, 2007; pp. 1497-1502.
Kelley, David et al.; "Transposable elements reveal a stem cell-specific class of long noncoding RNAs"; Genome Biol.; 2012; 13(11); R107; 22pp.
Langmead, Ben et al.; "Ultrafast and memory-efficient alignment of short DNA sequences to the human genome"; Genome Biology; Mar. 4, 2009; 10:R25; 10pp.
Leitch, Harry G. et al.; "The mammalian germline as a pluripotency cycle"; Development 140; 2013; pp. 2495-2501.
Li, Xin Zhiguo et al.; "An ancient transcription factor initiates the burst of piRNA production during early meiosis in mouse testes"; Molecular Cell; Apr. 11, 2013; 50(1); pp. 67-81.
Luteijn, Maartje J. et al.; "PIWI-interacting RNAs: from generation to transgenerational epigenetics"; Nature Reviews; Genetics; vol. 14; Aug. 2013; pp. 523-534.
Magnusdottir, Erna et al.; "A tripartite transcription factor network regulates primordial germ cell specification in mice"; Nat Cell Biol.; Aug. 2013; 15(8); pp. 905-915.
Marchetto, Maria C.N. et al.; "Differential LINE-1 regulation in pluripotent stem cells of humans and other great apes"; Nature; Nov. 28, 2013; 503(7477); pp. 525-529.
Marson, Alexander et al.; "Connecting microRNA genes to the core transcriptional regulatory circuitry of embryonic stem cells"; Cell; Aug. 8, 2008; 134(3); pp. 521-533.
Mortazavi, Ali et al.; "Mapping and quantifying mammalian transcriptomes by RNA-Seq"; Nature Methods; vol. 5; No. 7; Jul. 2008; pp. 621-628.

(Continued)

*Primary Examiner* — Kate Poliakova-Georgantas
(74) *Attorney, Agent, or Firm* — Lewis Roca Rothgerber Christie LLC

(57) ABSTRACT

Long noncoding RNAs (lncRNAs) are identified that enhance pluripotency reprogramming of somatic cells as well as differentiation of pluripotent cells. Induced pluripotent stem (iPS) cell generation from somatic cells leads to the upregulation and downregulation of identified lncRNAs. The modulation of these lncRNAs are capable of enhancing pluripotency of somatic cells as well as enhancing differentiation of a pluripotent cell.

8 Claims, 55 Drawing Sheets

(56) References Cited

OTHER PUBLICATIONS

Ohinata, Yasuhide et al.; "Blimp1 is a critical determinant of the germ cell lineage in mice"; Nature; vol. 436; Jul. 14, 2005; pp. 207-213.

Raj, Arjun et al.; "Imaging individual mRNA molecules using multiple singly labeled probes"; Nat Methods; Oct. 2008; 5(10); pp. 877-879.

Ramskold, Daniel et al.; "Full-length mRNA-Seq from single-cell levels of RNA and individual circulating tumor cells"; Nat Biotechnol.; Aug. 2012; 30(8); pp. 777-782.

Roberts, Adam et al.; "Streaming fragment assignment for real-time analysis of sequencing experiments"; Nat Methods; Jan. 2013; 10(1); 14pp.

Saitou, Mitinori et al.; "A molecular programme for the specification of germ cell fate in mice"; Nature; vol. 418; Jul. 18, 2002; pp. 293-300.

Saldanha, Alok J.; "Java Treeview—extensible visualization of microarray data"; Bioinformatics; vol. 20; No. 17; 2004; pp. 3246-3248.

Silva, Jose et al.; "Promotion of reprogramming to ground state pluripotency by signal inhibition"; PLoS Biology; Oct. 2008; vol. 6; Issue 10; e253; pp. 2237-2247.

Tam, Oliver H. et al.; "Pseudogene-derived small interfering RNAs regulate gene expression in mouse oocytes"; Nature; May 22, 2008; 453(7194); pp. 534-538.

Trapnell, Cole et al.; "TopHat: discovering splice junctions with RNA-Seq"; Bioinformatics; vol. 25; No. 9; 2009; pp. 1105-1111.

Trapnell, Cole et al.; "Transcript assembly and abundance estimation from RNA-Seq reveals thousands of new transcripts and switching among isoforms"; Nat Biotechnol.; May 2010; 28(5); pp. 511-515.

Zhao, Jing et al.; "Genome-wide identification of polycomb-associated RNAs by RIP-seq"; Mol Cell; Dec. 22, 2010; 40(6); pp. 939-953.

\* cited by examiner

FIG.4B

| # | Name | # | Name | # | Name |
|---|---|---|---|---|---|
| 1 | Dut | 48 | 1500009L16Rik | 95 | Ipo11 |
| 2 | Gm17386 | 49 | Abhd4 | 96 | Gm5921 |
| 3 | Dppa3 (Stella) | 50 | P2rx4 | 97 | Tmsb15b2 |
| 4 | Unc13d | 51 | Tmsb15b1 | 98 | 0610037L13Rik |
| 5 | Gm17312 | 52 | Fbxo6 | 99 | Fabp5 |
| 6 | Gm10491 | 53 | Ppm1e | 100 | Yif1a |
| 7 | Tmem55b | 54 | Rabac1 | | |
| 8 | Calcoco2 | 55 | Gm10291 | | |
| 9 | Prps1 | 56 | Mfsd10 | | |
| 10 | Ufm1 | 57 | Gltp | | |
| 11 | Lsm3 | 58 | Nrbp1 | | |
| 12 | Gm17635 | 59 | Rpl21-ps6 | | |
| 13 | Lztr1 | 60 | Abhd5 | | |
| 14 | Gm17404 | 61 | Timeless | | |
| 15 | Gm10139 | 62 | Raly | | |
| 16 | Gm9396 | 63 | Plekha3 | | |
| 17 | Hspa14 | 64 | Glrx | | |
| 18 | Snx22 | 65 | Mrps10 | | |
| 19 | Spic | 66 | Psmd14 | | |
| 20 | Zfp125 | 67 | C730034F03Rik | | |
| 21 | Gm10772 | 68 | Gltscr2 | | |
| 22 | Gm3272 | 69 | Ubac1 | | |
| 23 | H2afx | 70 | Gm2606 | | |
| 24 | Gm2574 | 71 | 4930402H24Rik | | |
| 25 | Gm5138 | 72 | 1500010J02Rik | | |
| 26 | Chpt1 | 73 | Glb1 | | |
| 27 | Gm10982 | 74 | Gm8225 | | |
| 28 | Gm10358 | 75 | Qk | | |
| 29 | Gm16512 | 76 | Madd | | |
| 30 | Fbxo15 | 77 | Nudt2 | | |
| 31 | Gm17449 | 78 | Mfge8 | | |
| 32 | Gm10481 | 79 | Ube2c | | |
| 33 | Gm11092 | 80 | Gm11032 | | |
| 34 | D330041H03Rik | 81 | Nfyc | | |
| 35 | Sgpl1 | 82 | Eya3 | | |
| 36 | Rtcd1 | 83 | Uck2 | | |
| 37 | Pbld1 | 84 | Cinp | | |
| 38 | C130073F10Rik | 85 | Mettl3 | | |
| 39 | Snf8 | 86 | Prdm9 | | |
| 40 | 5730507C01Rik | 87 | Gm17555 | | |
| 41 | Gm17353 | 88 | 8030474K03Rik | | |
| 42 | Cd59b | 89 | Dom3z | | |
| 43 | 5430437P03Rik | 90 | Aspscr1 | | |
| 44 | Rpl29 | 91 | Add1 | | |
| 45 | Cib1 | 92 | Wfdc2 | | |
| 46 | Tmem70 | 93 | Flot1 | | |
| 47 | Supt16h | 94 | Cxcr2 | | |

FIG. 7B

| GO term | Cluster freq. | Genome freq. | P-value corrected | FDR | False positive | Annotated genes |
|---|---|---|---|---|---|---|
| developmental process | 95 of 356 genes, 26.7% | 3888 of 32859 genes, 11.8% | 1.63e-11 | 0.00% | 0.00 | G6pdx, Unc5b, Angp, Myo7a, Casp6, Nedd4, Ext1, Hsd11b1, Aspa, Prdm1, Selenbp1, Maf, Gm13305, Asl, Tnfsf4, Lcsk1, Cd1d1, Gja1, Mfn2, Bpgm, Elna, Tdf1, Pgp3rl, Spin1, Twist2, Agba3, Dclk1, Nfic, Pik1a, Stat1, Epha7, Ant, Gna12, Luzp1, Pesin, Luf, DOH48114, Cdc42ep5, Olfm1, Dand5, Elat, Serpinf1, Lefat1, Fam82c2, Adigap24, Il1ral, Zeb1, Tmem204, Keap1, Tgfbr3, Bmp1, Col1a1, Endo3b, Snpc2, Zfp422, Tec2, Shroom2, Jara, AI597479, Casp1, Clcf1, Mgat1, Tnc, Plag1, Mcst1, Jam3, Man2, Mfn214, Clmn1, Usp1, Hoxb9, Angpt2, Mmp2, Prkra, Fam3c, Cub, Mfge8, Zfp37, Tgfb1l1, Lpar1, Snai2, Abhd5, Sdf4, Col8a1, Trim16, Thbs2, Ahi1, Inpp5b, Gapd1, Cebpg, Nr4a2, Acvr1, Rgph9, Fuz, Olfm3 |

FIG. 7B Cont.

| GO term | Cluster freq. | Genome freq. | P-value corrected | FDR | False positive | Annotated genes |
|---|---|---|---|---|---|---|
| metabolic process | 172 of 372 genes 46.2% | 9274 of 32859 genes, 28.2% | 1.40e-10 | 0.00% | 0.00 | Arhgef1, Mettl8, Zfp14, Kitl, Zfp186, Rad11, H1f0, Palm, Ephl, Ehd1l, Actr1a, Pck, Tgfb2, Dync1, Pde8a, Tspo, Trex, Adssl1, Med16, Nme1, Ss3ga6, Bgh, Ctc, PacT1, Klk1b21, Ugt1a6a, Tecpr1, Junb, Rgnef, Gsta1, Irf1, Anxa3, Ampd4, Crym, Ogt2, Epas1, 1810031K17Rik, Gsrm4, Mettl13, Hmgn5, Lrtlp1, Mapkap1, 2810002N01Rik, Net1, Prm2, Tcf7l2, Tmm12, Pla2g16, Edem3, Tmem188, Crebl, Hsd3b7, Clst, Abat, Fosg1, Sprk, Prs, Egd5, Ubn4, Pkig, Oaz3-ps, Lrlm1, 2010106G01Rik, Gstnl, Ya1, Men1, Ogfod2, Mysl1, Nt5c3, Pckrir, 4932438A13Rik, Clns, Mocos, Dpagt1, Pcyt1a, Hdhd2, Atp11b3, Cct1, Add1, Lange, Ncoa3, Ghr, Srebf1, Mboat2, Cnnt, Akat1, At12, Klf6, 5830428H23Rik, Mgl, Slc27a1, Pcdh, Ascc2, Mara, Gtf2i, Nr3c1, Bach, Klk1b24, Cryz, Nhn, Gsti3, Fabp5, Adam17, Dix3l2, Tufnip5, Cd55, Rare, Timagl1, Nmmat2, Amfr, Nudc2, Cogalnact2, Cast, Mtmh1, Bmlc7, Hcstd1, Itng5k, BC026590, Adam15, Cpeh1, Cd34, Lck, Cast, Lig3, Mef2a, Pik1p1, H2-Ke6, Tuk64, Col5a1, Sacs5, Rrase1, Mrl1, Hoxb13, Psc23, Hes, Mnd4, Rab27a, Rnre, Mcpee, Shikhp1, Mast2, Pape1, Rdh10, Klk15, Aldh1a1, Mice, Myh10, Mos81, Cd109, Ptprv, P2rx4, Acads, Ikbkg, Hk1, Aca5, Eif4g3, Ophn1, Nudt6, Pla2e2, Hadhb, Cn43D, Rpt4, Abcn5, Bse, Mgll, Egsr, Bcs5, Sh3rf1, Caga4, Ecc2, Scbp2, Ilrap |

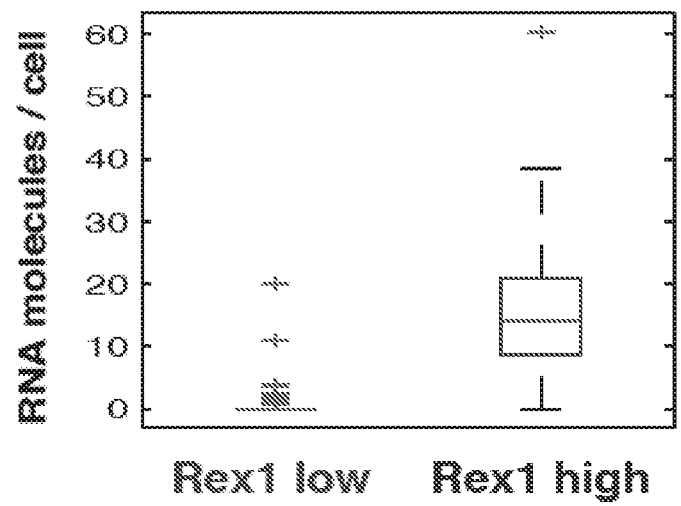
FIG. 10C  Blimp1
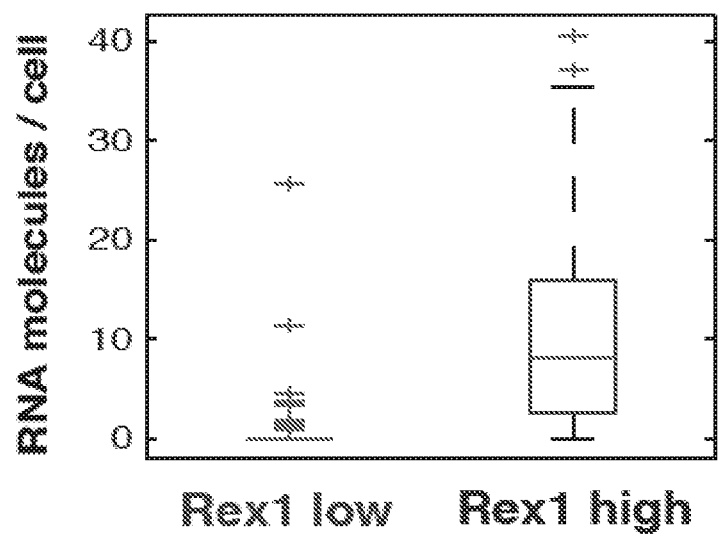
FIG. 10D  Prdm14

(Wk6)

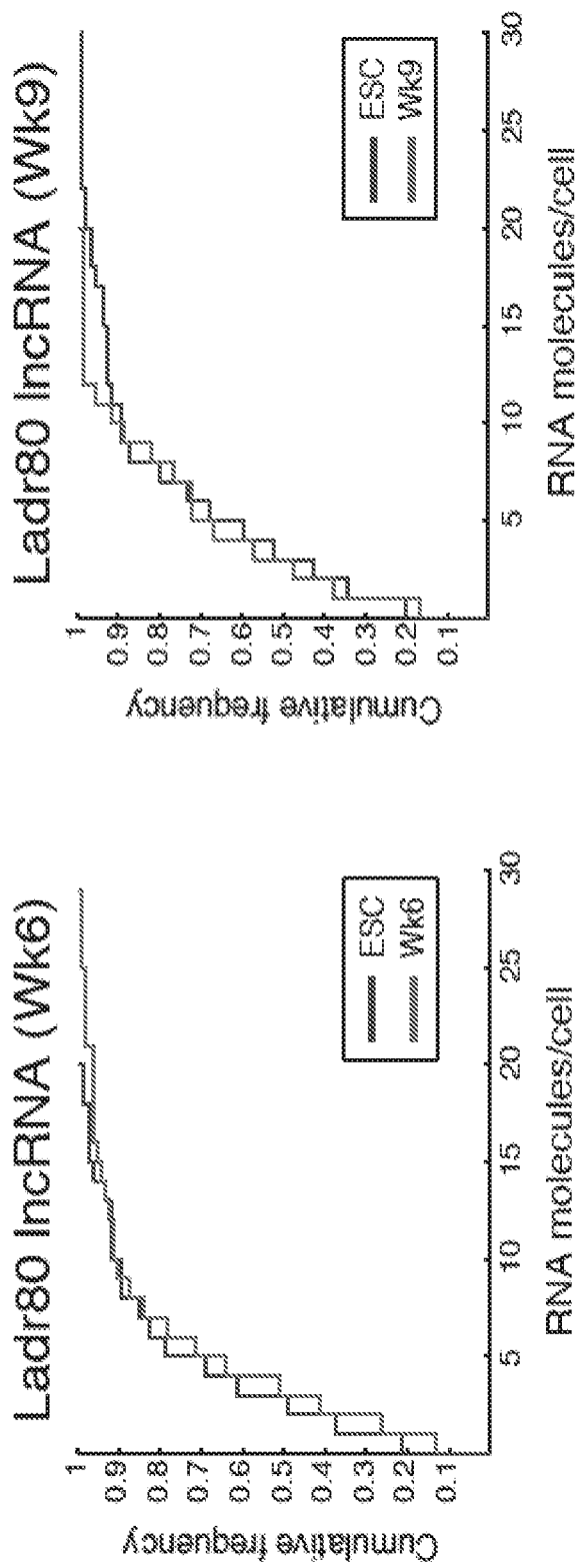

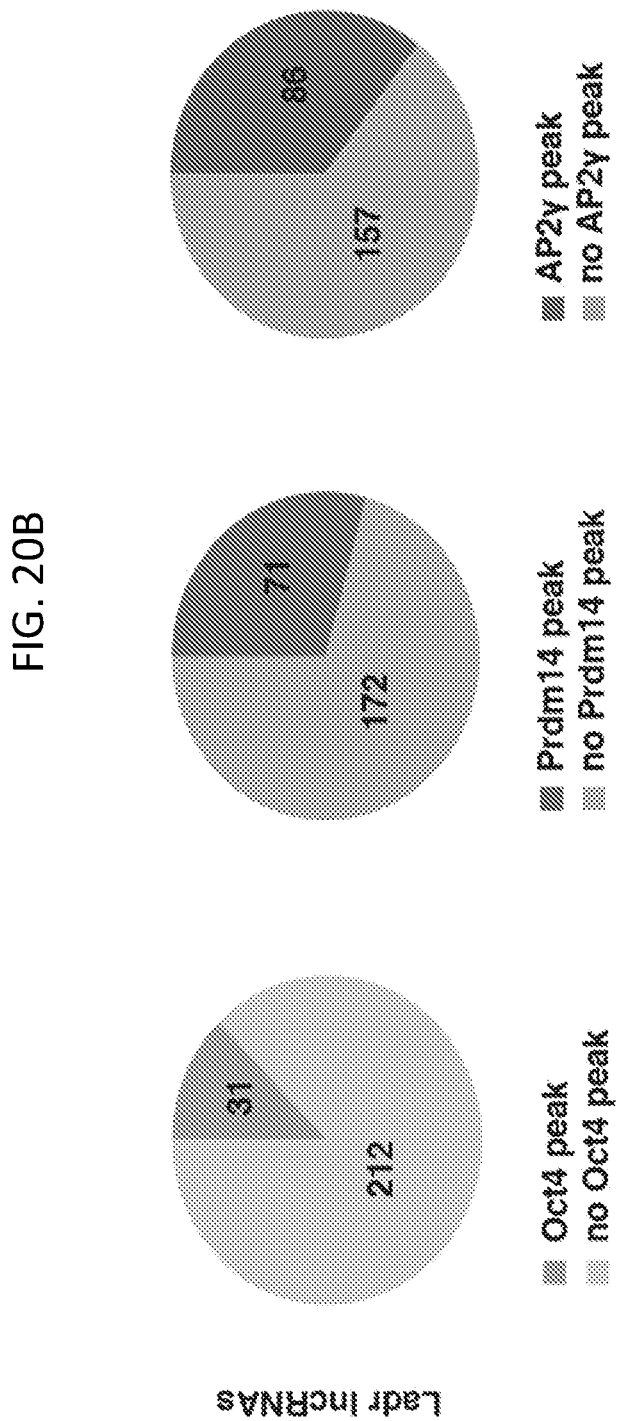

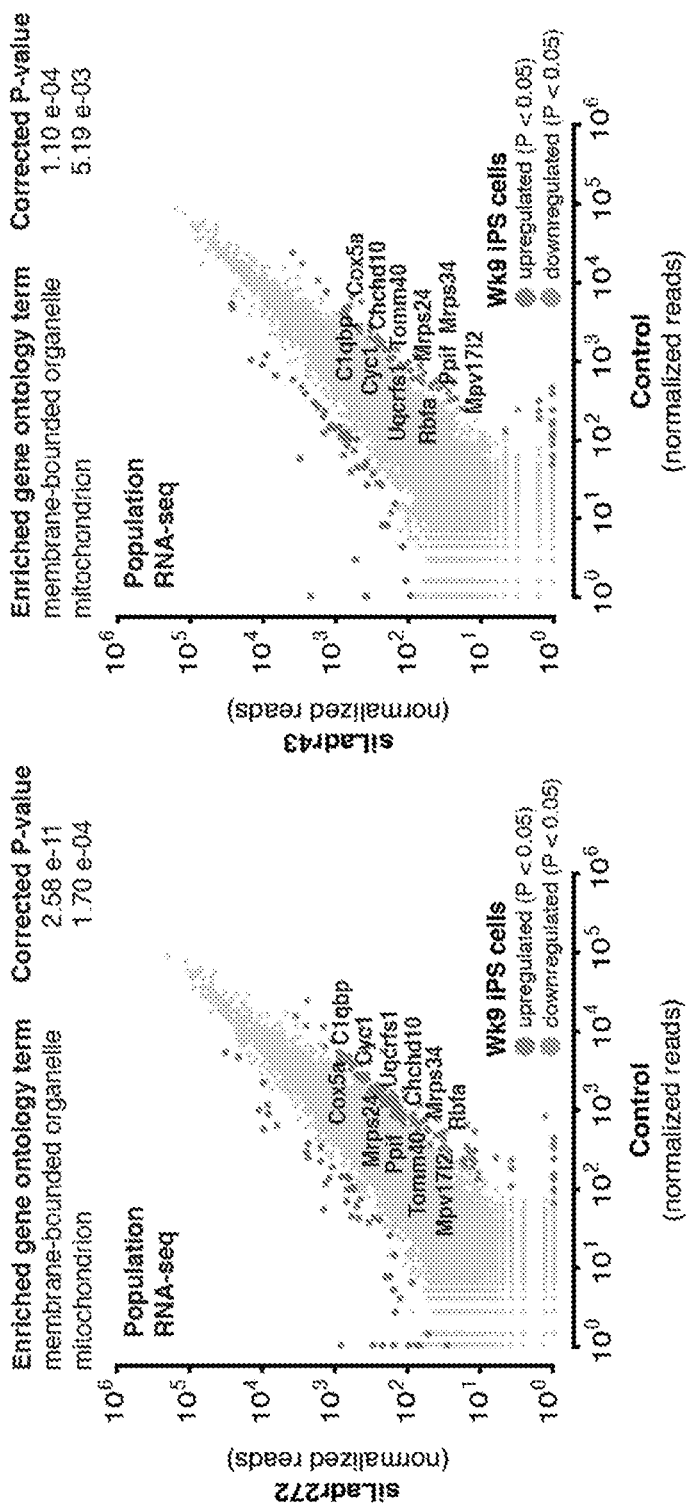

LONG NONCODING RNAS AND CELL REPROGRAMMING AND DIFFERENTIATION

CROSS-REFERENCE TO RELATED APPLICATION(S)

The present application claims priority to and the benefit of U.S. Provisional Application Ser. No. 61/840,306 filed on Jun. 27, 2013, the entire contents of which are incorporated herein by reference.

STATEMENT REGARDING FEDERALLY SPONSORED RESEARCH OR DEVELOPMENT

This invention was made with government support under HG006998 awarded by the National Institutes of Health. The government has certain rights in the invention."

SEQUENCE LISTING

The instant application contains a Sequence Listing which has been submitted electronically in ASCII format and is hereby incorporated by reference in its entirety. Said ASCII copy, created on Nov. 17, 2014, is named 75207-C766_SL.txt and is 19,013,879 bytes in size.

BACKGROUND

The most well-known type of pluripotent stem cell is the embryonic stem (ES) cell. However, the generation of embryonic stem cells can only be derived from embryos, and it has so far not been feasible to create patient-matched embryonic stem cell lines. Induced pluripotent stem (iPS) cells are a type of pluripotent stem cell that can be generated directly from somatic (differentiated) cells. Since iPS cells can be derived directly from adult tissues, they not only bypass the need for embryos, but can be made in a patient-matched manner, which means that each individual could have their own pluripotent stem cell line. iPS cells may be generated through the ectopic expression of Oct 4, Sox2, Lkf4, and c-Myc (OSKM) transcription factors in somatic cells (Takahashi and Yamanaka, 2006), leading to global epigenetic changes during reprogramming (Papp and Plath, 2013). Chromatin regulatory proteins mediate epigenetic remodeling during iPS cell formation, and loss-of-function studies have shown that Polycomb proteins are potent regulators of cell fate reprogramming (Onder et al., 2012). However, iPS cells may retain epigenetic signatures of their somatic cell of origin (Kim et al., 2010; Polo et al., 2010) that can persist through extended passaging (Kim et al., 2011), and the molecular mechanisms responsible for epigenetic memory are unclear.

In ES cells, long noncoding RNAs (lncRNAs) associate with chromatin regulators such as Polycomb proteins (Guttman et al., 2011; Zhao et al., 2010; Zhao et al., 2008) and are required to repress lineage-specific genes in the pluripotent state (Guttman et al., 2011). LncRNAs have been shown to target chromatin regulatory complexes throughout the genome in various developmental settings (Lee and Bartolomei, 2013; Rinn and Chang, 2012), but relatively little is known about lncRNAs in the context of cellular reprogramming.

SUMMARY

Some embodiments of the present invention are directed to a method of enhancing reprogramming of a somatic cell to a pluripotent cell in a human or mouse, the method including upregulation of at least one long noncoding RNA (lncRNA) selected from SEQ ID NOs. 1-347 and 368-408 and isoforms, fragments, and homologs thereof in the somatic cell.

In some embodiments, the method of enhancing reprogramming of a somatic cell also includes downregulating at least one lncRNA selected from SEQ ID NOs. 348-367 and 415-424 and SEQ ID NOs. 408-414 and isoforms, fragments, and homologs thereof.

Some embodiments of the present invention are directed to a method of enhancing differentiation of a pluripotent cell in a human or mouse, the method including downregulation of at least one long noncoding RNA (lncRNA) selected from SEQ ID NOs. 1-347 and 368-407 and isoforms, fragments and homologs thereof in the pluripotent cell.

In some embodiments, the method of enhancing differentiation of a pluripotent cell also includes upregulating at least one lncRNA selected from SEQ ID NOs. 348-367 and 415-424 and SEQ ID NOs. 408-414 and isoforms, fragments, and homologs thereof.

Some embodiments of the present invention include a composition for enhancing pluripotency reprogramming in a human or mouse somatic cell, the composition includes an inhibiting nucleic acid directed against a long noncoding RNA (lncRNA) selected from SEQ ID NOs. 358-367 and SEQ ID NOs. 408-414 and isoforms, fragments, and homologs thereof.

Some embodiments of the present invention include a composition for enhancing pluripotency reprogramming in a human or mouse somatic cell, the composition includes a vector, synthetic nucleic acid or in vitro transcribed nucleic acid encoding a long noncoding RNA (lncRNA) selected from SEQ ID NOs. 1-347 and 368-407 and isoforms, fragments, and homologs thereof.

BRIEF DESCRIPTION OF THE DRAWINGS

These and other features and advantages of the present invention will be better understood by reference to the following detailed description when considered in conjunction with the accompanying drawings.

FIG. 4B lists 100 induced proteins as described herein.

FIG. 7B is a table summarizing the tail tip fibroblast (TTFs) analysis of FIG. 7A, as described herein, in which GO (gene ontology) the annotated genes as well as the Cluster frequency, Genome frequency, Corrected P-value, FDR, and False positive values are shown as indicated.

FIGS. 10A-10D show a histogram (FIG. 10A) and box plots (FIGS. 10B, 10C, 10D) of RNA molecules per cell for each indicated gene, as determined by 4-color smFISH showing that cells expressing higher levels of Rex1, also expressed Stella, Prdm14, and Blimp1, while cells with low Rex1 expression generally did not express these genes, as described herein.

FIGS. 14B and 14C are graphs of cumulative frequency of Ladr80 lncRNAs at week 6 (Wk6) (FIG. 14B) and week 9 (Wk9) (FIG. 14C) compared with ESC (embryonic stem cells), as described herein.

FIG. 20B shows graphs indicating the fraction of Oct4, Prdm14, or Ap2γ binding sites within lncRNA promoters out of the total number of Ladr lncRNAs, as described herein.

FIG. 22A is a graph showing differential expression analysis of upregulated or downregulated genes, as indicated, in week 9 (Wk 9) iPS cells in the presence (siLadr272) or absence (control) of Ladr272 siRNA, as described herein.

FIG. 22B is a graph showing differential expression analysis of upregulated or downregulated genes, as indicated, in week 9 (Wk 9) iPS cells in the presence (siLadr43) or absence (control) of Ladr43 siRNA, as described herein.

DETAILED DESCRIPTION

Figure 1:
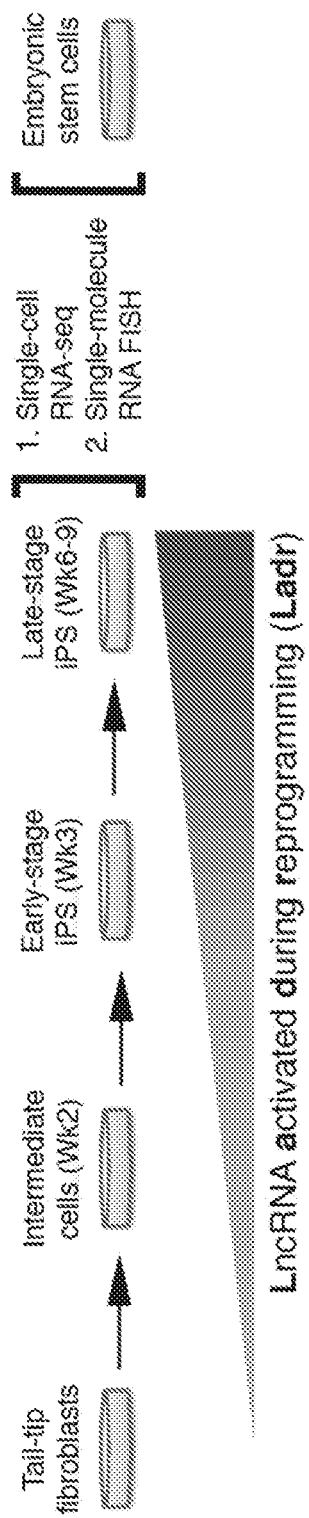
FIG. 1 is a schematic showing induction of pluripotency in somatic cells, according to embodiments of the invention.

Some embodiments of the present invention include at least one long noncoding RNA (lncRNA) that regulates the induction of pluripotency in somatic cells. As disclosed herein, the lncRNAs in Tables 1 and 2 increase effective pluripotency of iPS cells. Some embodiments of the present invention include methods for improved induction of pluripotency in somatic cells. These methods for inducing pluripotency in somatic cells include the presence of (activation of) and/or absence (repression of) at least one of the long lncRNAs disclosed in Tables 1 and/or 2. Induction of pluripotency in tail-tip fibroblasts from an OSKM mouse to produce iPS cells for comparative expression analysis with embryonic stem (ES) cells is shown schematically in FIG. 1.

As used herein, "reprogramming" in the context of a somatic cell refers to the erasure and remodeling of the differentiated somatic cell to a pluripotent embryonic state, Conversely, "reprogramming" in the context of a pluripotent cell is also referred to as differentiation, and refers to the remodeling of the pluripotent cell to a more specialized differentiated cell.

As used herein, "induction of pluripotency" and "pluripotency reprogramming" refers to the induction of pluripotency by induction of Oct4, Sox2, Klf4, c-Myc (OSKM) transcription factors and/or the "dual inhibition" of Mek and Gsk3 also known as "2i."

In some embodiments, methods for improved induction of pluripotency in somatic cells includes the presence of the lncRNAs disclosed herein to be activated during reprogramming of the somatic cells. These lncRNAs activated during reprogramming are also referred to herein as Ladrs. Induction of pluripotency activated mouse Ladrs 1-314 (SEQ ID NOs. 1-314) are listed in Table 1 and the orthologous human lncRNA (SEQ ID NOs. 315-347) identified by Liftover analysis, are listed in Table 2.

TABLE 1

| SEQ ID NO: | lncRNA | Gene name | chr | left | right | Str* | ID |
|---|---|---|---|---|---|---|---|
| 1 | Ladr 1 | Gm17586 | chr11 | 120495082 | 120496439 | + | ENSMUSG00000090998 |
| 2 | Ladr 2 | 4930444M15Rik | chr14 | 76914365 | 76920662 | − | ENSMUSG00000085974 |
| 3 | Ladr 3 | 1810019D21Rik | chr8 | 108659300 | 108662425 | + | ENSMUSG00000086390 |
| 4 | Ladr 4 | B230208H11Rik | chr10 | 12636446 | 12642898 | − | ENSMUSG00000085233 |
| 5 | Ladr 5 | Gm15728 | chr5 | 117839148 | 117843507 | + | ENSMUSG00000086075 |
| 6 | Ladr 6 | Gm2529 | chr8 | 87189027 | 87193305 | + | ENSMUSG00000073822 |
| 7 | Ladr 7 | 2700086A05Rik | chr6 | 52125216 | 52165075 | + | ENSMUSG00000085696 |
| 8 | Ladr 8 | C430039J16Rik | chr13 | 98053137 | 98055889 | + | ENSMUSG00000091451 |
| 9 | Ladr 9 | Gm17291 | chr10 | 62755034 | 62758541 | − | ENSMUSG00000050249 |
| 10 | Ladr 10 | A330048O09Rik | chr13 | 48367785 | 48369253 | − | ENSMUSG00000087671 |
| 11 | Ladr 11 | Gm17698 | chr1 | 165231921 | 165233751 | − | ENSMUSG00000090335 |
| 12 | Ladr 12 | 4930481B07Rik | chr3 | 94819547 | 94824060 | + | ENSMUSG00000085956 |
| 13 | Ladr 13 | A730011C13Rik | chr3 | 94798332 | 94801272 | − | ENSMUSG00000084846 |
| 14 | Ladr 14 | 4930526L06Rik | chr19 | 11271307 | 11374376 | + | ENSMUSG00000085490 |
| 15 | Ladr 15 | Gm15787 | chr5 | 110583419 | 110605523 | − | ENSMUSG00000086247 |
| 16 | Ladr 16 | 2310043M15Rik | chr16 | 93792395 | 93795133 | − | ENSMUSG00000091302 |
| 17 | Ladr 17 | 4930566F21Rik | chr5 | 31789002 | 31797552 | − | ENSMUSG00000086967 |
| 18 | Ladr 18 | Meg3 | chr12 | 110779211 | 110809936 | + | ENSMUSG00000021268 |
| 19 | Ladr 19 | 3110056K07Rik | chr12 | 72092602 | 72116819 | − | ENSMUSG00000085622 |
| 20 | Ladr 20 | Gm15441 | chr3 | 96359688 | 95370724 | − | ENSMUSG00000074398 |
| 21 | Ladr 21 | Rian | chr12 | 110842155 | 110899919 | + | ENSMUSG00000091793 |
| 22 | Ladr 22 | 9830144P21Rik | chr2 | 129031694 | 129056315 | − | ENSMUSG00000087528 |
| 23 | Ladr 23 | 4930513N10Rik | chr8 | 98330730 | 98345628 | + | ENSMUSG00000074136 |
| 24 | Ladr 24 | 4930404I05Rik | chr16 | 91011494 | 91016988 | + | ENSMUSG00000087354 |
| 25 | Ladr 25 | GM17250 | chr2 | 71586132 | 71588219 | − | ENSMUSG00000090953 |
| 26 | Ladr 26 | Gm16641 | chr11 | 50050511 | 50102341 | + | ENSMUSG00000085364 |
| 27 | Ladr 27 | 2310010G23Rik | chrX | 34354766 | 34357180 | − | ENSMUSG00000090647 |
| 28 | Ladr 28 | 2810442I21Rik | chr11 | 16835157 | 16851285 | − | ENSMUSG00000087060 |
| 29 | Ladr 29 | 9230114K14Rik | chr5 | 52581920 | 52589223 | + | ENSMUSG00000087676 |
| 30 | Ladr 30 | Vax2os1 | chr6 | 83642800 | 83662195 | − | ENSMUSG00000085794 |
| 31 | Ladr 31 | 1700007L15Rik | chr16 | 33379941 | 33380813 | − | ENSMUSG00000090918 |

TABLE 1-continued

| SEQ ID NO: | lncRNA | Gene name | chr | left | right | Str* | ID |
|---|---|---|---|---|---|---|---|
| 32 | Ladr 32 | 4632427E13Rik | chr7 | 99886168 | 99889978 | − | ENSMUSG00000074024 |
| 33 | Ladr 33 | Gm17491 | chr8 | 23590763 | 23593802 | + | ENSMUSG00000078859 |
| 34 | Ladr 34 | 4930461G14Rik | chr9 | 58302980 | 58317430 | + | ENSMUSG00000086516 |
| 35 | Ladr 35 | Gm16957 | chr17 | 17526907 | 17532267 | − | ENSMUSG00000087696 |
| 36 | Ladr 36 | 2410003L11Rik | chr11 | 97459825 | 97484207 | + | ENSMUSG00000085806 |
| 37 | Ladr 37 | 4930500J02Rik | chr2 | 104399320 | 104411586 | + | ENSMUSG00000086454 |
| 38 | Ladr 38 | Gm17335 | chr11 | 22500338 | 22510882 | − | ENSMUSG00000090797 |
| 39 | Ladr 39 | Gm13110 | chr4 | 154019863 | 154029427 | − | ENSMUSG00000086810 |
| 40 | Ladr 40 | 9530027I09Rik | chrX | 45629969 | 45638603 | − | ENSMUSG00000085283 |
| 41 | Ladr 41 | 2500002B13Rik | chr8 | 59966851 | 59987674 | + | ENSMUSG00000086276 |
| 42 | Ladr 42 | 4933404O12Rik | chr5 | 137395016 | 137412982 | + | ENSMUSG00000085062 |
| 43 | Ladr 43 | Gm2694 | chr8 | 89996711 | 90049453 | + | ENSMUSG00000087391 |
| 44 | Ladr 44 | A230072C01Rik | chrX | 20538810 | 20563863 | + | ENSMUSG00000086877 |
| 45 | Ladr 45 | C330046G13Rik | chr10 | 84010162 | 84016083 | − | ENSMUSG00000085671 |
| 46 | Ladr 46 | Gm17300 | chr4 | 131907687 | 131909297 | + | ENSMUSG00000091021 |
| 47 | Ladr 47 | Xist | chrX | 100655714 | 100678556 | − | ENSMUSG00000086503 |
| 48 | Ladr 48 | 4930558J18Rik | chr1 | 57416066 | 57434348 | − | ENSMUSG00000084958 |
| 49 | Ladr 49 | Gm10143 | chr19 | 10272858 | 10276874 | + | ENSMUSG00000064032 |
| 50 | Ladr 50 | 1110002J07Rik | chr10 | 66375237 | 66383006 | − | ENSMUSG00000087275 |
| 51 | Ladr 51 | 1700086O06Rik | chr18 | 38398059 | 38410219 | − | ENSMUSG00000086988 |
| 52 | Ladr 52 | 6720401G13Rik | chrX | 47908921 | 47988498 | − | ENSMUSG00000085396 |
| 53 | Ladr 53 | Gm17418 | chr1 | 93885628 | 93889205 | + | ENSMUSG00000079420 |
| 54 | Ladr 54 | Gm16986 | chr13 | 66604096 | 66620459 | − | ENSMUSG00000086120 |
| 55 | Ladr 55 | Gm17656 | chr13 | 66450332 | 66466708 | + | ENSMUSG00000090969 |
| 56 | Ladr 56 | B230206L02Rik | chr11 | 93994799 | 94017090 | + | ENSMUSG00000086003 |
| 57 | Ladr 57 | Abhd1 | chr5 | 31252439 | 31257464 | + | ENSMUSG00000006638 |
| 58 | Ladr 58 | 5930412G12Rik | chr5 | 129084981 | 129106568 | − | ENSMUSG00000072591 |
| 59 | Ladr 59 | E130018N17Rik | chr2 | 167978103 | 167980013 | − | ENSMUSG00000087648 |
| 60 | Ladr 60 | Gm14022 | chr2 | 128886682 | 128891422 | − | ENSMUSG00000087151 |
| 61 | Ladr 61 | Gm2788 | chr7 | 56133328 | 56141978 | + | ENSMUSG00000085995 |
| 62 | Ladr 62 | Gm16880 | chr1 | 138592788 | 138622305 | + | ENSMUSG00000085011 |
| 63 | Ladr 63 | Gm4419 | chr12 | 21423772 | 21425664 | + | ENSMUSG00000090621 |
| 64 | Ladr 64 | 9330185C12Rik | chr1 | 115787962 | 115860711 | − | ENSMUSG00000086520 |
| 65 | Ladr 65 | Gm17659 | chr9 | 89989016 | 89990740 | + | ENSMUSG00000091035 |
| 66 | Ladr 66 | Gm17710 | chr7 | 95427297 | 95432039 | − | ENSMUSG00000091953 |
| 67 | Ladr 67 | Gm10785 | chr16 | 91689156 | 91715887 | + | ENSMUSG00000085169 |
| 68 | Ladr 68 | Gm17561 | chr17 | 32506250 | 32515390 | + | ENSMUSG00000091872 |
| 69 | Ladr 69 | 4930509G22Rik | chr16 | 11178269 | 11192385 | + | ENSMUSG00000085780 |
| 70 | Ladr 70 | C430002E04Rik | chr3 | 41292726 | 41297114 | − | ENSMUSG00000091878 |
| 71 | Ladr 71 | Gm17605 | chr8 | 4088149 | 4089166 | − | ENSMUSG00000091309 |
| 72 | Ladr 72 | Gm17362 | chr8 | 23755333 | 23756758 | + | ENSMUSG00000074911 |
| 73 | Ladr 73 | Gm17525 | chr4 | 128986325 | 128995687 | + | ENSMUSG00000091673 |
| 74 | Ladr 74 | Mirg | chr12 | 110973191 | 110987665 | + | ENSMUSG00000091158 |
| 75 | Ladr 75 | 1010001B22Rik | chr5 | 110424530 | 110425417 | − | ENSMUSG00000091434 |
| 76 | Ladr 76 | Gm17597 | chr15 | 81631221 | 81633043 | − | ENSMUSG00000091934 |
| 77 | Ladr 77 | Gm16283 | chr18 | 49915448 | 49916843 | + | ENSMUSG00000087020 |
| 78 | Ladr 78 | 4933407K13Rik | chrX | 72952271 | 73010038 | − | ENSMUSG00000087396 |
| 79 | Ladr 79 | Gm17279 | chr8 | 19888055 | 20016359 | + | ENSMUSG00000091588 |
| 80 | Ladr 80 | Gm16096 | chr9 | 40588825 | 40592264 | − | ENSMUSG00000087135 |
| 81 | Ladr 81 | Gm17440 | chr7 | 30983649 | 30985908 | + | ENSMUSG00000092079 |
| 82 | Ladr 82 | Gm17594 | chrX | 78316033 | 78318441 | − | ENSMUSG00000078930 |
| 83 | Ladr 83 | Gm13657 | chr2 | 75615245 | 75620363 | + | ENSMUSG00000086813 |
| 84 | Ladr 84 | C330018A13Rik | chr5 | 116573623 | 116579119 | + | ENSMUSG00000086655 |
| 85 | Ladr 85 | Gm17637 | chrX | 20937991 | 20941748 | − | ENSMUSG00000091801 |
| 86 | Ladr 86 | Gm16827 | chr18 | 31940880 | 31948699 | − | ENSMUSG00000086768 |
| 87 | Ladr 87 | Atp10d | chr5 | 72594568 | 72690014 | + | ENSMUSG00000046808 |
| 88 | Ladr 88 | 5730457N03Rik | chr6 | 52258383 | 52264826 | − | ENSMUSG00000086126 |
| 89 | Ladr 89 | Gm11714 | chr11 | 107289590 | 107297000 | + | ENSMUSG00000087113 |
| 90 | Ladr 90 | Gm16159 | chr8 | 26659133 | 26666555 | − | ENSMUSG00000086134 |
| 91 | Ladr 91 | Gm12898 | chr4 | 118895779 | 118897420 | + | ENSMUSG00000085626 |
| 92 | Ladr 92 | Gm16973 | chr14 | 57315117 | 57320105 | − | ENSMUSG00000086985 |
| 93 | Ladr 93 | 6030442K20Rik | chr1 | 134363010 | 134373622 | − | ENSMUSG00000090678 |
| 94 | Ladr 94 | Gm13830 | chr5 | 115751129 | 115769217 | + | ENSMUSG00000086368 |
| 95 | Ladr 95 | C330013F16Rik | chrX | 135774765 | 135892277 | − | ENSMUSG00000086807 |
| 96 | Ladr 96 | 4930467K11Rik | chr10 | 57198187 | 57206159 | − | ENSMUSG00000085621 |
| 97 | Ladr 97 | 2010300F17Rik | chr11 | 96574296 | 96608750 | | ENSMUSG00000091444 |
| 98 | Ladr 98 | Gm2464 | chr3 | 13471906 | 13474596 | − | ENSMUSG00000078587 |
| 99 | Ladr 99 | 9530080011Rik | chr4 | 95626406 | 95634346 | − | ENSMUSG00000044125 |
| 100 | Ladr 100 | 5C046401 | chr2 | 165683184 | 165684534 | + | ENSMUSG00000085274 |
| 101 | Ladr 101 | Gm17481 | chr15 | 78693386 | 78697319 | − | ENSMUSG00000086640 |
| 102 | Ladr 102 | Gm14817 | chrX | 71040554 | 71042955 | − | ENSMUSG00000085669 |
| 103 | Ladr 103 | Gn717501 | chr3 | 145313276 | 145315057 | − | ENSMUSG00000090771 |
| 104 | Ladr 104 | Gm17502 | chr7 | 6296993 | 6300606 | + | ENSMUSG00000091822 |
| 105 | Ladr 105 | 1700023H05Rik | chr13 | 81023485 | 81024785 | − | ENSMUSG00000089827 |
| 106 | Ladr 106 | 4930480K23Rik | chr14 | 70132591 | 70166920 | + | ENSMUSG00000085243 |
| 107 | Ladr 107 | 1110020A21Rik | chr17 | 85354307 | 85357050 | − | ENSMUSG00000087023 |
| 108 | Ladr 108 | Gm16723 | chr6 | 87858837 | 87864453 | − | ENSMUSG00000085703 |

TABLE 1-continued

| SEQ ID NO: | lncRNA | Gene name | chr | left | right | Str* | ID |
|---|---|---|---|---|---|---|---|
| 109 | Ladr 109 | Gm16972 | chr4 | 43058906 | 43066125 | + | ENSMUSG00000086983 |
| 110 | Ladr 110 | GM807 | chr13 | 99870661 | 99877535 | + | ENSMUSG00000074744 |
| 111 | Ladr 111 | D030068K23Rik | chr8 | 111599122 | 111797711 | + | ENSMUSG00000085859 |
| 112 | Ladr 112 | Gm8378 | chr12 | 92913252 | 92924553 | − | ENSMUSG00000090722 |
| 113 | Ladr 113 | Gm12059 | chr11 | 22967998 | 22975574 | + | ENSMUSG00000085665 |
| 114 | Ladr 114 | Gm17716 | chr14 | 26175287 | 26198121 | − | ENSMUSG00000091164 |
| 115 | Ladr 115 | Gm16244 | chr19 | 42853522 | 42855944 | − | ENSMUSG00000090235 |
| 116 | Ladr 116 | 3110045C21Rik | chr1 | 171899540 | 171902526 | + | ENSMUSG00000085494 |
| 117 | Ladr 117 | Gm16845 | chr9 | 21875476 | 21890566 | + | ENSMUSG00000087161 |
| 118 | Ladr 118 | Gm10658 | chr9 | 56904437 | 56919773 | − | ENSMUSG00000074284 |
| 119 | Ladr 119 | A930011O12Rik | chr14 | 65206952 | 65212796 | + | ENSMUSG00000091456 |
| 120 | Ladr 120 | C030010L15Rik | chr16 | 98215766 | 98218584 | − | ENSMUSG00000091751 |
| 121 | Ladr 121 | 4833407H14Rik | chr19 | 53535121 | 53537213 | + | ENSMUSG00000090800 |
| 122 | Ladr 122 | Nespas | chr2 | 174106738 | 174120937 | − | ENSMUSG00000086537 |
| 123 | Ladr 123 | Gm10492 | chr17 | 95234246 | 95235982 | + | ENSMUSG00000073366 |
| 124 | Ladr 124 | Gm17713 | chr1 | 135506988 | 135510999 | + | ENSMUSG00000092104 |
| 125 | Ladr 125 | A930029G22Rik | chr17 | 69766000 | 69788644 | − | ENSMUSG00000085144 |
| 126 | Ladr 126 | Gm16046 | chr17 | 13812667 | 13820523 | − | ENSMUSG00000085705 |
| 127 | Ladr 127 | GM15522 | chr5 | 34993367 | 34995126 | + | ENSMUSG00000085166 |
| 128 | Ladr 128 | Gm11818 | chr4 | 12833984 | 12908632 | + | ENSMUSG00000055963 |
| 129 | Ladr 129 | 1700016P03Rik | chr11 | 74986062 | 74991135 | + | ENSMUSG00000085609 |
| 130 | Ladr 130 | Hoxa11as | chr6 | 52195051 | 52199794 | + | ENSMUSG00000086427 |
| 131 | Ladr 131 | Gm17477 | chr9 | 79966702 | 79969744 | − | ENSMUSG00000084917 |
| 132 | Ladr 132 | C030037DO9Rik | chr11 | 88579959 | 88590207 | + | ENSMUSG00000087574 |
| 133 | Ladr 133 | A330040F15Rik | chr19 | 12660358 | 12671056 | − | ENSMUSG00000086213 |
| 134 | Ladr 134 | Mir155 | chr16 | 84713268 | 84715487 | + | ENSMUSG00000091875 |
| 135 | Ladr 135 | Gm4890 | chr8 | 81819022 | 81831584 | + | ENSMUSG00000085259 |
| 136 | Ladr 136 | 1700028E1ORik | chr5 | 152171284 | 152216658 | + | ENSMUSG00000087548 |
| 137 | Ladr 137 | Gm10575 | chr7 | 148647380 | 148653670 | − | ENSMUSG00000073787 |
| 138 | Ladr 138 | Gm15545 | chr7 | 52242270 | 52249967 | + | ENSMUSG00000087138 |
| 139 | Ladr 139 | A030009H04Rik | chr11 | 69153963 | 69156143 | + | ENSMUSG00000043419 |
| 140 | Ladr 140 | 0610005C13Rik | chr7 | 52823165 | 52830697 | − | ENSMUSG00000085214 |
| 141 | Ladr 141 | Gm17344 | chr8 | 112385625 | 112392355 | − | ENSMUSG00000078143 |
| 142 | Ladr 142 | Gm16761 | chr16 | 29907605 | 29946603 | − | ENSMUSG00000084810 |
| 143 | Ladr 143 | Gm11538 | chr11 | 96064768 | 96066699 | + | ENSMUSG00000085983 |
| 144 | Ladr 144 | A230056P14Rik | chr7 | 63217901 | 63236238 | + | ENSMUSG00000087178 |
| 145 | Ladr 145 | Gm16685 | chr3 | 7612705 | 7690001 | + | ENSMUSG00000086143 |
| 146 | Ladr 146 | Gm17690 | chr3 | 95971387 | 95976337 | − | ENSMUSG00000091244 |
| 147 | Ladr 147 | 4933431E20Rik | chr3 | 107691768 | 107699131 | − | ENSMUSG00000086968 |
| 148 | Ladr 148 | Gm17565 | chr4 | 145686275 | 145688945 | + | ENSMUSG00000090554 |
| 149 | Ladr 149 | 1700030C12Rik | chr11 | 23397753 | 23399661 | + | ENSMUSG00000086459 |
| 150 | Ladr 150 | 2410133F24Rik | chr9 | 56947757 | 56979097 | − | ENSMUSG00000086728 |
| 151 | Ladr 151 | C530005A16Rik | chr4 | 116262338 | 116270235 | − | ENSMUSG00000085408 |
| 152 | Ladr 152 | Gm17254 | chr9 | 96968602 | 96973848 | + | ENSMUSG00000091219 |
| 153 | Ladr 153 | Gm17701 | chr6 | 127058407 | 127060485 | + | ENSMUSG00000091856 |
| 154 | Ladr 154 | Gm15489 | chr7 | 129282522 | 129302915 | − | ENSMUSG00000086942 |
| 155 | Ladr 155 | 9530059O14Rik | chr9 | 122481615 | 122588714 | + | ENSMUSG00000086476 |
| 156 | Ladr 156 | Gm17102 | chr7 | 48649068 | 48652817 | + | ENSMUSG00000091864 |
| 157 | Ladr 157 | Dio3os | chr12 | 111513594 | 111516278 | − | ENSMUSG00000090962 |
| 158 | Ladr 158 | Snord123 | chr15 | 32170324 | 32174417 | − | ENSMUSG00000090401 |
| 159 | Ladr 159 | 1700023L04Rik | chr6 | 29935329 | 29943776 | − | ENSMUSG00000045709 |
| 160 | Ladr 160 | Gdap10 | chr12 | 33506737 | 33511769 | + | ENSMUSG00000059937 |
| 161 | Ladr 161 | Gm17500 | chr11 | 51938032 | 51941281 | − | ENSMUSG00000092028 |
| 162 | Ladr 162 | Gm17692 | chr17 | 6314199 | 6492328 | + | ENSMUSG00000091795 |
| 163 | Ladr 163 | Gm12784 | chr7 | 35332225 | 35341223 | + | ENSMUSG00000086631 |
| 164 | Ladr 164 | 2810011L19Rik | chr12 | 106574804 | 106622141 | + | ENSMUSG00000086023 |
| 165 | Ladr 165 | Gm16618 | chr16 | 20511206 | 20517839 | − | ENSMUSG00000086837 |
| 166 | Ladr 165 | Gm16912 | chr17 | 29598841 | 29628870 | − | ENSMUSG00000087551 |
| 167 | Ladr 167 | Gm12592 | chr11 | 3205429 | 3231181 | − | ENSMUSG00000053263 |
| 168 | Ladr 168 | Gm13261 | chr2 | 10260910 | 10295668 | − | ENSMUSG00000086748 |
| 169 | Ladr 169 | C330002G04Rik | chr19 | 23111880 | 23150343 | − | ENSMUSG00000087169 |
| 170 | Ladr 170 | Gm16869 | chr9 | 3000282 | 3038313 | − | ENSMUSG00000087580 |
| 171 | Ladr 171 | Gn16938 | chr7 | 105325704 | 105334107 | + | ENSMUSG00000086325 |
| 172 | Ladr 172 | F630040L22Rik | chr9 | 108007296 | 108020674 | + | ENSMUSG00000087645 |
| 173 | Ladr 173 | Gm17445 | chr7 | 26601673 | 26605673 | + | ENSMUSG00000084812 |
| 174 | Ladr 174 | AY512931 | chr8 | 46146056 | 46150772 | + | ENSMUSG00000066158 |
| 175 | Ladr 175 | Gm6410 | chr8 | 4678462 | 4688494 | + | ENSMUSG00000090435 |
| 176 | Ladr 176 | A930007I19Rik | chr19 | 29560845 | 29597649 | − | ENSMUSG00000086309 |
| 177 | Ladr 177 | 3010001F23Rik | chrX | 148803116 | 148851241 | + | ENSMUSG00000084885 |
| 178 | Ladr 178 | A330076H08Rik | chr7 | 69075799 | 69127242 | − | ENSMUSG00000087490 |
| 179 | Ladr 179 | Gm15850 | chr1 | 138022755 | 138027760 | − | ENSMUSG00000086264 |
| 180 | Ladr 180 | Gm10425 | chr12 | 112665085 | 112669157 | − | ENSMUSG00000072830 |
| 181 | Ladr 181 | Gm16629 | chr15 | 92174790 | 92208519 | + | ENSMUSG00000085294 |
| 182 | Ladr 182 | 2900052L18Rik | chr11 | 120091116 | 120092899 | − | ENSMUSG00000043993 |
| 183 | Ladr 183 | 2310031A07Rik | chr11 | 46253864 | 46260750 | − | ENSMUSG00000091190 |
| 184 | Ladr 184 | 4930506C21Rik | chr17 | 8486231 | 8503945 | − | ENSMUSG00000087478 |
| 185 | Ladr 185 | Gm16733 | chr7 | 20355960 | 20360752 | + | ENSMUSG00000085994 |

TABLE 1-continued

| SEQ ID NO: | lncRNA | Gene name | chr | left | right | Str* | ID |
|---|---|---|---|---|---|---|---|
| 186 | Ladr 186 | Gm11574 | chr11 | 96910005 | 96912746 | − | ENSMUSG00000085262 |
| 187 | Ladr 187 | 2810429I04Rik | chr13 | 3477489 | 3493644 | + | ENSMUSG00000086566 |
| 188 | Ladr 188 | A230004M16Rik | chr11 | 41523844 | 41786619 | + | ENSMUSG00000087306 |
| 189 | Ladr 189 | Gm17392 | chr17 | 55696464 | 55702805 | + | ENSMUSG00000090426 |
| 190 | Ladr 190 | Gm17699 | chr1 | 130667176 | 130670998 | − | ENSMUSG00000091877 |
| 191 | Ladr 191 | A730099G02Rik | chr10 | 48939228 | 48945459 | − | ENSMUSG00000091943 |
| 192 | Ladr 192 | Gm17644 | chr1 | 12657644 | 12663171 | + | ENSMUSG00000066918 |
| 193 | Ladr 193 | Gm17255 | chr9 | 80849043 | 81097197 | + | ENSMUSG00000090679 |
| 194 | Ladr 194 | Gm17638 | chr15 | 77792104 | 77797556 | + | ENSMUSG00000091802 |
| 195 | Ladr 195 | Gm16755 | chr11 | 120347653 | 120349896 | − | ENSMUSG00000086218 |
| 196 | Ladr 196 | Gm16702 | chr17 | 8571910 | 8582333 | − | ENSMUSG00000086627 |
| 197 | Ladr 197 | Gm11934 | chr4 | 33390544 | 33397112 | − | ENSMUSG00000086127 |
| 198 | Ladr 198 | Gm15396 | chr7 | 51835338 | 51845994 | − | ENSMUSG00000087560 |
| 199 | Ladr 199 | Gm3906 | chr9 | 43921006 | 43930030 | + | ENSMUSG00000092003 |
| 200 | Ladr 200 | Gm12976 | chr4 | 128939209 | 128942254 | + | ENSMUSG00000087575 |
| 201 | Ladr 201 | Gm16862 | chr17 | 45871455 | 45925543 | + | ENSMUSG00000086615 |
| 202 | Ladr 202 | Gm17496 | chr16 | 95237977 | 95288624 | + | ENSMUSG00000092023 |
| 203 | Ladr 203 | BC051077 | chr5 | 117762529 | 117765548 | − | ENSMUSG00000091333 |
| 204 | Ladr 204 | Gm17632 | chr3 | 116191884 | 116196276 | + | ENSMUSG00000090721 |
| 205 | Ladr 205 | Gm17275 | chr1 | 182732699 | 182739614 | + | ENSMUSG00000090986 |
| 206 | Ladr 206 | Gm17596 | chr9 | 57379094 | 57385436 | − | ENSMUSG00000091932 |
| 207 | Ladr 207 | Gm17327 | chr7 | 35009774 | 35015255 | + | ENSMUSG00000090311 |
| 208 | Ladr 208 | Gm17599 | chr4 | 43043871 | 43045354 | + | ENSMUSG00000091065 |
| 209 | Ladr 209 | Gm17517 | chr8 | 60650232 | 60777663 | + | ENSMUSG00000091944 |
| 210 | Ladr 210 | Gm17336 | chr10 | 128082940 | 128086867 | + | ENSMUSG00000091431 |
| 211 | Ladr 211 | A330032B11Rik | chr19 | 37248333 | 37271031 | + | ENSMUSG00000085432 |
| 212 | Ladr 212 | 1700007J10Rik | chr11 | 59539419 | 59553656 | − | ENSMUSG00000086330 |
| 213 | Ladr 213 | Gm11542 | chr11 | 94538879 | 94548978 | + | ENSMUSG00000085051 |
| 214 | Ladr 214 | 4833417C18Rik | chr11 | 95720179 | 95722358 | + | ENSMUSG00000086015 |
| 215 | Ladr 215 | Gm17282 | chr13 | 69948792 | 69954972 | − | ENSMUSG00000091909 |
| 216 | Ladr 216 | Mir706 | chr6 | 119983540 | 119986489 | − | ENSMUSG00000090388 |
| 217 | Ladr 217 | 6430562O15Rik | chr13 | 100166879 | 100182819 | − | ENSMUSG00000085195 |
| 218 | Ladr 218 | Gm7782 | chr13 | 65480701 | 65553664 | − | ENSMUSG00000090514 |
| 219 | Ladr 219 | 2610027K06Rik | chr11 | 85605163 | 85645725 | − | ENSMUSG00000087013 |
| 220 | Ladr 220 | 1110046J04Rik | chr13 | 34027689 | 34028499 | + | ENSMUSG00000085457 |
| 221 | Ladr 221 | Gm17675 | chr2 | 120358640 | 120365582 | + | ENSMUSG00000091714 |
| 222 | Ladr 222 | A730081D07Rik | chr13 | 41051783 | 41096520 | − | ENSMUSG00000086693 |
| 223 | Ladr 223 | 2610206C17Rik | chr7 | 91838150 | 91925059 | + | ENSMUSG00000085236 |
| 224 | Ladr 224 | 1110019D14Rik | chr6 | 13821526 | 13994373 | + | ENSMUSG00000084815 |
| 225 | Ladr 225 | Gm16706 | chr11 | 79830856 | 79843370 | − | ENSMUSG00000086787 |
| 226 | Ladr 226 | Gm17317 | chr4 | 146510387 | 146831128 | + | ENSMUSG00000091833 |
| 227 | Ladr 227 | Gm16889 | chr4 | 146392344 | 146866310 | − | ENSMUSG00000084976 |
| 228 | Ladr 228 | Gm17452 | chr4 | 146120857 | 146399068 | − | ENSMUSG00000092143 |
| 229 | Ladr 229 | Gm16739 | chr5 | 110351668 | 110352500 | − | ENSMUSG00000085131 |
| 230 | Ladr 230 | Gm11602 | chr1 | 63161045 | 63204864 | + | ENSMUSG00000084799 |
| 231 | Ladr 231 | Gm16684 | chr17 | 32947089 | 32958642 | + | ENSMUSG00000085948 |
| 232 | Ladr 232 | Gm17548 | chr3 | 63767555 | 63772581 | + | ENSMUSG00000091540 |
| 233 | Ladr 233 | Gm2366 | chr8 | 46102570 | 46107739 | − | ENSMUSG00000091546 |
| 234 | Ladr 234 | Gm17529 | chr12 | 60054082 | 60068998 | + | ENSMUSG00000092098 |
| 235 | Ladr 235 | Gm17451 | chr6 | 38501531 | 38504007 | − | ENSMUSG00000092140 |
| 236 | Ladr 236 | 3100003L05Rik | chr7 | 131769184 | 131852449 | − | ENSMUSG00000086254 |
| 237 | Ladr 237 | 2810425M01Rik | chr10 | 76949409 | 76979175 | + | ENSMUSG00000086832 |
| 238 | Ladr 238 | Gm17238 | chr18 | 67933366 | 67934511 | − | ENSMUSG00000091127 |
| 239 | Ladr 239 | 2010110K18Rik | chr18 | 34911463 | 34918339 | + | ENSMUSG00000085410 |
| 240 | Ladr 240 | Gm17499 | chr10 | 90612260 | 90613339 | + | ENSMUSG00000092024 |
| 241 | Ladr 241 | Gm9917 | chr9 | 107461141 | 107470746 | − | ENSMUSG00000053666 |
| 242 | Ladr 242 | Gm16568 | chr9 | 15135017 | 15139789 | + | ENSMUSG00000089702 |
| 243 | Ladr 243 | Gm16624 | chr5 | 24202720 | 24210508 | − | ENSMUSG00000084903 |
| 244 | Ladr 244 | 1500026H17Rik | chr10 | 89149116 | 89163611 | + | ENSMUSG00000087686 |
| 245 | Ladr 245 | 1700109K24Rik | chr15 | 76914873 | 76926744 | + | ENSMUSG00000087126 |
| 246 | Ladr 246 | 2010204K13Rik | chrX | 6988943 | 7022269 | − | ENSMUSG00000063018 |
| 247 | Ladr 247 | 2010320O07Rik | chr18 | 38369426 | 38388799 | + | ENSMUSG00000089983 |
| 248 | Ladr 248 | 2610035F20Rik | chr14 | 122869506 | 122872801 | − | ENSMUSG00000085555 |
| 249 | Ladr 249 | 2810430I11Rik | chr2 | 27738445 | 27742572 | − | ENSMUSG00000085765 |
| 250 | Ladr 250 | 2900041M22Rik | chr11 | 117472561 | 117475171 | + | ENSMUSG00000054418 |
| 251 | Ladr 251 | 4732463B04Rik | chr12 | 85380419 | 85394757 | − | ENSMUSG00000086299 |
| 252 | Ladr 252 | 4833412C05Rik | chr7 | 74929611 | 74948382 | − | ENSMUSG00000085850 |
| 253 | Ladr 253 | 4930544I03Rik | chr12 | 91991648 | 92208208 | − | ENSMUSG00000092100 |
| 254 | Ladr 254 | 4932430I15Rik | chr5 | 93233246 | 93238514 | − | ENSMUSG00000072828 |
| 255 | Ladr 255 | 4933427G23Rik | chr5 | 23321436 | 23337715 | − | ENSMUSG00000086697 |
| 256 | Ladr 256 | 5330411J11Rik | chr2 | 59220559 | 59225528 | − | ENSMUSG00000087455 |
| 257 | Ladr 257 | 5430416N02Rik | chr5 | 100849861 | 100858535 | − | ENSMUSG00000084877 |
| 258 | Ladr 258 | 7530420F21Rik | chr1 | 151922003 | 151947004 | − | ENSMUSG00000084952 |
| 259 | Ladr 259 | 8030451A03Rik | chr4 | 63640888 | 63810958 | + | ENSMUSG00000073821 |
| 260 | Ladr 260 | A230028O05Rik | chr16 | 25059725 | 25069144 | + | ENSMUSG00000085040 |
| 261 | Ladr 261 | A330094K24Rik | chr18 | 77968420 | 77972209 | − | ENSMUSG00000090400 |
| 262 | Ladr 262 | A930001C03Rik | chr19 | 4439003 | 4448332 | + | ENSMUSG00000087132 |

TABLE 1-continued

| SEQ ID NO: | lncRNA | Gene name | chr | left | right | Str* | ID |
|---|---|---|---|---|---|---|---|
| 263 | Ladr 263 | AI854517 | chr7 | 86645003 | 86679283 | + | ENSMUSG00000085554 |
| 264 | Ladr 264 | Airn | chr17 | 12934177 | 13052988 | + | ENSMUSG00000078247 |
| 265 | Ladr 265 | B230354K17Rik | chr17 | 45570801 | 45579493 | + | ENSMUSG00000073393 |
| 266 | Ladr 266 | C130021I20Rik | chr2 | 33496713 | 33501869 | + | ENSMUSG00000052951 |
| 267 | Ladr 267 | C130071C03Rik | chr13 | 83861160 | 83880913 | + | ENSMUSG00000050334 |
| 268 | Ladr 268 | Emx2os | chr19 | 59499594 | 59533125 | − | ENSMUSG00000087095 |
| 269 | Ladr 269 | Fam150a | chr1 | 6349537 | 6384812 | + | ENSMUSG00000087247 |
| 270 | Ladr 270 | G730013B05Rik | chr16 | 50526417 | 50559548 | + | ENSMUSG00000085617 |
| 271 | Ladr 271 | Gm10561 | chr1 | 55283095 | 55292466 | + | ENSMUSG00000073675 |
| 272 | Ladr 272 | Gm11019 | chr13 | 98204925 | 98266960 | + | ENSMUSG00000078952 |
| 273 | Ladr 273 | Gm12100 | chr11 | 30650832 | 30656147 | + | ENSMUSG00000087474 |
| 274 | Ladr 274 | Gm13939 | chr2 | 109742553 | 109753476 | − | ENSMUSG00000063751 |
| 275 | Ladr 275 | Gm14261 | chr2 | 168591643 | 168593608 | + | ENSMUSG00000085322 |
| 276 | Ladr 276 | Gm15270 | chr10 | 24269247 | 24316914 | − | ENSMUSG00000087400 |
| 277 | Ladr 277 | Gm15283 | chr12 | 75027468 | 75050772 | − | ENSMUSG00000087700 |
| 278 | Ladr 278 | Gm16070 | chr1 | 17666108 | 17717727 | − | ENSMUSG00000085125 |
| 279 | Ladr 279 | Gm16091 | chr8 | 74671500 | 74684754 | − | ENSMUSG00000087502 |
| 280 | Ladr 280 | Gm16233 | chr3 | 144610525 | 144617842 | + | ENSMUSG00000085773 |
| 281 | Ladr 281 | Gm16704 | chr19 | 34549298 | 34556036 | + | ENSMUSG00000085164 |
| 282 | Ladr 282 | Gm16707 | chr9 | 119349396 | 119353948 | − | ENSMUSG00000086780 |
| 283 | Ladr 283 | Gm16789 | chr16 | 35806033 | 35809032 | − | ENSMUSG00000086400 |
| 284 | Ladr 284 | Gm16882 | chr18 | 37906213 | 37927896 | − | ENSMUSG00000085906 |
| 285 | Ladr 285 | Gm16896 | chr6 | 89254624 | 89277615 | + | ENSMUSG00000085988 |
| 286 | Ladr 286 | Gm16952 | chr17 | 71094669 | 71104922 | − | ENSMUSG00000087105 |
| 287 | Ladr 287 | Gm17256 | chr12 | 88673438 | 88676605 | + | ENSMUSG00000090672 |
| 288 | Ladr 288 | Gm17278 | chr13 | 65691229 | 65692497 | − | ENSMUSG00000091589 |
| 289 | Ladr 289 | Gm17311 | chr1 | 152006173 | 152012078 | − | ENSMUSG00000091113 |
| 290 | Ladr 290 | Gm17322 | chr9 | 57845848 | 57855258 | + | ENSMUSG00000091267 |
| 291 | Ladr 291 | Gm17396 | chr9 | 117161654 | 117163814 | + | ENSMUSG00000079669 |
| 292 | Ladr 292 | Gm17431 | chr5 | 5781530 | 5783636 | + | ENSMUSG00000091282 |
| 293 | Ladr 293 | Gm17443 | chr8 | 33118976 | 33126231 | + | ENSMUSG00000091819 |
| 294 | Ladr 294 | Gm17513 | chr2 | 177758513 | 177763441 | − | ENSMUSG00000090944 |
| 295 | Ladr 295 | Gm17514 | chr13 | 66284015 | 66304572 | − | ENSMUSG00000090945 |
| 296 | Ladr 296 | Gm17520 | chr1 | 173353316 | 173367449 | − | ENSMUSG00000092117 |
| 297 | Ladr 297 | Gm17560 | chr1 | 93193780 | 93200982 | − | ENSMUSG00000091871 |
| 298 | Ladr 298 | Gm17575 | chr3 | 96179569 | 96192787 | − | ENSMUSG00000091380 |
| 299 | Ladr 299 | Gm17609 | chr4 | 145191866 | 145301871 | − | ENSMUSG00000090398 |
| 300 | Ladr 300 | Gm17685 | chr7 | 152080465 | 152083366 | − | ENSMUSG00000090767 |
| 301 | Ladr 301 | Gm17718 | chr1 | 138518675 | 138521227 | − | ENSMUSG00000091667 |
| 302 | Ladr 302 | Gm17724 | chr5 | 110814854 | 110817092 | + | ENSMUS000000090661 |
| 303 | Ladr 303 | Gm17735 | chr13 | 66345152 | 66365458 | + | ENSMUSG00000090502 |
| 304 | Ladr 304 | Gm2115 | chr7 | 91677485 | 91726847 | + | ENSMUSG00000085128 |
| 305 | Ladr 305 | Gm4349 | chr3 | 95231593 | 95235009 | + | ENSMUSG00000091761 |
| 306 | Ladr 306 | Gm6634 | chr3 | 70576301 | 70611213 | − | ENSMUSG00000086538 |
| 307 | Ladr 307 | Gm6846 | chr10 | 21550305 | 21564657 | − | ENSMUSG00000085422 |
| 308 | Ladr 308 | Igf2as | chr7 | 149845598 | 149856261 | + | ENSMUSG00000086266 |
| 309 | Ladr 309 | Miat | chr5 | 112642248 | 112657968 | − | ENSMUSG00000086878 |
| 310 | Ladr 310 | Rgs22 | chr15 | 36067976 | 36070140 | − | ENSMUSG00000091092 |
| 311 | Ladr 311 | Sox2ot | chr3 | 34459303 | 34579773 | + | ENSMUSG00000090828 |
| 312 | Ladr 312 | Tdrd5 | chr1 | 158185426 | 158233795 | − | ENSMUSG00000060985 |
| 313 | Ladr 313 | Tsix | chrX | 100626856 | 100680296 | + | ENSMUSG00000085715 |
| 314 | Ladr 314 | Ttc28 | chr5 | 111308822 | 111718800 | + | ENSMUSG00000033209 |

*DNA strand: + = positive; − = negative

TABLE 2

Upregulated Mouse and Human lncRNA orthologs upon induction of pluripotency

| SEQ ID NO: | lncRNA | chr-mm9 | left-mm9 | right-mm9 |
|---|---|---|---|---|
| 50 | Ladr50 | chr10 | 66375237 | 66383006 |
| 129 | Ladr129 | chr11 | 74986062 | 74991135 |
| 136 | Ladr136 | chr5 | 152171284 | 152216658 |
| 150 | Ladr150 | chr9 | 56947757 | 56979097 |
| 164 | Ladr164 | chr12 | 106574804 | 106622141 |
| 236 | Ladr236 | chr7 | 131769184 | 131852449 |
| 32 | Ladr32 | chr7 | 99886168 | 99889978 |
| 48 | Ladr48 | chr1 | 57416066 | 57434348 |
| 88 | Ladr88 | chr6 | 52258383 | 52264826 |
| 58 | Ladr58 | chr5 | 129084981 | 129106568 |
| 259 | Ladr259 | chr4 | 63640888 | 63810958 |
| 176 | Ladr176 | chr19 | 29560845 | 29597649 |
| 263 | Ladr263 | chr7 | 86645003 | 86679283 |
| 264 | Ladr264 | chr17 | 12934177 | 13052988 |
| 56 | Ladr56 | chr11 | 93994799 | 94017090 |
| 267 | Ladr267 | chr13 | 83861160 | 83880913 |
| 84 | Ladr84 | chr5 | 116573623 | 116579119 |
| 111 | Ladr111 | chr8 | 111599122 | 111797711 |
| 157 | Ladr157 | chr12 | 111513594 | 111516278 |
| 272 | Ladr272 | chr13 | 98204925 | 98266960 |
| 230 | Ladr230 | chr1 | 63161045 | 63204864 |
| 277 | Ladr277 | chr12 | 75027468 | 75050772 |
| 154 | Ladr154 | chr7 | 129282522 | 129302915 |
| 279 | Ladr279 | chr8 | 74671500 | 74684754 |
| 145 | Ladr145 | chr3 | 7612705 | 7690001 |
| 282 | Ladr282 | chr9 | 119349396 | 119353948 |
| 142 | Ladr142 | chr16 | 29907605 | 29946603 |

TABLE 2-continued

Upregulated Mouse and Human lncRNA orthologs upon induction of pluripotency

| | | | | |
|---|---|---|---|---|
| 201 | Ladr201 | chr17 | 45871455 | 45925543 |
| 141 | Ladr141 | chr8 | 112385625 | 112392355 |
| 192 | Ladr192 | chr1 | 12657644 | 12663171 |
| 43 | Ladr43 | chr8 | 89996711 | 90049453 |
| 135 | Ladr135 | chr8 | 81819022 | 81831584 |
| 110 | Ladr110 | chr13 | 99870661 | 99877535 |
| 130 | Ladr130 | chr6 | 52195051 | 52199794 |
| 18 | Ladr18 | chr12 | 110779211 | 110809936 |
| 134 | Ladr134 | chr16 | 84713268 | 84715487 |
| 74 | Ladr74 | chr12 | 110973191 | 110987665 |
| 21 | Ladr21 | chr12 | 110842155 | 110899919 |
| 158 | Ladr158 | chr15 | 32170324 | 32174417 |
| 311 | Ladr311 | chr3 | 34459303 | 34579773 |
| 313 | Ladr313 | chrX | 100626856 | 100680296 |
| 30 | Ladr30 | chr6 | 83642800 | 83662195 |
| 47 | Ladr47 | chrX | 100655714 | 100678556 |

| SEQ ID NO: | chr-hc19 | left-hg19 | right-hg19 |
|---|---|---|---|
| 315 | chr10 | 65473608 | 65477165 |
| 316 | chr17 | 1946762 | 1954455 |
| 317 | chr13 | 34116876 | 34220938 |
| 318 | chr15 | 75660404 | 75699561 |
| 319 | chr14 | 96342568 | 96391908 |
| 320 | chr16 | 26306223 | 26376651 |
| 321 | chr11 | 82783096 | 82790139 |
| 322 | chr2 | 200761331 | 200775882 |
| 323 | chr7 | 27277134 | 27283643 |
| 324 | chr12 | 130624758 | 130646888 |
| 325 | chr9 | 117806328 | 117983873 |
| 326 | chr9 | 5582670 | 5629781 |
| 327 | chr15 | 89905832 | 89941709 |
| 328 | chr6 | 160303155 | 160413129 |
| 329 | chr17 | 49002131 | 49028278 |
| 330 | chr5 | 87960259 | 87980578 |
| 331 | chr12 | 119969729 | 119982930 |
| 332 | chr16 | 72438983 | 72698902 |
| 333 | chr14 | 102023636 | 102026673 |
| 334 | chr5 | 73669250 | 73730264 |
| 335 | chr2 | 206950705 | 207007651 |
| 336 | chr14 | 62187023 | 62217777 |
| 337 | chr16 | 23673394 | 23690117 |
| 338 | chr19 | 16205669 | 16222211 |
| 339 | chr8 | 79716708 | 79814703 |
| 340 | chr3 | 38532681 | 38537742 |
| 341 | chr3 | 193692107 | 193721538 |
| 342 | chr6 | 43991381 | 44043849 |
| 343 | chr16 | 71757936 | 71765413 |
| 344 | chr8 | 70356940 | 70361515 |
| 345 | chr16 | 49315971 | 49372596 |
| 346 | chr4 | 146521236 | 146540150 |
| 347 | chr5 | 71895453 | 71900248 |
| 348 | chr7 | 27224096 | 27228917 |
| 349 | chr14 | 101292457 | 101327362 |
| 350 | chr21 | 26945089 | 26947227 |
| 351 | chr14 | 101521835 | 101539271 |
| 352 | chr14 | 101361216 | 101417326 |
| 353 | chr5 | 9546382 | 9550405 |
| 354 | chr3 | 181328327 | 181461409 |
| 355 | chrX | 73014340 | 73073529 |
| 356 | chr2 | 71099447 | 71128657 |
| 357 | chrX | 73040495 | 73072548 |

Additional human Lairs were identified in human skin fibroblasts upon induction of pluripotency reprogramming. These human lncRNAs include SEQ ID NOs. 368-408 as listed in Table 3.

TABLE 3

Human lncRNAs upregulated during pluripotency reprogramming of primary skin fibroblasts.

| SEQ ID NO: | lncRNA | chr-hg19 | str | left-hg19 | right-hg19 |
|---|---|---|---|---|---|
| 368 | RP11-426L16.8 | chr1 | − | 113362792 | 113393265 |
| 369 | AC008069.3 | chr2 | − | 16973247 | 16978722 |
| 370 | RP11-5N23.2 | chr10 | + | 6622381 | 6627641 |
| 371 | AL513497.1 | chr1 | − | 28835514 | 28837109 |
| 372 | AC021224.1 | chr18 | + | 29992145 | 29993199 |
| 373 | RP11-308B16.1 | chr5 | + | 12574969 | 12804475 |
| 374 | AC022409.1 | chr19 | − | 23582041 | 23598873 |
| 375 | AP002856.5 | chr11 | + | 131123317 | 131170666 |
| 376 | AC074289.1 | chr2 | + | 64370373 | 64479993 |
| 377 | RP11-342C23.4 | chr9 | + | 97320996 | 97330312 |
| 378 | AL133167.1 | chr14 | + | 96342729 | 96391899 |
| 379 | RP11-277P12.10 | chr12 | − | 10485460 | 10490891 |
| 380 | AP003486.1 | chr11 | − | 130434325 | 130628495 |
| 381 | RMST | chr12 | + | 97858799 | 97958793 |
| 382 | KIAA0040 | chr1 | − | 175126123 | 175162079 |
| 383 | AC010627.1 | chr5 | + | 14651755 | 14653492 |
| 384 | RP11-69I8.2 | chr6 | + | 132223103 | 132241705 |
| 385 | AC009163.1 | chr16 | + | 75507023 | 75529305 |
| 386 | AL136362.1 | chrX | − | 91354536 | 91360178 |
| 387 | MIR17HG | chr13 | + | 92000074 | 92006833 |
| 388 | RP11-771K4.1 | chr12 | − | 31516415 | 31522235 |
| 389 | AC078819.1 | chr12 | − | 104424522 | 104426026 |
| 390 | AP000689.1 | chr21 | − | 37502670 | 37648524 |
| 391 | RP11-562F9.2 | chr4 | − | 93189918 | 93198226 |
| 392 | RP11-168P6.1 | chr13 | − | 54689924 | 54707001 |
| 393 | RP11-168O16.1 | chr1 | + | 200993077 | 200997920 |
| 394 | RP11-713B9.1 | chr11 | + | 115045697 | 115046044 |
| 395 | SOX2OT | chr3 | + | 180721562 | 181508734 |
| 396 | RP11-403C10.2 | chr8 | − | 9757574 | 9762876 |
| 397 | RP11-697K23.1 | chr3 | − | 45720535 | 45730626 |
| 398 | AC020928.1 | chr19 | + | 37264055 | 37267978 |
| 399 | RP11-366M4.3 | chr4 | + | 165798156 | 165820117 |
| 400 | RP11-20D14.6 | chr12 | + | 8940853 | 8948385 |
| 401 | AC126775.1 | chr5 | + | 146939557 | 147041572 |
| 402 | AL691420.1 | chr9 | + | 118235807 | 118353358 |
| 403 | AC005753.1 | chr5 | + | 141227143 | 141231803 |
| 404 | RP11-799O21.1 | chr10 | + | 6821560 | 6884868 |
| 405 | RP11-129K20.2 | chr3 | + | 62936105 | 63110738 |
| 406 | AC112484.1 | chr3 | − | 128679210 | 128684200 |
| 407 | AC005394.1 | chr19 | − | 28926300 | 29218587 |

DNA strand: + = positive strand; − = negative strand

In other embodiments of the present invention, improved somatic cell reprogramming includes the absence or repression of the lncRNAs disclosed herein to be downregulated during reprogramming of the somatic cells. The lncRNAs which are disclosed herein to be downregulated during induced pluripotency include the mouse lncRNAs (SEQ ID NOs. 415-424) as listed in Table 4A and the human lncRNAs (SEQ ID NOs. 358-367) as listed in Table 4B.

In some embodiments, decreasing the expression or cellular activity in mouse cells includes using one or more of the mouse lncRNAs encoded by SEQ ID NOs: 415-424, or decreasing the expression or cellular activity in human cells using one or more of the human lncRNAs enclosed by SEQ ID NOs. 358-367 as listed in Table 4B.

TABLE 4A

Mouse (mm9) downregulated lncRNAs during iPS cell reprogramming

| lncRNA | SEQ ID NO: | chr-mm9 | Str* | left-mm9 | right-mm9 |
|---|---|---|---|---|---|
| 2210408F21Rik | 415 | chr6 | + | 31170351 | 31287404 |
| D030054H15Rik | 416 | chr17 | − | 8075373 | 8139217 |
| Gm13986 | 417 | chr2 | − | 117683027 | 117936938 |
| Gm14005 | 418 | chr2 | − | 128021729 | 128255085 |

TABLE 4A-continued

Mouse (mm9) downregulated lncRNAs during iPS cell reprogramming

| lncRNA | SEQ ID NO: | chr-mm9 | Str* | left-mm9 | right-mm9 |
|---|---|---|---|---|---|
| Gm14488 | 419 | chr2 | − | 30568667 | 30575577 |
| Gm16625 | 420 | chr8 | + | 25532876 | 25550480 |
| 1700020I14Rik | 421 | chr2 | + | 119420033 | 119433238 |
| 2410006H16Rik | 422 | chr11 | + | 62416379 | 62418309 |
| 9430037G07Rik | 423 | chr9 | − | 88490163 | 88494354 |
| Gm17480 | 424 | chr17 | + | 25931839 | 26101729 |

*DNA strand: + = positive strand; − = negative strand

TABLE 4B

Human (hg19) liftOver coordinates of mm9 in Table 4A.

| lncRNA | SEQ ID NO: | chr-hg19 | left-hg19 | right-hg19 |
|---|---|---|---|---|
| 2210408F21Rik | 358 | chr7 | 130794788 | 130934427 |
| D030054H15Rik | 359 | chr6 | 159420370 | 159509319 |
| Gm13986 | 360 | chr15 | 39537299 | 39872516 |
| Gm14005 | 361 | chr2 | 111966340 | 112252695 |
| Gm14488 | 362 | chr9 | 132251908 | 132259983 |
| Gm16625 | 363 | chr8 | 40009983 | 40028634 |
| 1700020I14Rik | 364 | chr15 | 41576169 | 41598737 |
| 2410006H16Rik | 365 | chr17 | 16342356 | 16345222 |
| 9430037G07Rik | 366 | chr6 | 86386845 | 86388510 |
| Gm17480 | 367 | chr16 | 597538 | 767429 |

Additional human downregulated lncRNAs were identified in human skin fibroblasts upon induction of pluripotency reprogramming. These human lncRNAs include SEQ ID NOs. 408-414 as listed in Table 5.

Table 5. Downregulated human lncRNAs during induced pluripotency in human skin fibroblasts

| SEQ ID NO: | lncRNA | chr-hg19 | str* | left-hg19 | right-hg19 |
|---|---|---|---|---|---|
| 408 | C17orf91 | chr17 | − | 1614805 | 1619504 |
| 409 | AC005323.1 | chr17 | + | 10286461 | 10527704 |
| 410 | RP11-834C11.4 | chr12 | + | 54519882 | 54526627 |
| 411 | RP11-792D21.2 | chr4 | + | 79567057 | 79603853 |
| 412 | AP000769.4 | chr11 | + | 65211929 | 65212028 |
| 413 | RP11-90J7.3 | chr10 | + | 80008497 | 80434724 |
| 414 | NEAT1 | chr11 | + | 65190245 | 65213011 |

*DNA strand: + = positive strand; − = negative strand

Embodiments of the present invention include lncRNAs which are upregulated or downregulated upon induction of pluripotency and/or inhibition of Mek and Gsk3, referred to herein as "2i inhibition" or "2i conditions." In some embodiments of the present invention, improved pluripotency by reprogramming of a somatic cell, includes the presence of the activated lncRNAs (i.e., Ladrs) in a pluripotency cell reaction. Methods for reprogramming of human induced pluripotent stem cells is described herein and has been previously described in Loewer et al., 2010, *Nature Genetics*, 42: 1113-1117, the entire contents of which are herein incorporated by reference. For example, reprogramming of induced pluripotent stem cells may include induction of the Oct4, Sox2, Klf4, c-Myc (OSKM) transcription factors and/or the "dual inhibition" of Mek and Gsk3 also known as "2i."

In some embodiments, the lncRNA and lncRNA fragments of the present invention include fragments of the sequence that are at least 20 nucleotides (nt) in length. In one embodiment, an lncRNA molecule includes a nucleotide sequence that is at least about 85% or more homologous or identical to the entire length of a lncRNA sequence shown herein, e.g., in Tables 1, 2, 3, 4, or 5, or a fragment comprising at least 20 nt thereof (e.g., at least 25, 30, 35, 40, 50, 60, 70, 80, 90, or 100 nt thereof, e.g., at least 5%, 10%, 15%, 20%, 25%, 30%, 35%, 40%, 50% or more of the full length lncRNA). In some embodiments, the nucleotide sequence is at least about 90%, 91%, 92%, 93%, 94%, 95%, 96%, 97%, 98%, 99% or 100% homologous or identical to a lncRNA sequence shown herein.

In Tables 1, 2, 3, 4, and 5 disclosed herein the genomic coordinates are provided for each lncRNA. As understood by a person having ordinary skill in the art, any lncRNA transcripts that overlap by at least 1 base pair with the genomic coordinates of the lncRNAs disclosed herein, should be considered isoforms of these lncRNAs with analogous functional roles during somatic cell reprogramming or pluripotent stem cell differentiation.

In order to determine the percent identity of two nucleic acid sequences, the sequences are aligned for optimal comparison purposes (e.g., gaps can be introduced in an nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences.

For purposes of the present invention, the comparison of sequences and determination of percent identity between two sequences may be accomplished using a Blossum 62 scoring matrix with a gap penalty of 12, a gap extend penalty of 4, and a frameshift gap penalty of 5.

Methods of Pluripotency Reprogramming or Pluripotent Cell Differentiation.

Methods of enhancing pluripotency reprogramming or pluripotent cell differentiation are disclosed herein. The lncRNAs described herein, including fragments thereof that are at least 20 nt in length, and inhibitory nucleic acids and small molecules targeting (e.g., complementary to) them, can be used to modulate pluripotency reprogramming. Methods for enchanced pluripotency reprogramming include the addition or activation of Ladr molecules disclosed in Tables 1, 2, and/or 3 and/or the inhibition of the lncRNAs disclosed in Tables 4A, 4B and/or 5. Conversely, enchancing pluripotent cell differentiation includes the absence or repression of the Ladr sequences in Tables 1, 2, and/or 3 and/or the addition or activation of the lncRNA sequences in Tables 4A, 4B and/or 5.

For enhancing pluripotency reprogramming of a somatic cell or differentiation of a pluripotent cell, addition or activation of at least one lncRNA may include one of many known suitable methods. For example, the somatic cell or pluripotent cell may be contacted with (e.g., cultured with) synthetic lncRNAs or in vitro transcribed lncRNA encoding the lncRNA or a fragment thereof. Additional non-limiting examples for increasing the presence of lncRNA in the presence of somatic cell for induced pluripotency reprogramming includes delivery vectors, viral viruses, and chemical synthesis.

Enhancing pluripotency reprogramming of a somatic cell or differentiation of a pluripotent cell may include inhibition or repression of at least one lncRNA may include one of many known suitable methods. For example, the somatic cell or pluripotent cell may be contacted with (e.g., cultured with) an inhibiting nucleic acid of at least one lncRNA. Inhibiting nucleic acid molecules include antisense oligonucleotides, interfering RNA (RNAi) including small interfering RNA (siRNA) and short hairpin RNA (shRNA). Inhibiting nucleic acid molecules used to practice the methods described herein, whether RNA, cDNA, genomic DNA, vectors, viruses or hybrids thereof, can be isolated from a variety of sources, genetically engineered, amplified, and/or expressed/generated recombinantly. If desired, nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000), the entire contents of all of which are herein incorporated by reference).

In some embodiments, inhibitory nucleic acids of the invention are synthesized chemically. Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066; WO/2008/043753 and WO/2008/049085, and the references cited therein, the entire contents of all of which are herein incorporated by reference.

In some embodiments, a method of enhancing pluripotency reprogramming of a somatic human cell includes the addition or activation of at least one human lncRNA selected from Tables 2 and/or 3. In other embodiments, a method of enhancing human pluripotent cell differentiation includes the addition or activation of at least one human lncRNA selected from Tables 4B and/or 5.

In some embodiments, a method for enhancing pluripotency reprogramming of a somatic cell or differentiation of a pluripotent cell, includes inhibition or repression of at least one human lncRNA selected from Tables 4B or 5. In other embodiments, a method of enhancing human pluripotent cell differentiation includes the addition or activation of at least one human lncRNA selected from Tables 2 and/or 3.

It is understood by a person having ordinary skill in the art, that any of the modified chemistries or formats of inhibitory nucleic acids described herein can be combined with each other, and that one, two, three, four, five, or more different types of modifications can be included within the same molecule.

The following Examples are presented for illustrative purposes only, and do not limit the scope or contents of the present application.

Example 1

Single-Cell Transcriptome Analysis of Activated Genes During Reprogramming

Figure 2A:
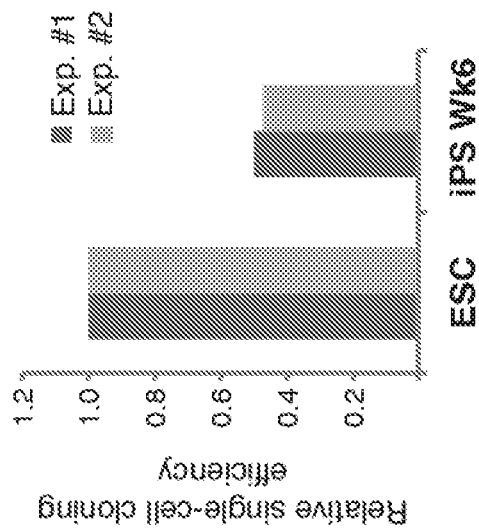
FIGS. 2A, 2B, and 2C show induced pluripotent stem cells as described herein, according to embodiments of the invention.
Figure 2B:
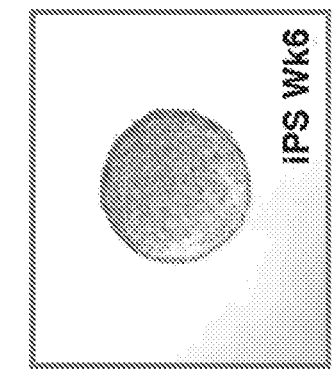
Figure 2C:
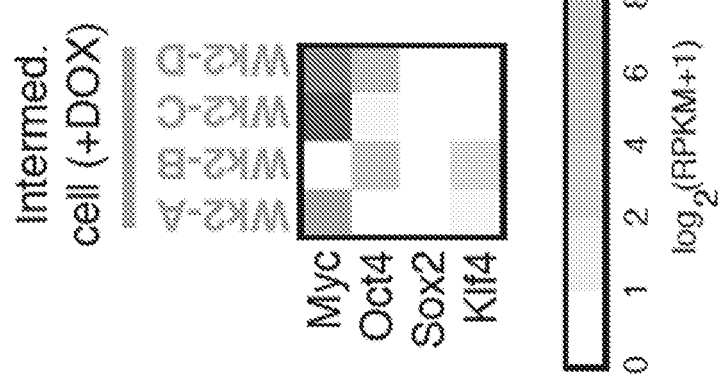
Figure 3:
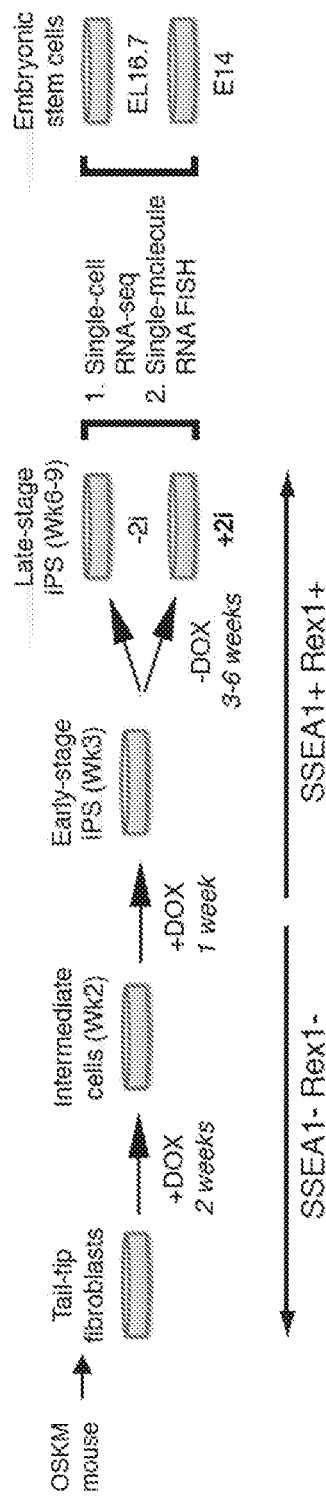
FIG. 3 is a schematic showing induction of pluripotency in tail-tip fibroblasts, according to embodiments of the invention.

In order to characterize the transcriptomes of individual reprogramming cells at defined timepoints, single-cell RNA-sequencing was performed as described (Ramskold et al., 2012, Nat Biotechnol 30, 777-782, the entire contents of which are herein incorporated by reference) using cells from the "reprogrammable" mouse (Carey, B. W. et al., 2010, Nat Methods 7, 56-59, the entire contents of which are herein incorporated by reference). Tail-tip fibroblasts (TTF) from these mice, which harbor doxycycline (dox)-inducible OSKM transgenes (FIG. 2A) were generated, and these cells were cultured in the presence of dox for 3 weeks. ES cell-like colonies that expressed SSEA1 began to appear after 3 weeks, and these early-stage iPS cells were cultured for an additional 3-6 weeks in the absence of dox. Late-stage iPS cells at week 6 (Wk6), which had single-cell cloning efficiencies of ~50% when compared to ES cells (FIG. 2B), were also cultured in 2i conditions to facilitate establishment of the pluripotent ground state (Silva, J. et al., 2008, PLoS Biol 6, e253, the entire contents of which are herein incorporated by reference). Additionally, two different ES cell lines (E14 and EL16.7) were cultured to compare similarities between ES and iPS cell transcriptomes at the single-cell level (FIG. 3).

Figure 4A:
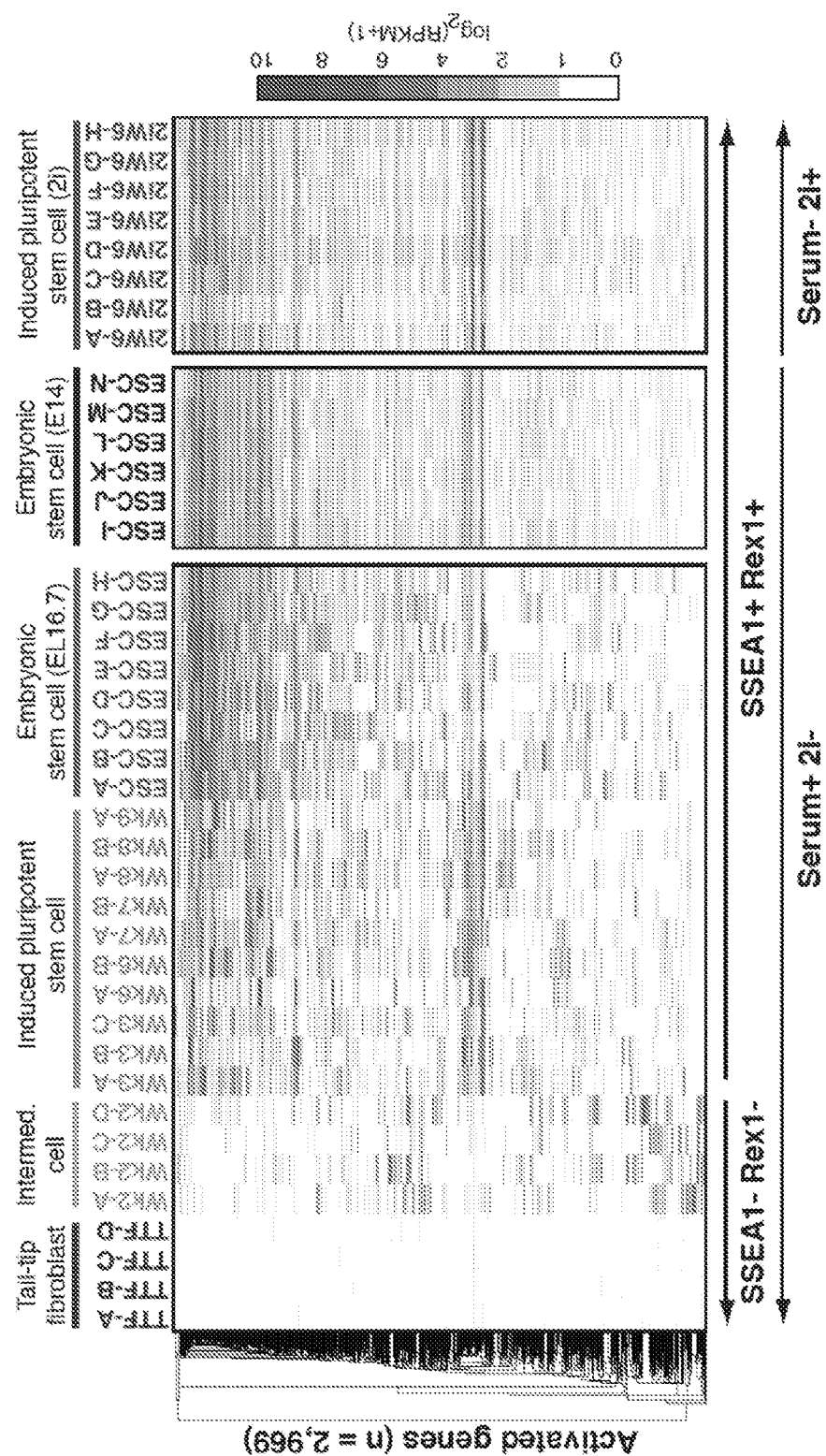
FIG. 4A shows activated genes in tail tip fibroblasts as described herein, according to embodiments of the invention.
Figure 4C:
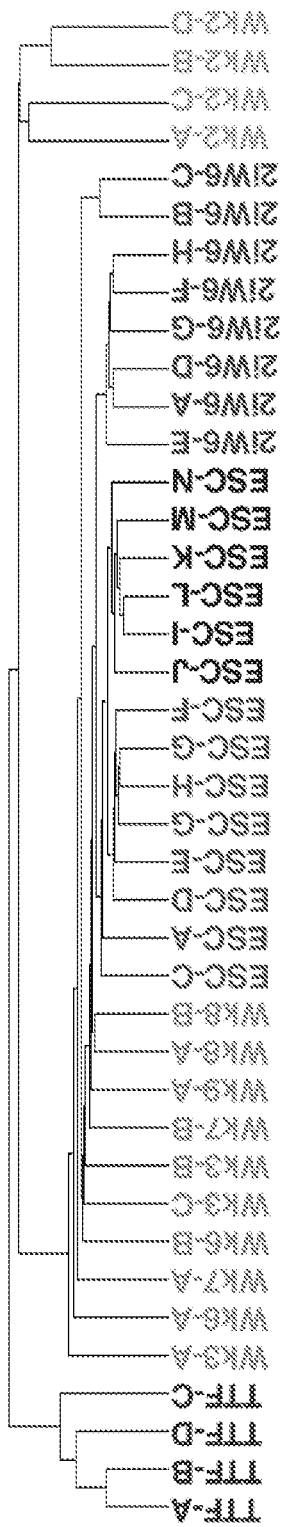
FIGS. 4C-4D show a timeline of induced pluripotency as described herein, according to embodiments of the invention.

Protein-coding genes that were activated during reprogramming and the acquisition of pluripotency were first examined. That is, approximately 3,000 activated genes were expressed at 10 RPKM (reads per kilobase per million mapped reads) (Mortazavi, A. et al., 2008, Nat Methods 5, 621-628, the entire contents of which are herein incorporated by reference) or higher in non-TTF cells, while being off in TTF cells (expressed at less than 1 RPKM) (FIG. 4A). When hierarchical clustering was performed, the cells from both ES lines clustered together, along with the late-stage iPS cells that were cultured in 2i conditions. Both early- and late-stage iPS cells cultured in non-2i conditions clustered together, suggesting different latencies in their reprogramming/remodeling kinetics (Hanna, J. et al., 2009, Nature 462, 595-601, the entire contents of which are herein incorporated by reference). In late-stage iPS cells, imposing 2i conditions pushed their protein-coding transcriptomes (FIG. 4B) to more closely resemble the pluripotent ground state of ES cells (FIG. 4C).

Figure 4D:
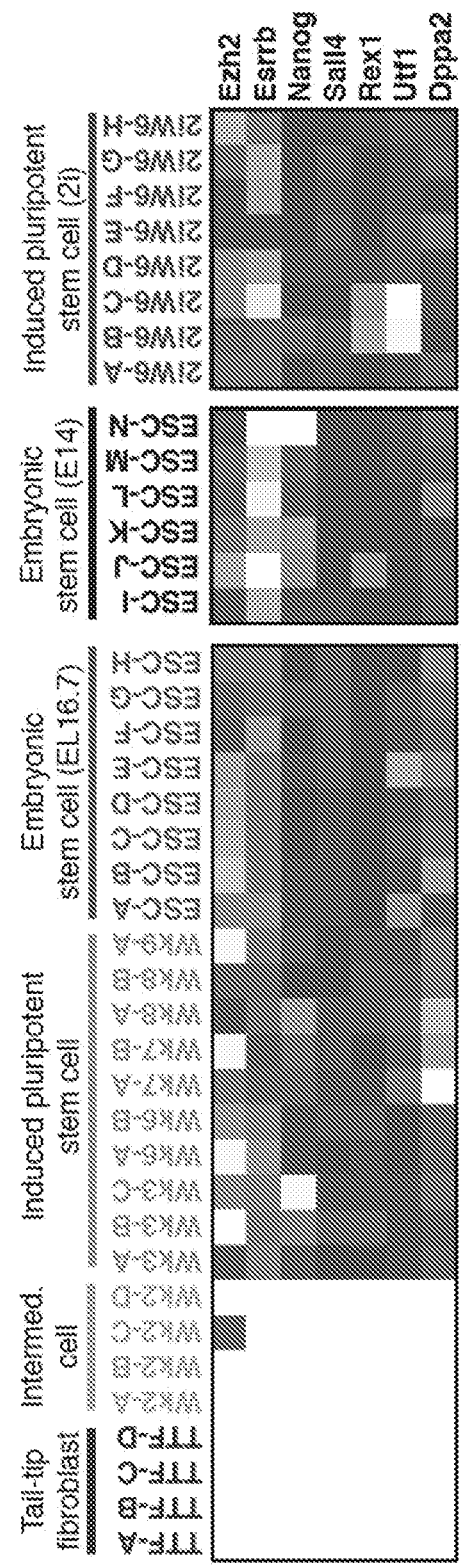
Figure 5A:
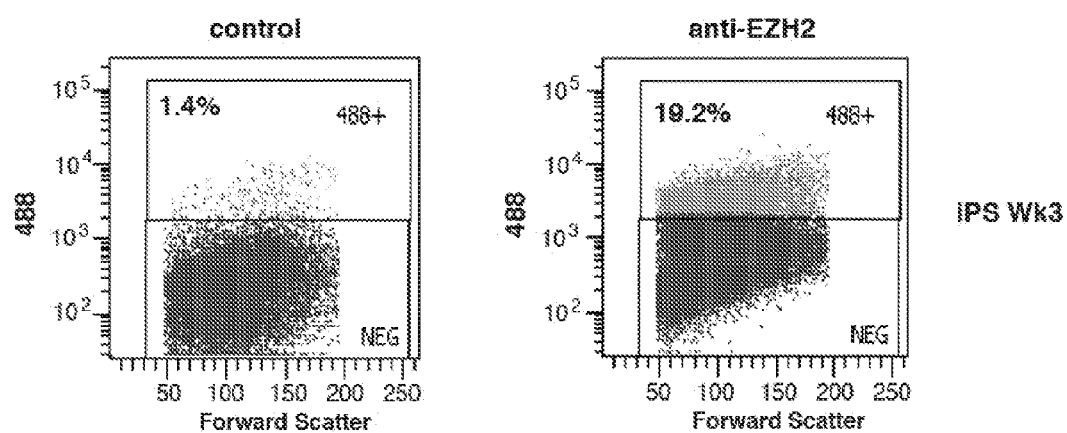
FIGS. 5A, 5B, and 5C each show a forward scatter plot of iPS cells at week 3 (FIG. 5A), week 6 (FIG. 5B), and week 9 (FIG. 5C), according to embodiments of the invention.
Figure 5B:
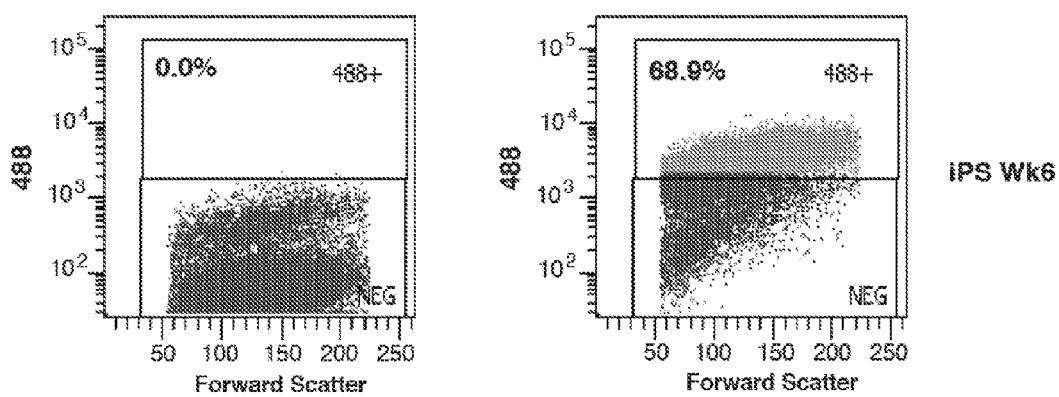
Figure 5C:
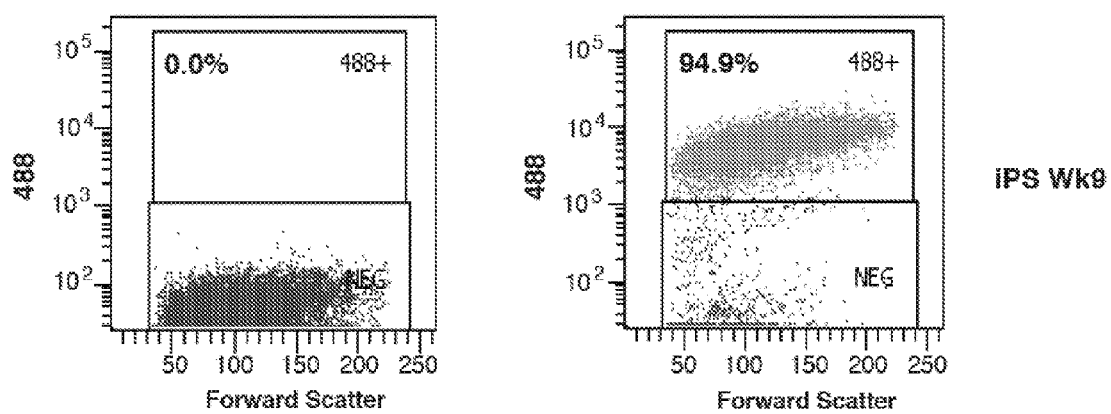

The expression patterns of known pluripotency-related genes that are widely used as faithful predictors of proper iPS cell reprogramming were next examined (Buganim, Y. et al., 2012, Cell 150, 1209-1222, the entire contents of which are herein incorporated by reference). It was found that the genes Esrrb, Utf1, Lin28, and Dppa2 were all expressed starting at week 3 (Wk3) in this reprogramming timecourse, as well as Nanog and Rex1. However, Polycomb histone methyltransferase Ezh2, which physically binds to numerous lncRNAs according to (Guttman, M. et al., 2011, Nature 477, 295-300; Zhao, J. et al., 2010, Mol Cell 40, 939-953, the entire contents of which are herein incorporated by reference), was heterogeneously expressed in both early- and late-stage iPS cells (FIG. 4D and FIGS. 5A, 5B, 5C). This heterogeneity in Ezh2 expression was attenuated under 2i conditions (FIG. 4D).

Example 2

Visualizing Single-Cell Transcriptome Dynamics Using the Self Organizing Map (SOM)

Figure 6:
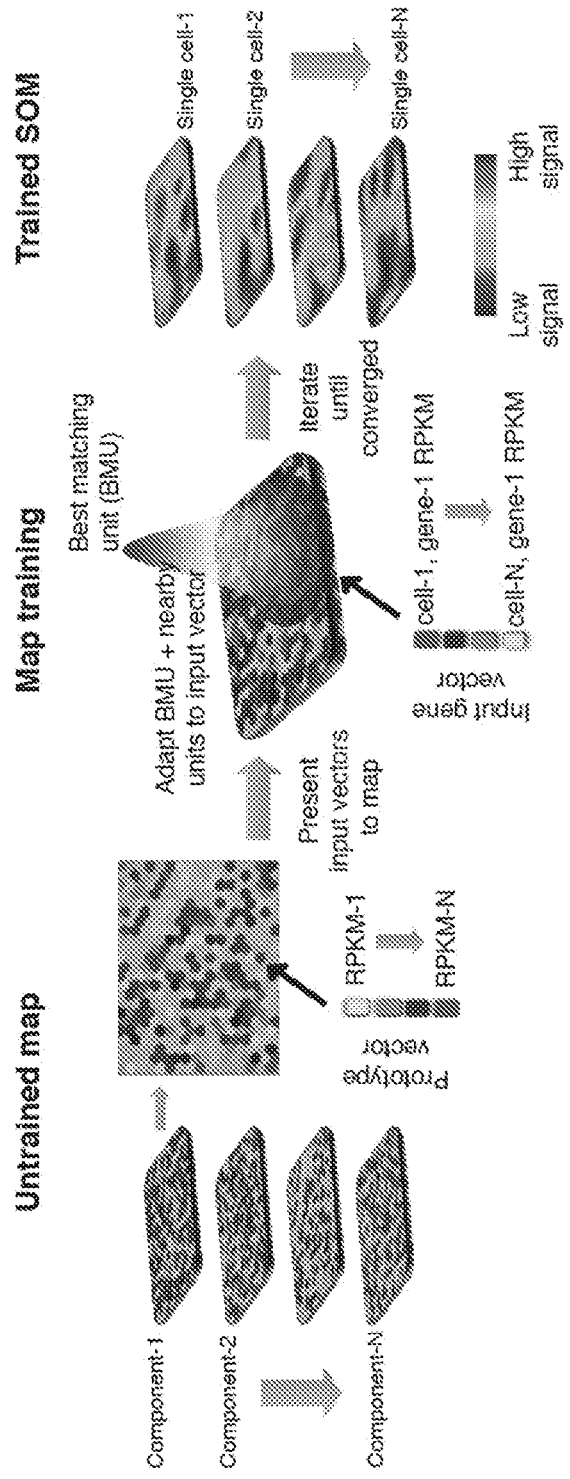
FIG. 6 is a self-organizing map to identify dynamic changes in the single-cell transcriptomes of reprogramming cells to facilitate visualization of gene sets that are coordinately expressed during the reprogramming timecourse, according to embodiments of the invention.
Figure 7A:
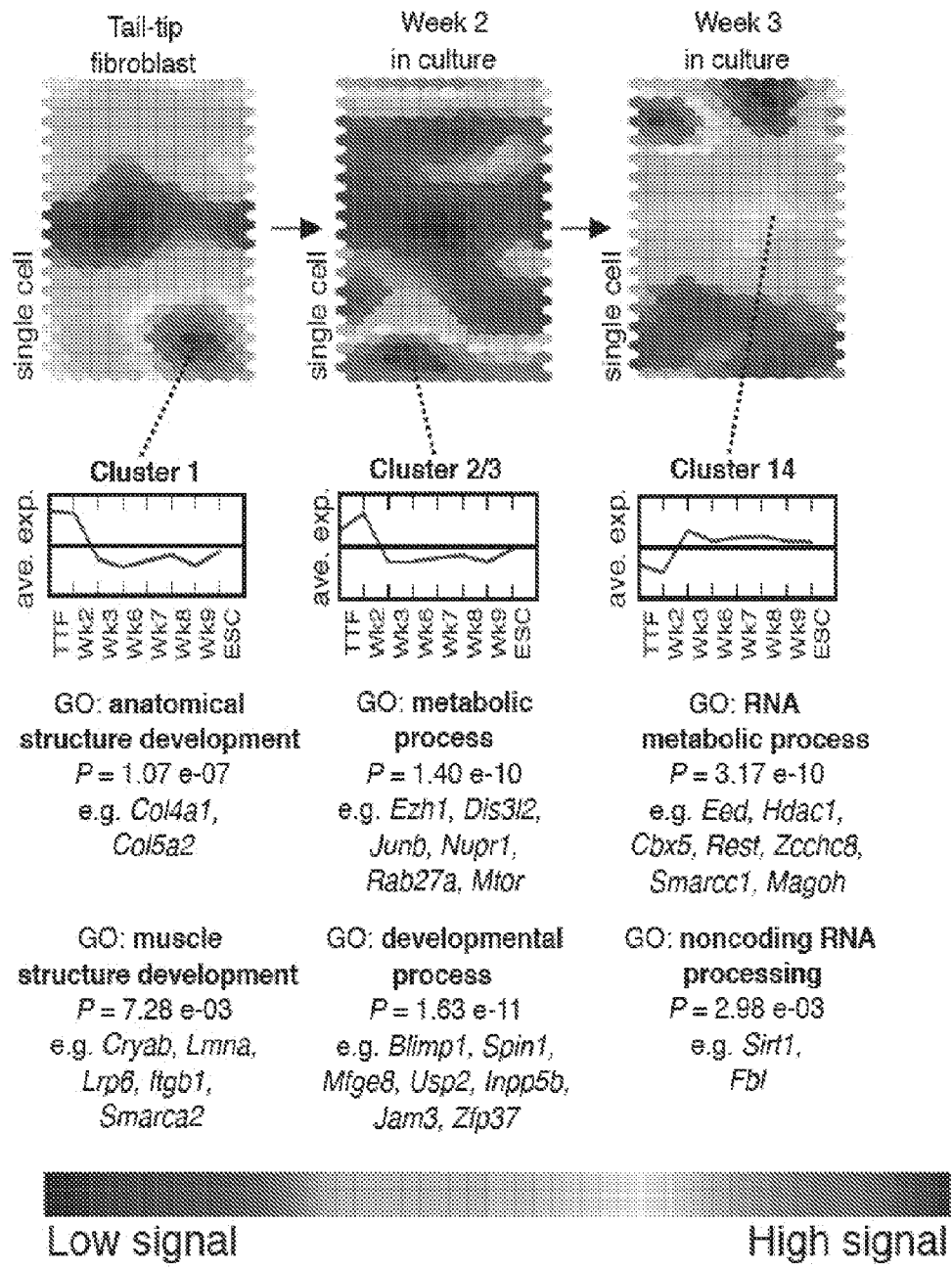
FIG. 7A is an analysis of tail tip fibroblasts (TTFs) that strongly express genes involved in body axis anatomy and development of muscle, as described herein. Intermediate reprogramming cells at week 2 (Wk2) expressed numerous genes that are required for proper germ cell development and fertility, including Blimp1. By week 3 (Wk3) of reprogramming, individual cells began to express genes that are involved in RNA metabolism and noncoding RNA processing Late-stage iPS cells at week 6 (Wk6) strongly expressed hundreds of pseudogenes which can be processed into small regulatory RNAs in oocytes. Late-stage iPS cells at week 8 (Wk8) expressed known pluripotency factors at high levels, including Oct4, Nanog, Esrrb, and Sall4, but did not exhibit full activation of germ cell regulatory genes such as Stella and Prdm14, which are highly expressed in ES cells, according to embodiments of the invention.
Figure 7A:
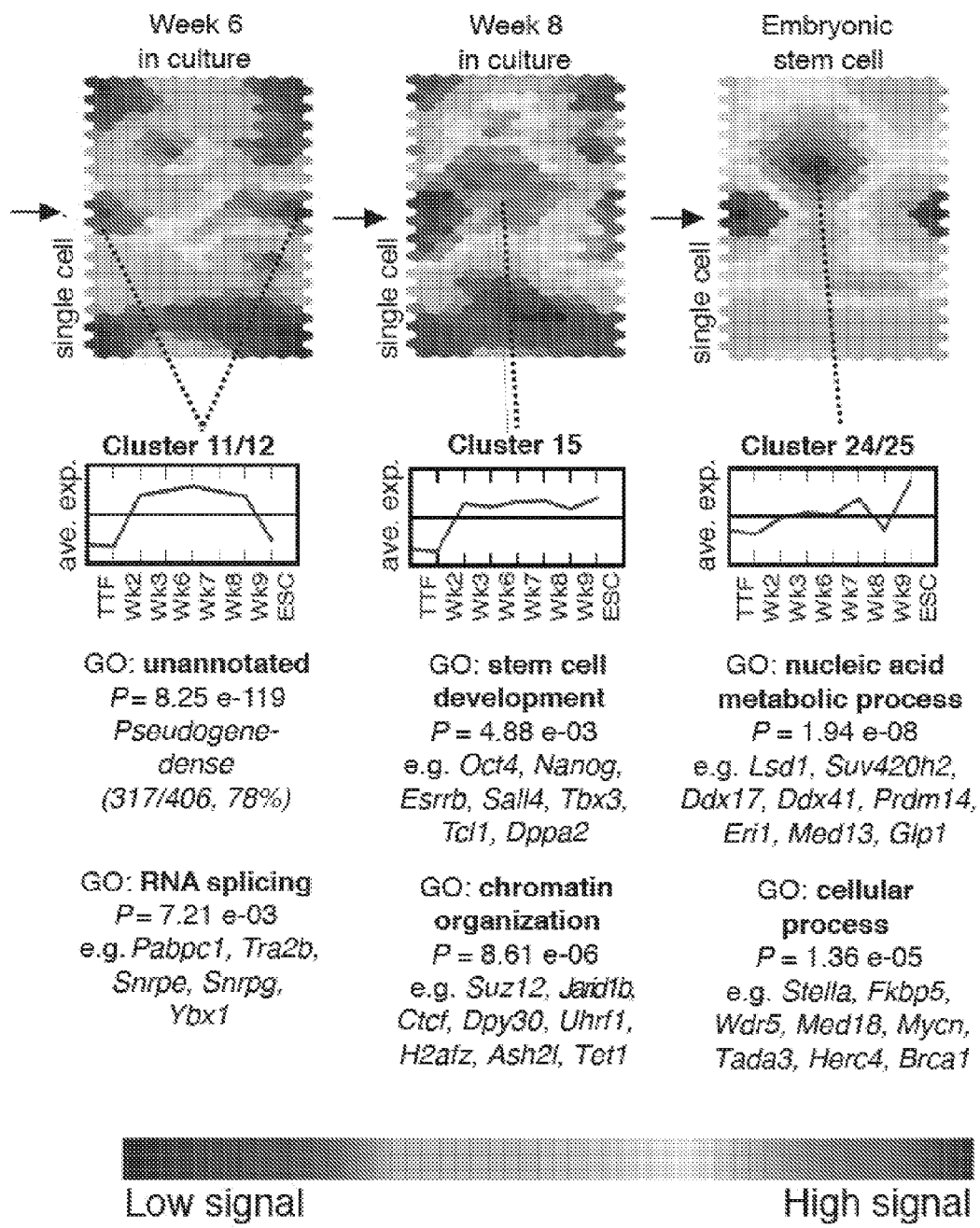

In order identify dynamic changes in the single-cell transcriptomes of reprogramming cells, a self-organizing map (SOM) (Kohonen, T., 2013, Neural Netw 37, 52-65, the entire contents of which are herein incorporated by reference) was generated, which facilitates visualization of gene sets that are coordinately expressed during the reprogramming timecourse (FIGS. 6 and 7A). The 5,000 protein-coding and lncRNA genes were used with the greatest variance among the single-cell RNA-seq data to train the SOM. The results of FIG. 7A show that TTFs strongly express genes involved in body axis anatomy and development of muscle. Notably, intermediate reprogramming cells at week 2 (Wk2) expressed numerous genes that are required for proper germ cell development and fertility, including Blimp1 (Ohinata, Y. et al., 2005, Nature 436, 207-213, the entire contents of which are herein incorporated by reference), Spin1, Mfge8, Usp2, Inpp5b, Jam3, and Zfp37 (FIGS. 7A-7B) (Eppig, J. T. et al., 2012, Nucleic Acids Res 40, D881-886, the entire contents of which are herein incorporated by reference). These results suggest that somatic cell reprogramming takes advantage of existing developmental programs in germ cells, where global reprogramming of the epigenome occurs as part of normal embryonic development (Hayashi, K. et al., 2009, Cell Stem Cell 4, 493-498, the entire contents of which are herein incorporated by reference).

By week 3 (Wk3) of reprogramming, individual cells began to express genes that are involved in RNA metabolism and noncoding RNA processing (FIG. 7A). Surprisingly, late-stage iPS cells at Wk6 strongly expressed hundreds of pseudogenes (FIG. 7A), which can be processed into small regulatory RNAs in oocytes (Tam, O. H. et al., 2008, Nature 453, 534-538, the entire contents of which are herein incorporated by reference). Late-stage iPS cells at week 8 (Wk8) expressed known pluripotency factors at high levels, including Oct4, Nanog, Esrrb, and Sall4, but they failed to exhibit full activation of germ cell regulatory genes such as Stella and Prdm14, which are highly expressed in ES cells (FIG. 7A). These results indicate that while the transcriptional landscape of late-stage iPS cells are quite similar to ES cells, there are also notable differences in expression of both protein-coding and noncoding genes at the single-cell level.

Example 3

Germ Cell-Related Genes are Expressed in Late-Stage iPS Cells

Figure 8:
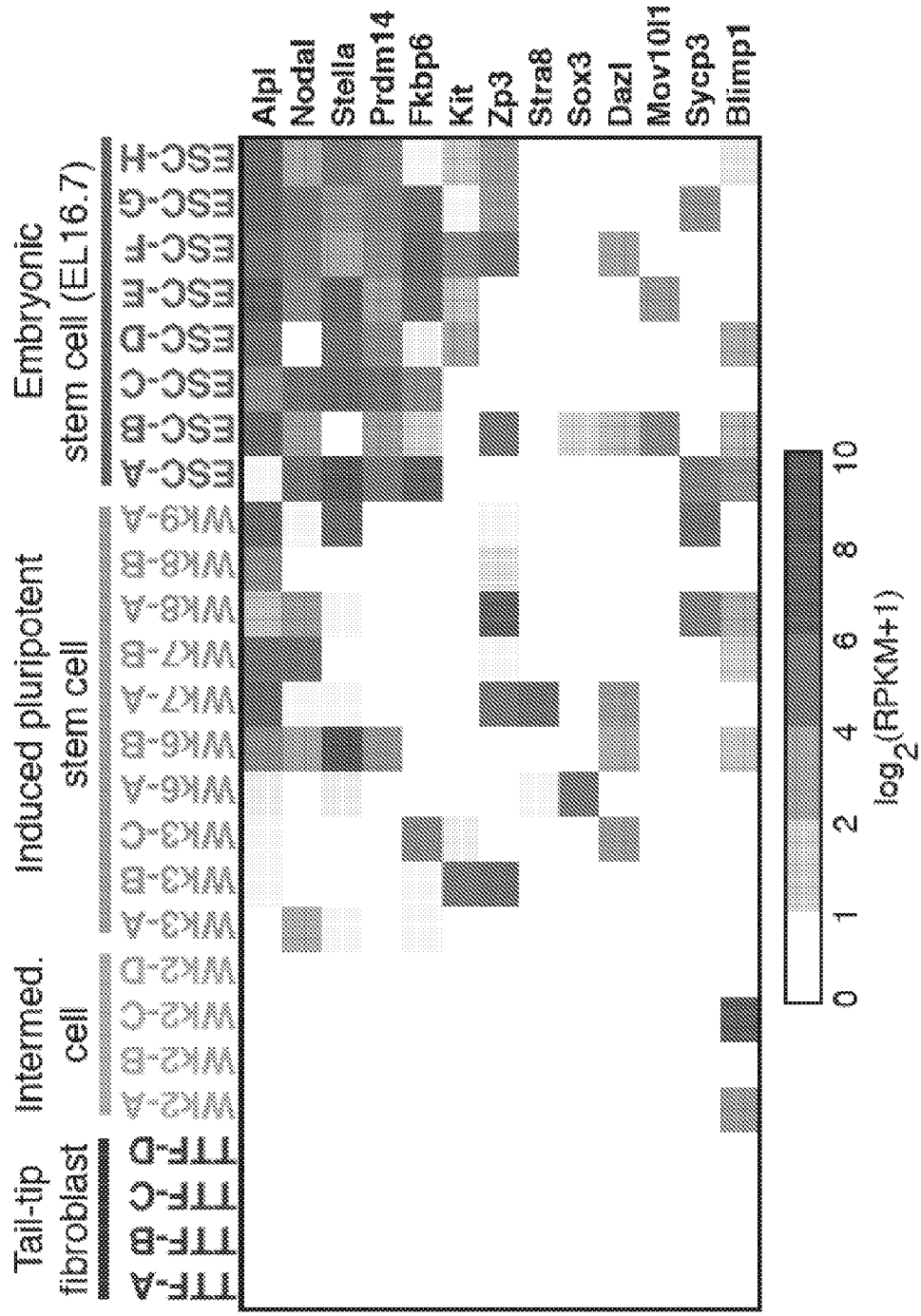
FIG. 8 shows the expression pattern of germ cell-related genes determined by log 2(RPKM+1) (RPKM=reads per kilobase per million) using small molecule fluorescent in situ hybridization (smFISH) showing that Stella and Prdm14 appear to be heterogeneously expressed during the reprogramming timecourse, as described herein.
Figure 9:
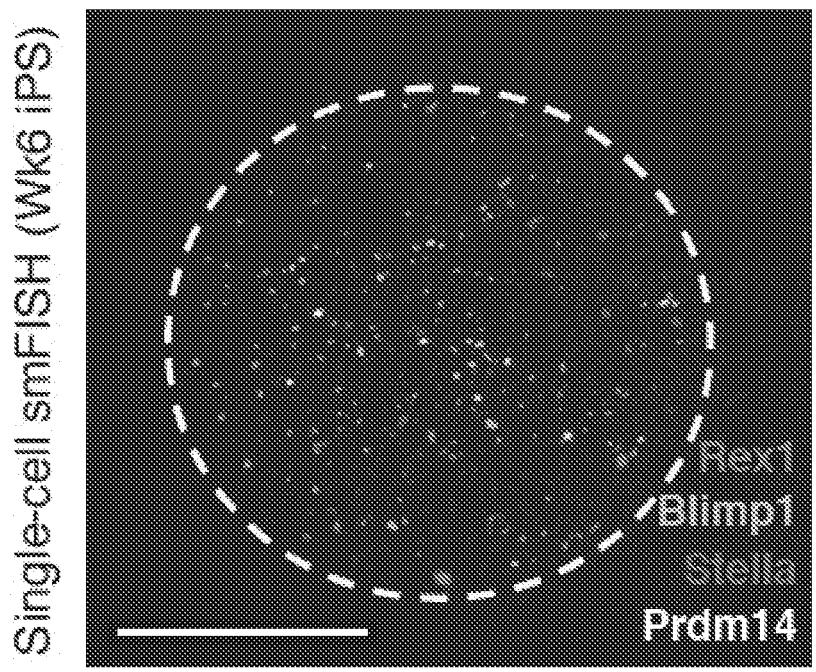
FIG. 9 is a fluorescence image of a single cell at week 6 (wk6) of iPS cell reprogramming using 4-color smFISH to characterize the full distribution of Stella, Prdm14, Blimp1, Rex1, Oct4, and Sox2 RNAs in hundreds of late-stage iPS cells (n=303), as described herein.
Figure 10A:
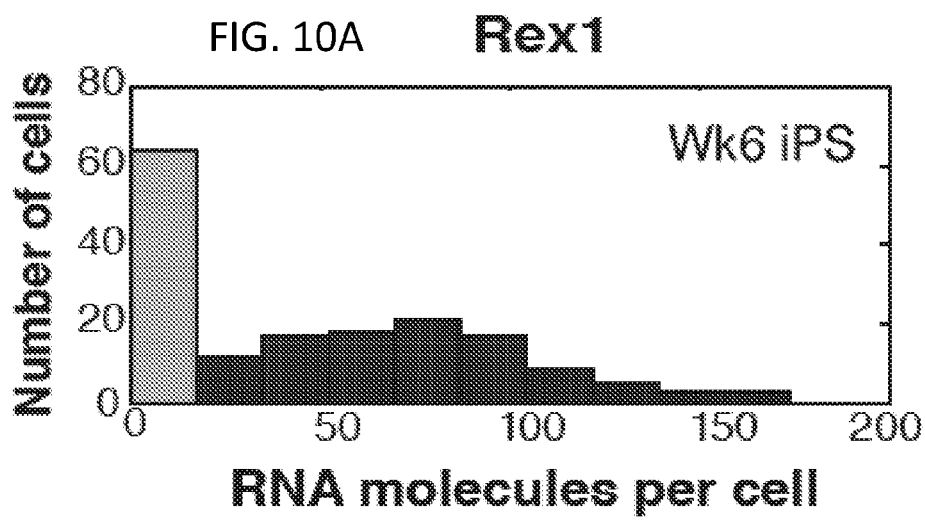
Figure 10B:
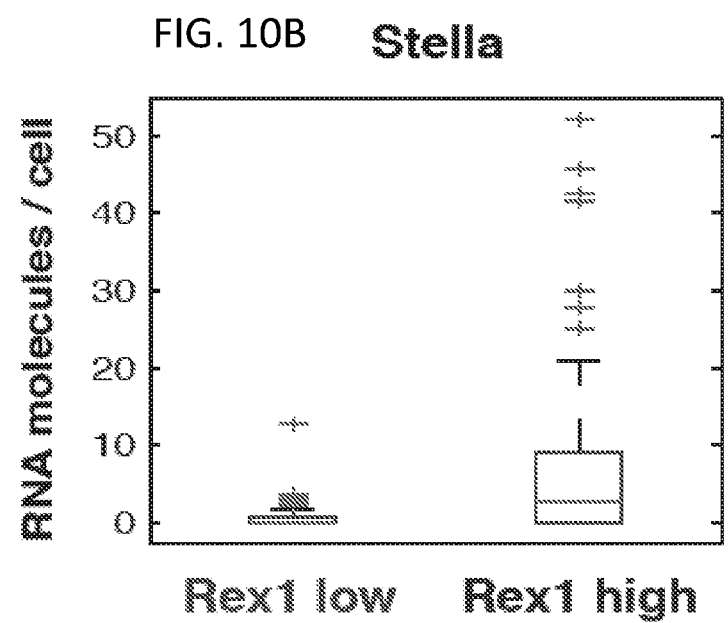

In order to validate the expression patterns of germ cell-related genes in the single-cell RNA-seq data of FIG. 8, smFISH as described in (Raj, A. et al., 2008, Nat Methods 5, 877-879, the entire contents of which are herein incorporated by reference) was used as an orthogonal, amplification-independent method to characterize the full distribution of Stella, Prdm14, Blimp1, Rex1, Oct4, and Sox2 RNAs in hundreds of late-stage iPS cells (n=303) at Wk6 (FIG. 9). The results of this amplification methods, Stella and Prdm14 appeared to be heterogeneously expressed during the reprogramming timecourse and were first detected at Wk6, whereas ES cells expressed these genes more uniformly (FIG. 8). Using 4-color smFISH, it was observed that Stella, Prdm14, and Blimp1 levels were all higher in individual iPS cells that also expressed greater levels of Rex1, while cells with low Rex1 expression generally did not express these genes (FIGS. 10A, 10B, 10C, 10D). These results suggest that late-stage iPS cells with high levels of Rex1 may exhibit more germ cell character.

Figure 11A:
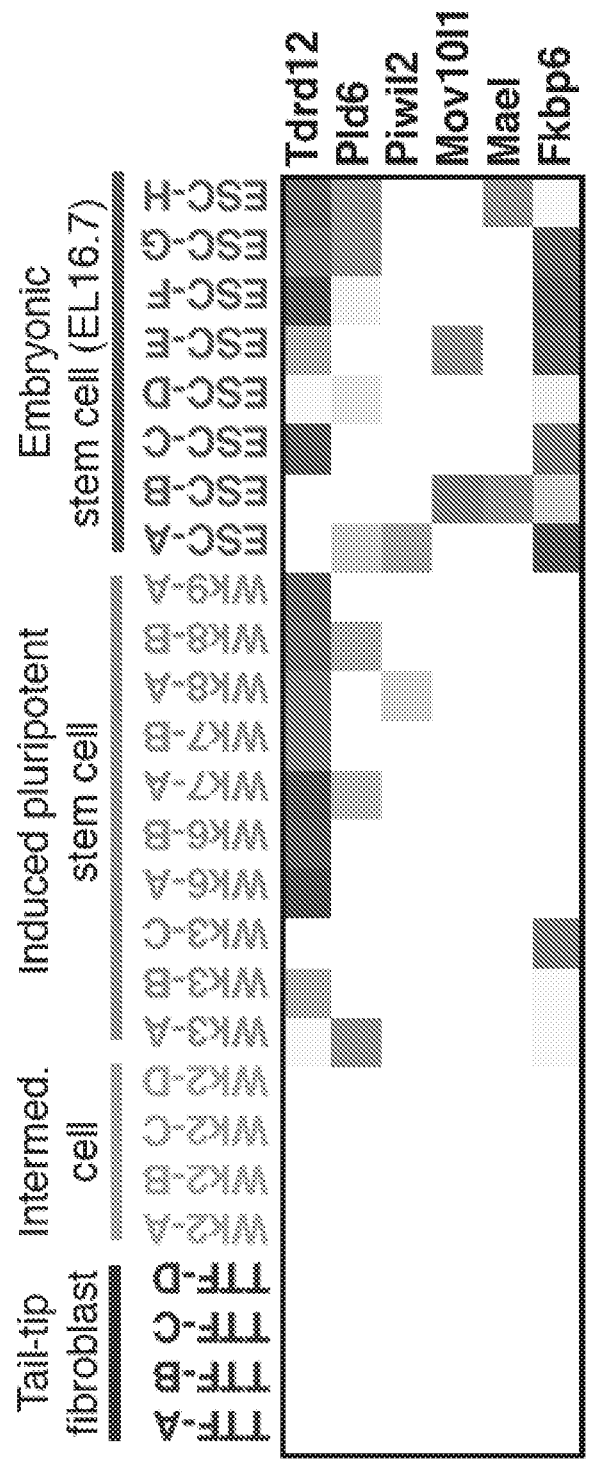
FIG. 11A shows the expression pattern of germ cell-related genes using small molecule fluorescent in situ hybridization (smFISH) showing that late-stage iPS cells began to express Piwil2 which associates with Piwi-interacting RNAs (piRNAs), as described herein.
Figure 11B:
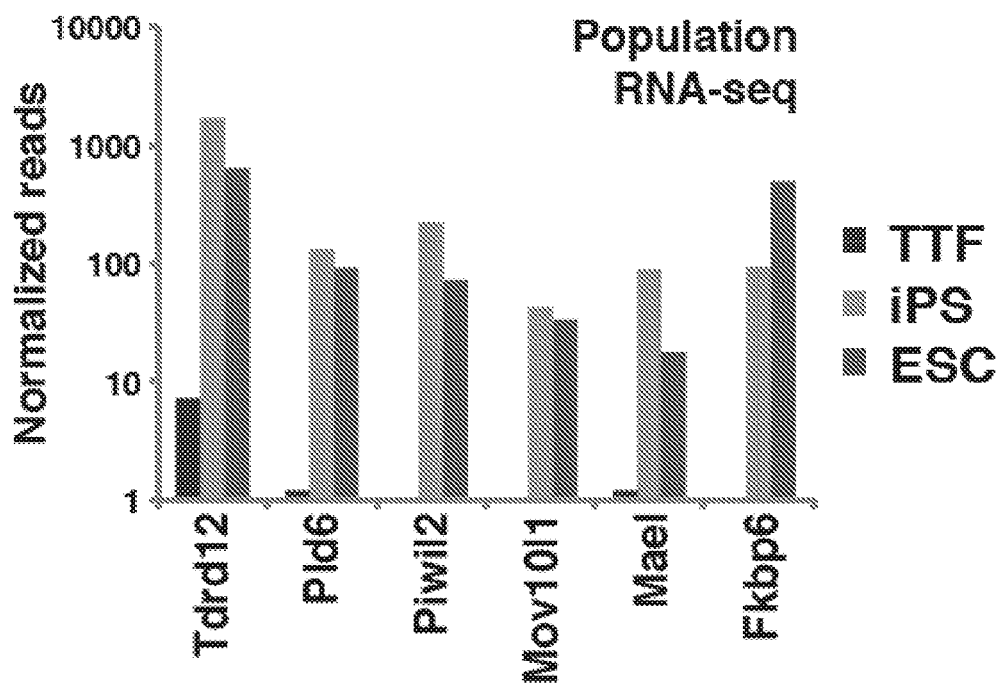
FIG. 11B is a graph showing that at the population level, iPS cells expressed genes involved in piRNA function and biogenesis, as described herein.
Figure 11C:
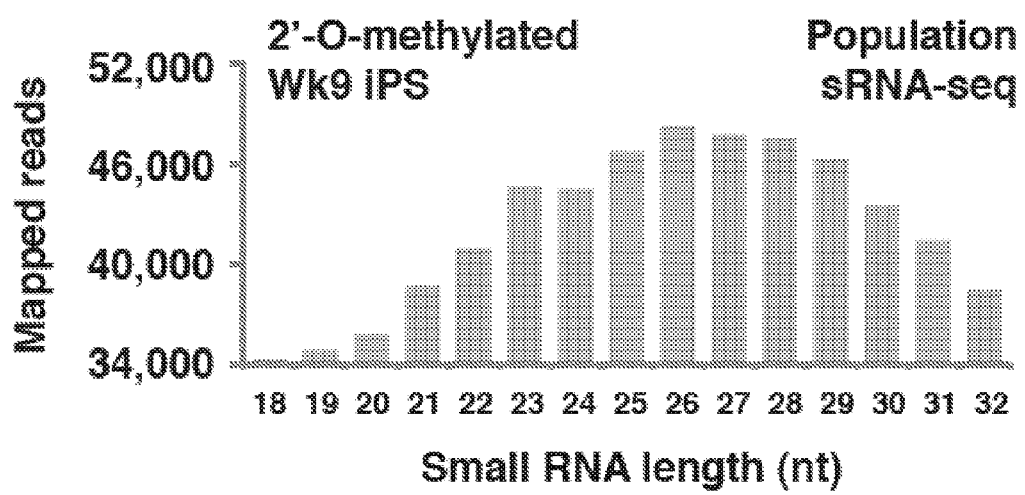
FIG. 11C is a graph showing that the 2'-O-methylated small RNAs that were cloned and sequenced from iPS cells exhibited a characteristic size distribution peak of 26 nucleotides (nt), as described herein.
Figure 11D:
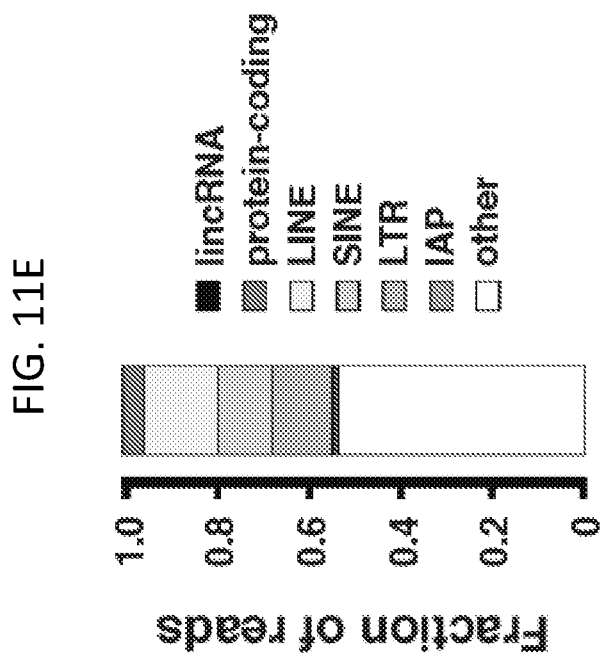
FIG. 11D is a graph showing that of the 2'-O-methylated small RNAs sequenced in FIG. 11C, 40% had a 5'U, indicative of primary piRNAs in the germline, as described herein.
Figure 11E:
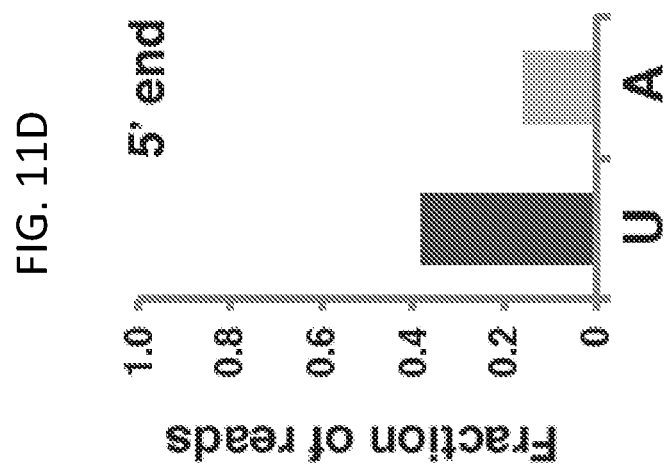
FIG. 11E is a graph showing that 40% of the 2'-O-methylated small RNAs of FIG. 11C mapped to retrotransposons, as described herein.

Additionally, late-stage iPS cells began to express Piwi12 (FIG. 11A), which associates with Piwi-interacting RNAs (piRNAs) in the germline to epigenetically silence retrotransposons (Aravin, A. A. et al., 2007, Science 316, 744-747, the entire contents of which are herein incorporated by reference). At the population level, iPS cells expressed genes involved in piRNA function and biogenesis (FIG. 11B). The 2'-O-methylated small RNAs were cloned and sequenced (Li, X. Z. et al., 2013, Mol Cell 50, 67-81, the contents of which are herein incorporated by reference) from iPS cells, which exhibited a characteristic size distribution peak of 26 nt (FIG. 11C), analogous to Piwil2-associated piRNAs (Aravin, A. A. et al., 2008, Mol Cell 31, 785-799, the entire contents of which are herein incorporated by reference). The sequencing showed that approximately 40% of 2'-O-methylated small RNAs had a 5'U (FIG. 11D), reminiscent of primary piRNAs in the germline (Luteijn, M. J. et al., 2013, Nat Rev Genet 14, 523-534, the entire contents of which are herein incorporated by reference). Moreover, approximately 40% of small RNAs mapped to retrotransposons (FIG. 11E). Taken together with a recent study in human iPS cells (Marchetto, M. C. et al., 2013, Nature 503, 525-529, the entire contents of which are herein incorporated by reference), the results suggest that piRNAs are activated during epigenetic reprogramming.

Example 4

Long Noncoding RNAs Activated During Reprogramming (Ladr)

Figure 12:
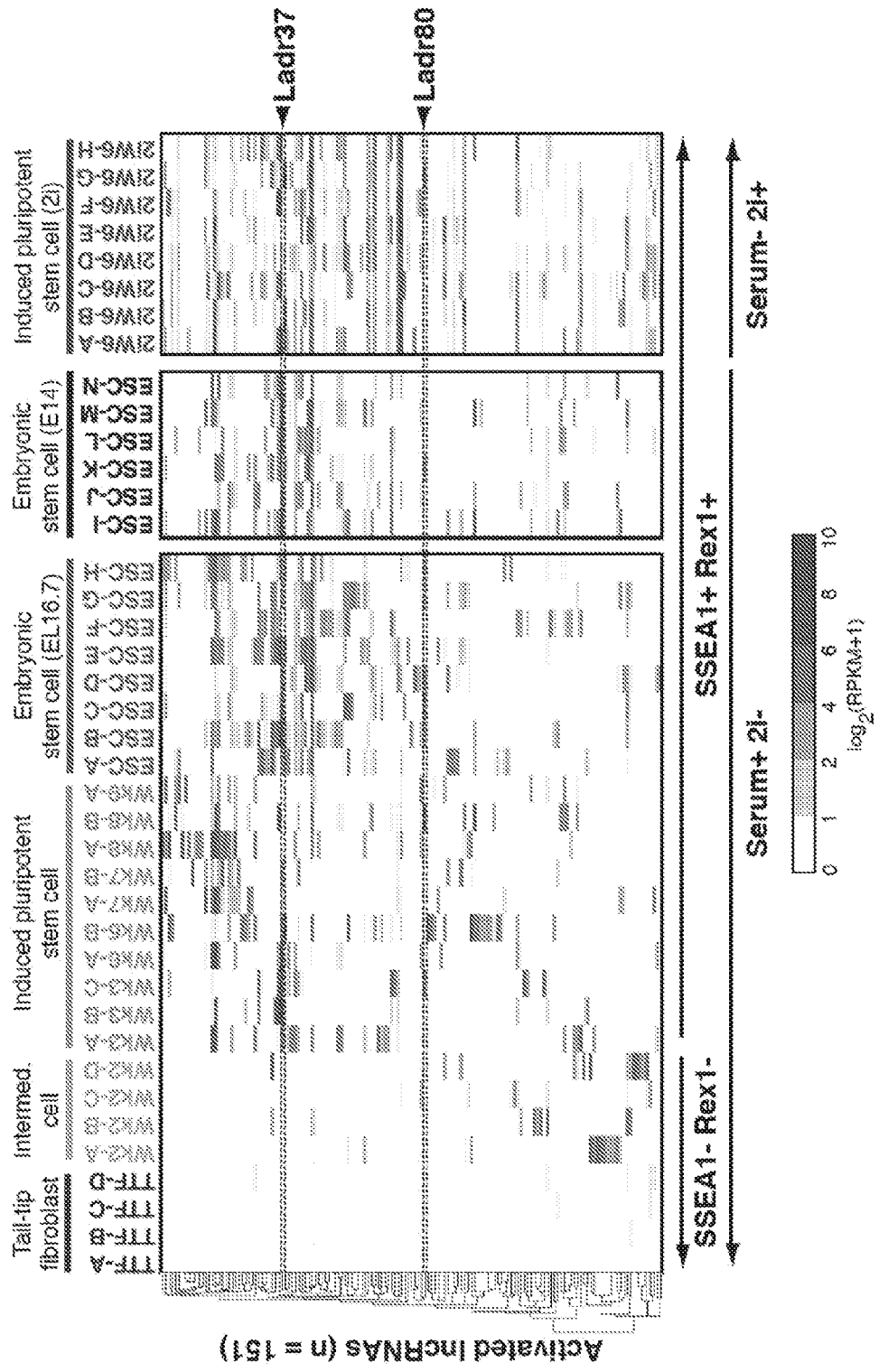
FIG. 12 shows long noncoding RNAs (lncRNAs) that are activated during reprogramming (Ladr), according to embodiments of the invention.
Figure 13A:
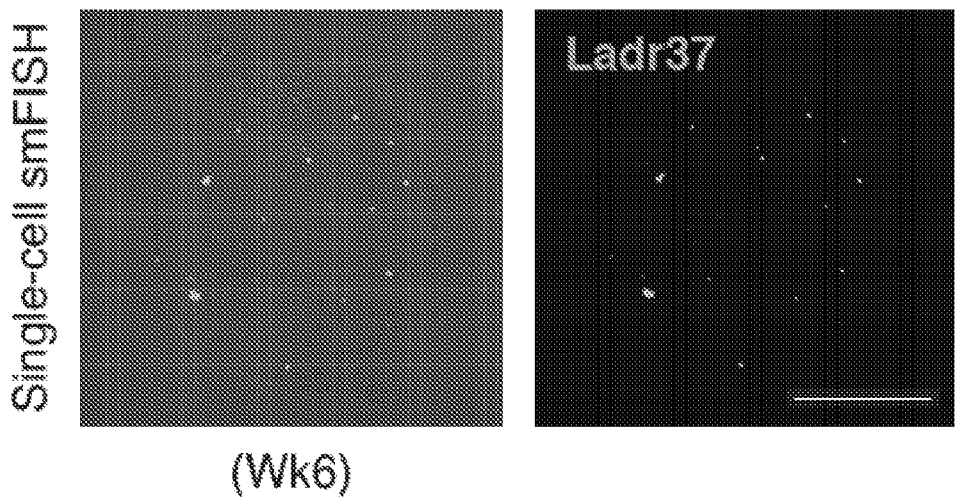
FIG. 13A is a fluorescent image of a single cell at week 6 (Wk6) of iPS cell reprogramming using smFISH, with Ladr37 probe, as described herein.
Figure 13B:
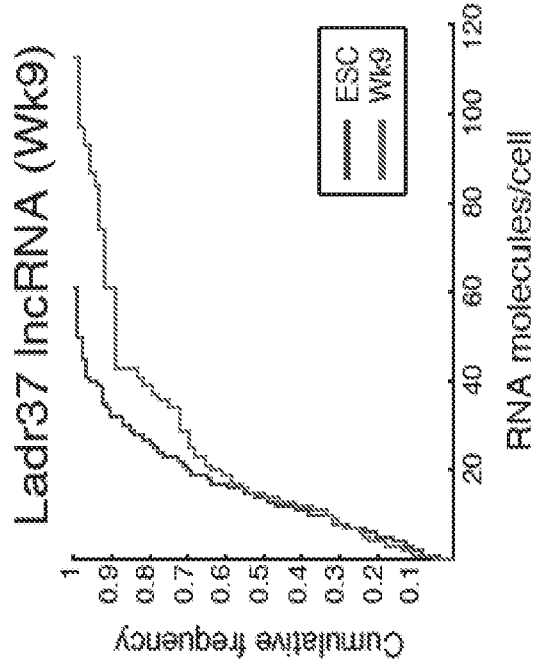
FIGS. 13B and 13C are graphs of cumulative frequency of Ladr37 lncRNAs at week 6 (Wk6) (FIG. 13B) and week 9 (Wk9) (FIG. 13C) compared with ESC (embryonic stem cells), as described herein.
Figure 13C:
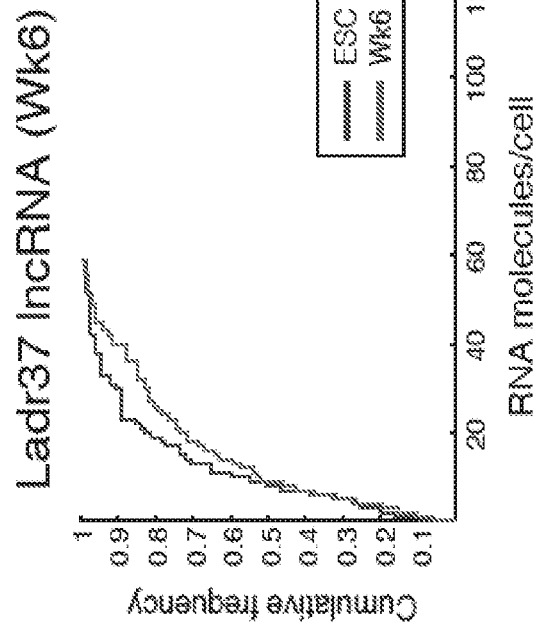
Figure 14A:
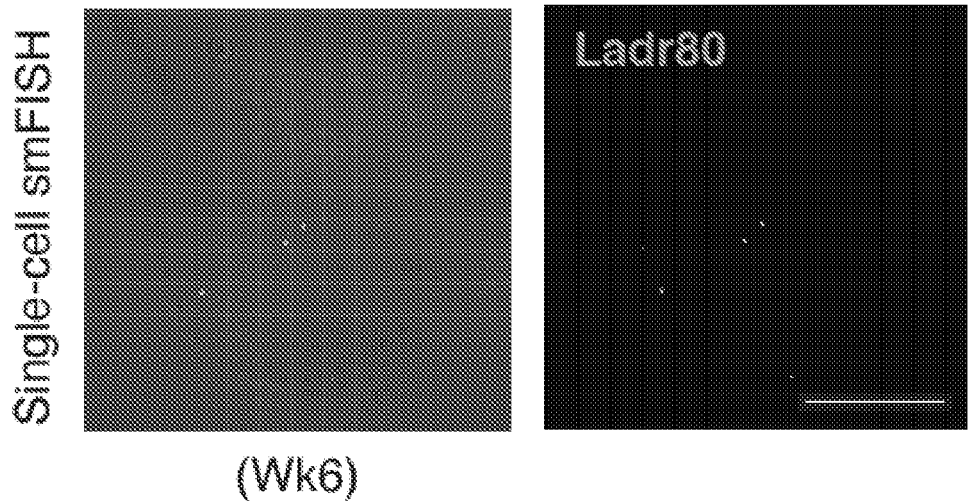
FIG. 14A is a fluorescent image of a single cell at week 6 (Wk6) of iPS cell reprogramming using smFISH, with Ladr80 probe, as described herein.

The changes in the lncRNA transcriptome during reprogramming were examined. Similar to the analysis of protein-coding genes, the focus was on activated lncRNAs (FIG. 1; Tables 1 and 3) that were expressed at 10 RPKM or higher in non-TTF cells, while being repressed in TTFs (below 1 RPKM). The results showed that approximately 150 lncRNAs were activated during the acquisition of pluripotency, and some lncRNAs showed apparent heterogeneity in their expression patterns, even in 2i conditions (FIG. 12). To validate these observations for specific lncRNAs, smFISH was used to characterize the expression patterns of 3 Polycomb-associated lncRNAs (FIGS. 13A, 13B, 13C, 14A, 14B, 14C) in hundreds of cells (n=351). Ladr37 was strongly expressed in both iPS and ES cells, and Ladr80 was weakly expressed in both cell types (FIG. 12 and FIGS. 13B, 13C, 14B, 14C). The distributions of Ladr80 expression in late-stage iPS cells at Wk6 and Wk9 were indistinguishable from ES cells, but Ladr37 expression was aberrantly high in a subset of Wk6 iPS cells relative to ES cells (FIGS. 13B, 13C, 14B, 14C). Also, a subset of Wk9 iPS cells expressed even higher levels of Lad37 (61-113 lncRNA molecules/cell) relative to ES cells (median: 14 lncRNA molecules/cell) (FIGS. 13B, 13C, 14B, 14C), revealing a broad range of heterogeneity in Ladr37 expression, even in late-stage iPS cells.

Example 5

Polycomb-Associated Ladr lncRNAs Repress Developmental Genes in iPS Cells

Figure 15A:
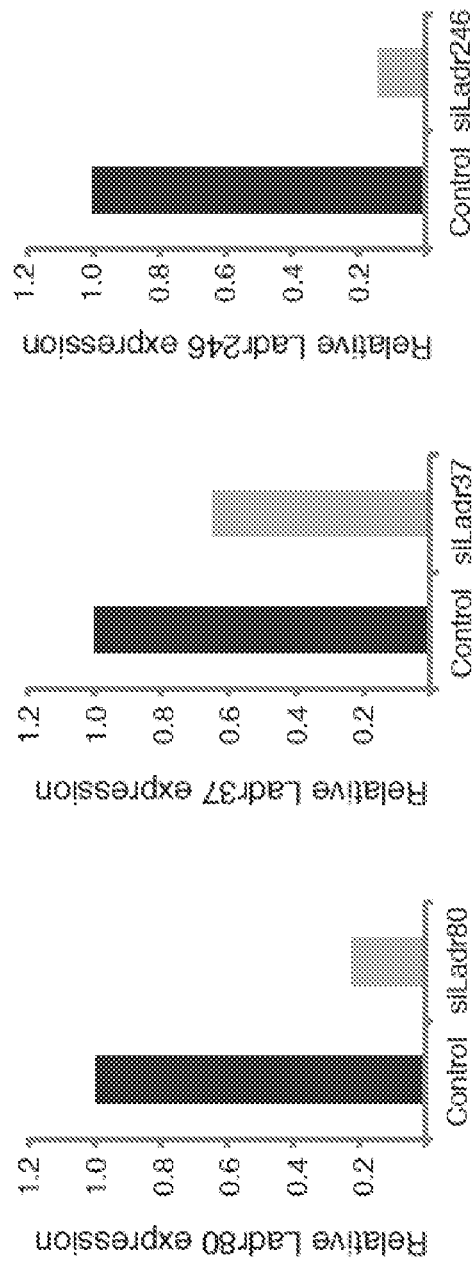
FIG. 15A shows graphs measuring relative expression of Ladr80, Ladr37, and Ladr246 compared to controls, in late stage iPS cells in the presence or absence (control) of Ladr80 siRNA, Ladr37 siRNA, or Ladr246 siRNA, as indicated, as described herein.
Figure 15B:
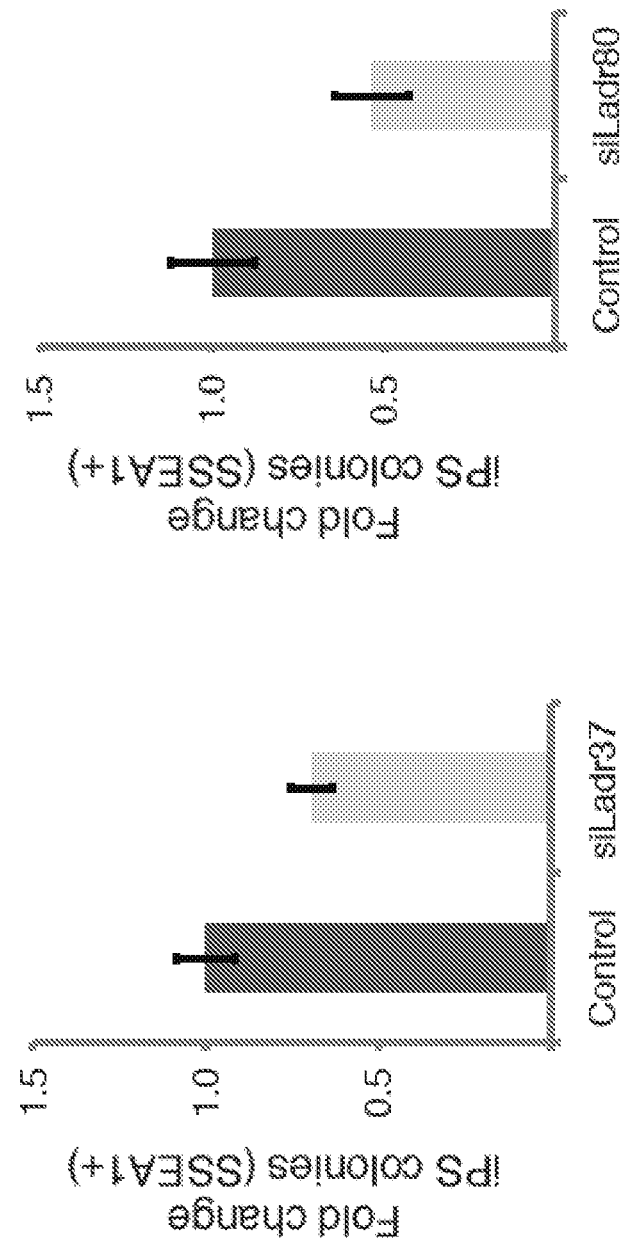
FIG. 15B shows graphs measuring fold change of reprogramming efficiencies in the presence or absence (control) of Ladr37 siRNA or Ladr80 siRNA, as indicated, as described herein.

In order to examine the functional roles of Ladr80 and Ladr37, a pool of 2-4 small interfering RNAs (siRNAs) per lncRNA were used to knock down their expression levels in late-stage iPS cells at Wk9 (FIG. 15A). While knockdown of Ladr80 or Ladr37 had modest effects on reprogramming efficiencies (FIG. 15B), Ladr80 knockdown resulted in the significant upregulation of muscle-related genes in iPS cells.

Figure 16A:
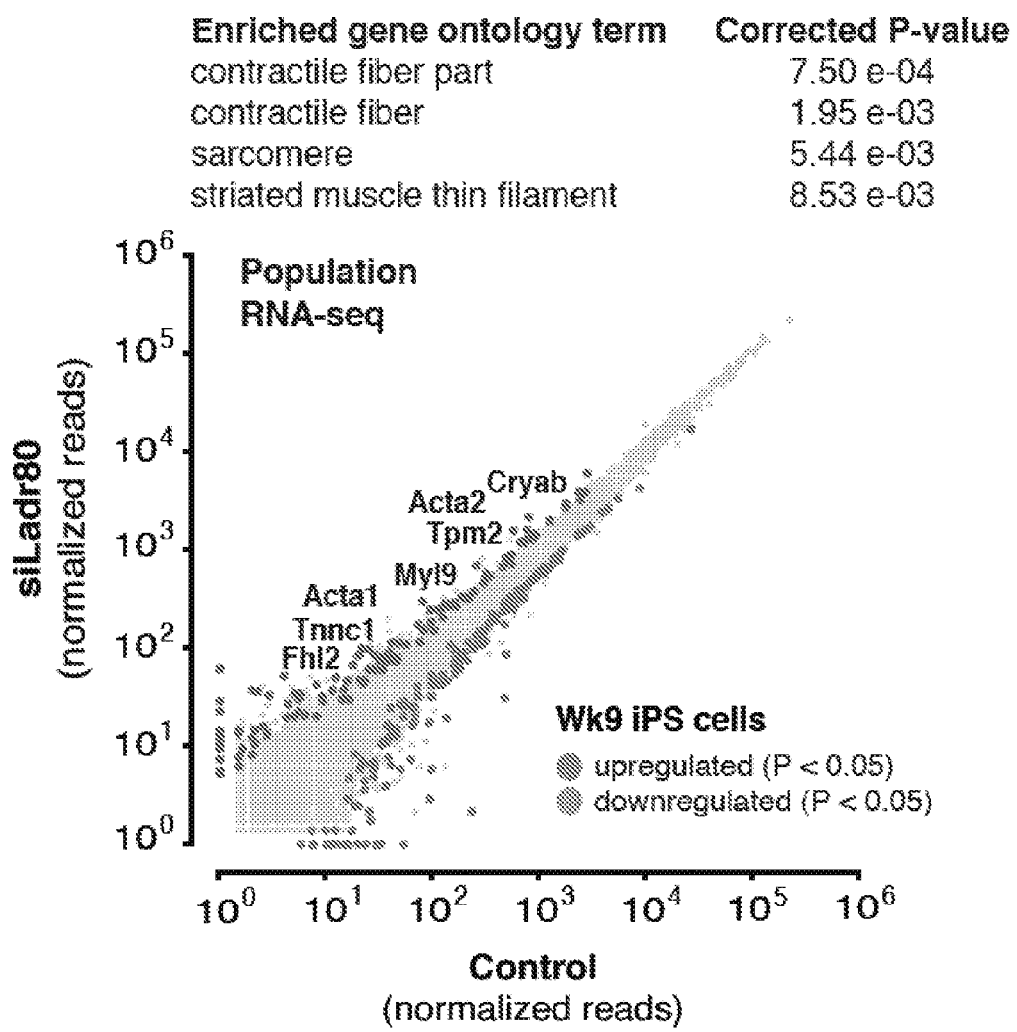
FIG. 16A shows differential expression analysis of significantly upregulated or downregulated genes in iPS cells in the presence (siLadr80) or absence (control) of Ladr80 siRNA, as determined by population level RNA-seq, and gene ontology (GO) analysis for significantly enriched GO terms in upregulated genes, as described herein.
Figure 16B:
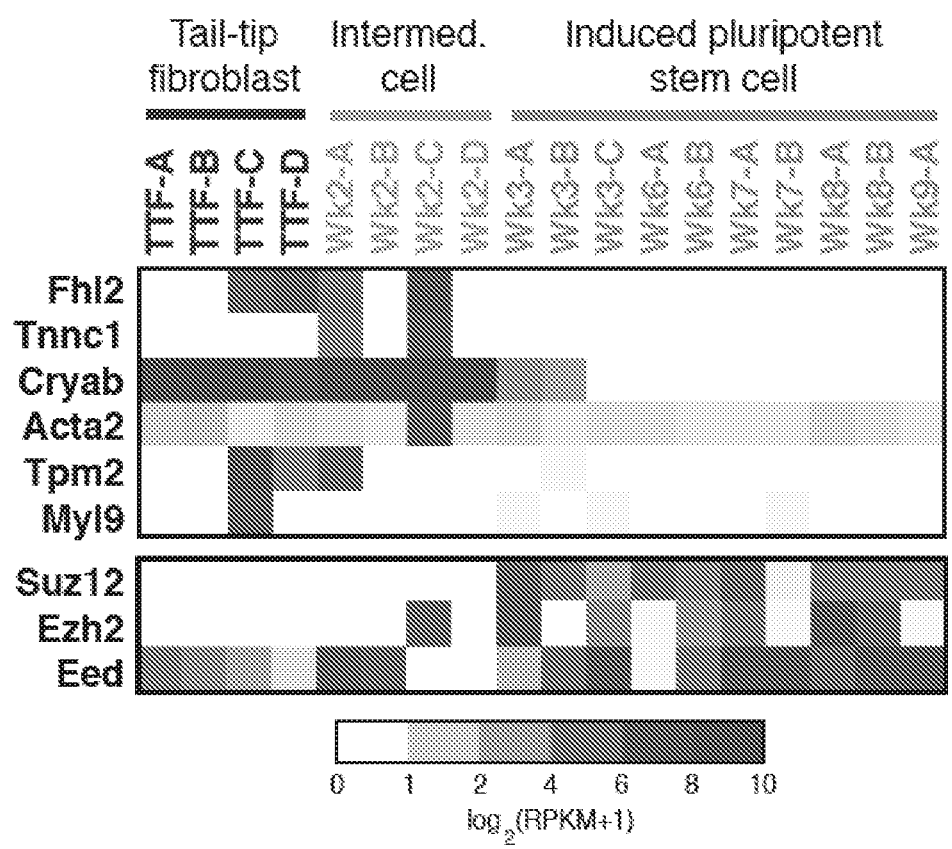
FIG. 16B shows the expression patterns of the indicated genes in the indicated cell types, as described herein.

Gene ontology (GO) analysis showed significant enrichment for the GO terms "contractile fiber," "sarcomere," and "striated muscle thin filament" (FIG. 16A). These muscle-related genes were also expressed in TTFs and intermediate cells at Wk2, but their repression at subsequent timepoints coincided with the activation of the Polycomb genes Ezh2 and Suz12 (FIG. 16B), along with the Polycomb-associated Ladr80 lncRNA (FIG. 12). These results indicate that Ladr80 activation is required to repress a subset of the myogenic program during the course of iPS cell reprogramming.

Figure 16C:
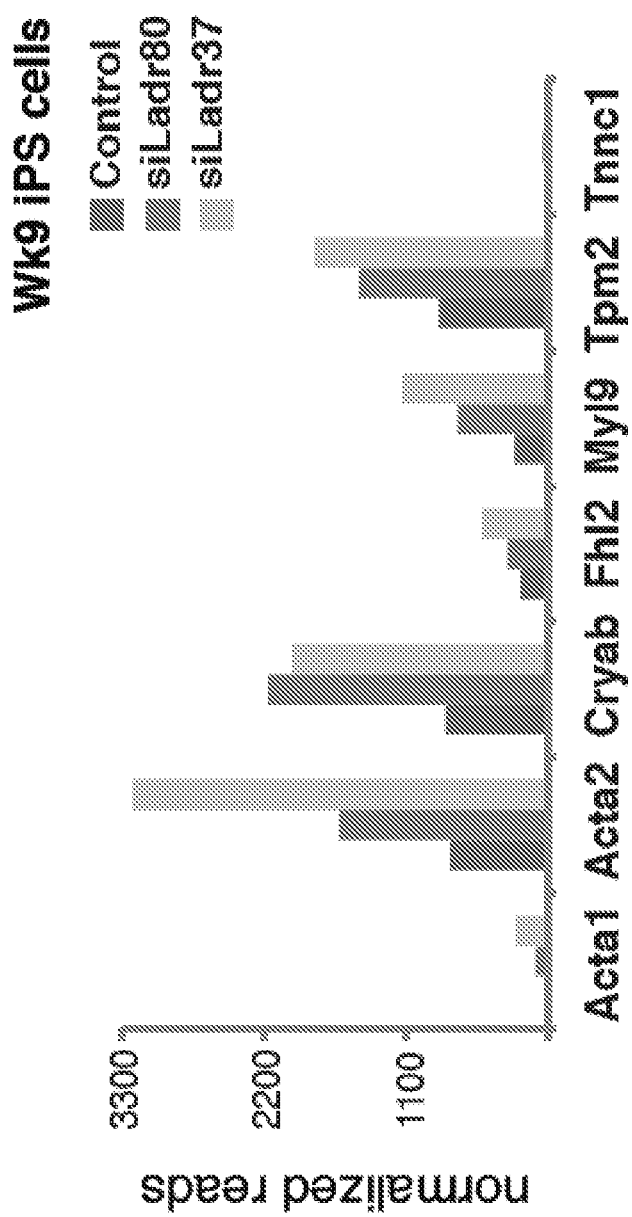
FIG. 16C is a graph showing gene expression of the indicated muscle genes in week 9 (Wk9) iPS cells in the presence of Ladr37 siRNA, Ladr80 siRNA, or control, as indicated, as described herein.
Figure 16D:
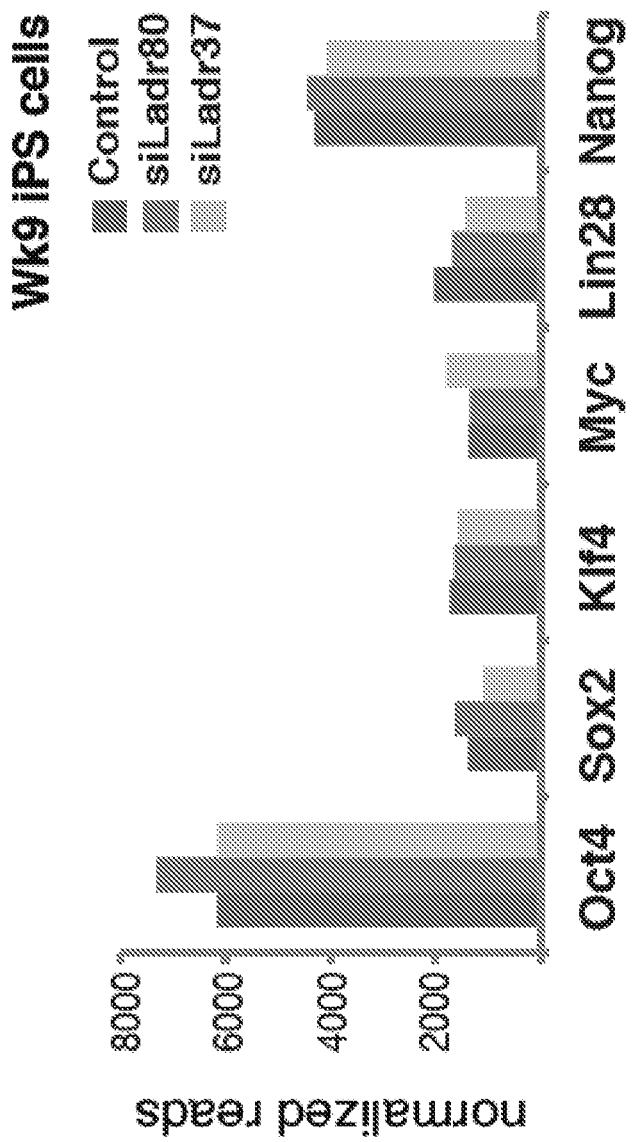
FIG. 16D is a graph showing gene expression of the indicated reprogramming/pluripotency-related genes Oct4, Sox2, Klf4, C-Myc, Lin28, and Nanog in Wk9 iPS cells in the presence of Ladr37 siRNA, Ladr80 siRNA, or control, as described herein.

Furthermore, Ladr37 knockdown resulted in the upregulation of a subset of muscle genes that were also upregulated upon Ladr80 loss-of-function (FIG. 16C), suggesting that lncRNAs may act redundantly during cell fate reprogramming. In addition, Ladr37 knockdown also led to the upregulation of two homeodomain transcription factors involved in limb development: Alx4 and Six2. However, both Ladr80 and Ladr37 knockdowns did not detectably perturb the expression levels of the reprogramming/pluripotency-related genes Oct4, Sox2, Klf4, c-Myc, Lin28, and Nanog (FIG. 16D), consistent with a specific role for these lncRNAs in repressing developmental genes during reprogramming.

Figure 16E:
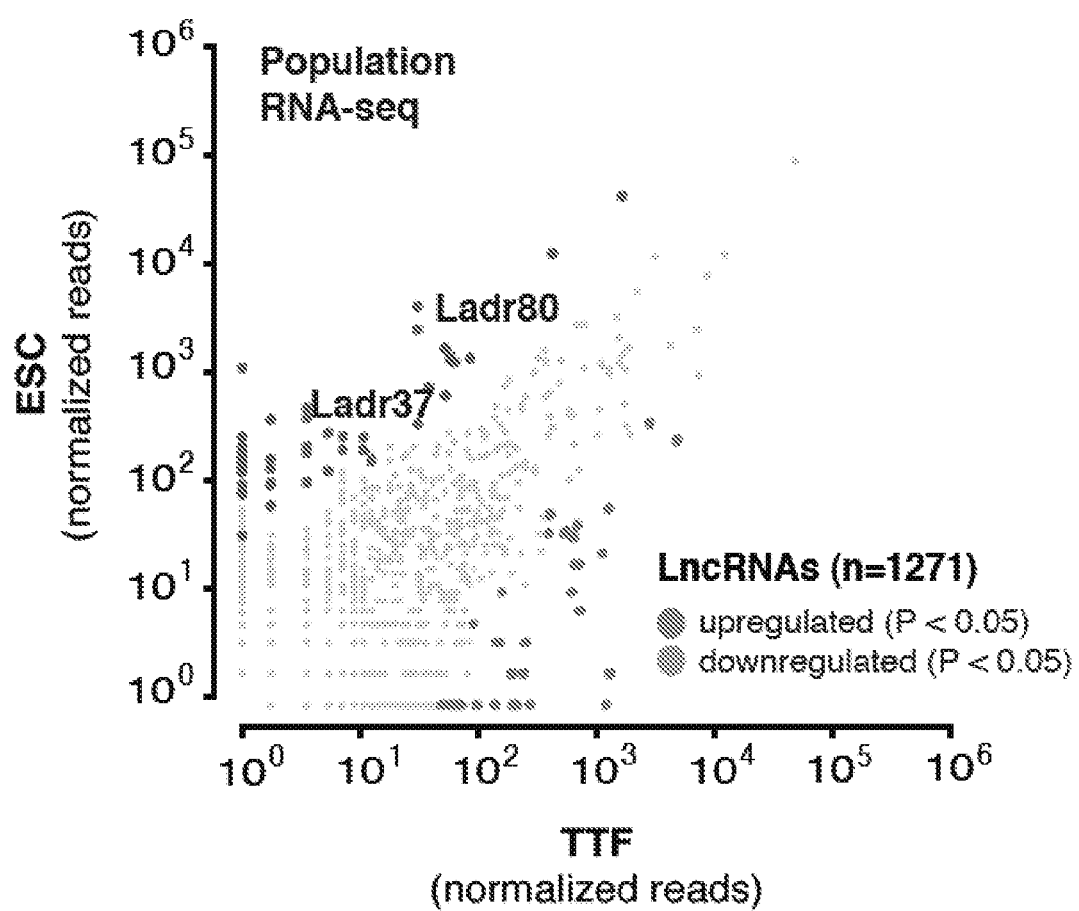
FIG. 16E shows a graph of differential expression analysis of significantly upregulated or downregulated lncRNA genes in ES cells versus TFF cells, as described herein.
Figure 16F:
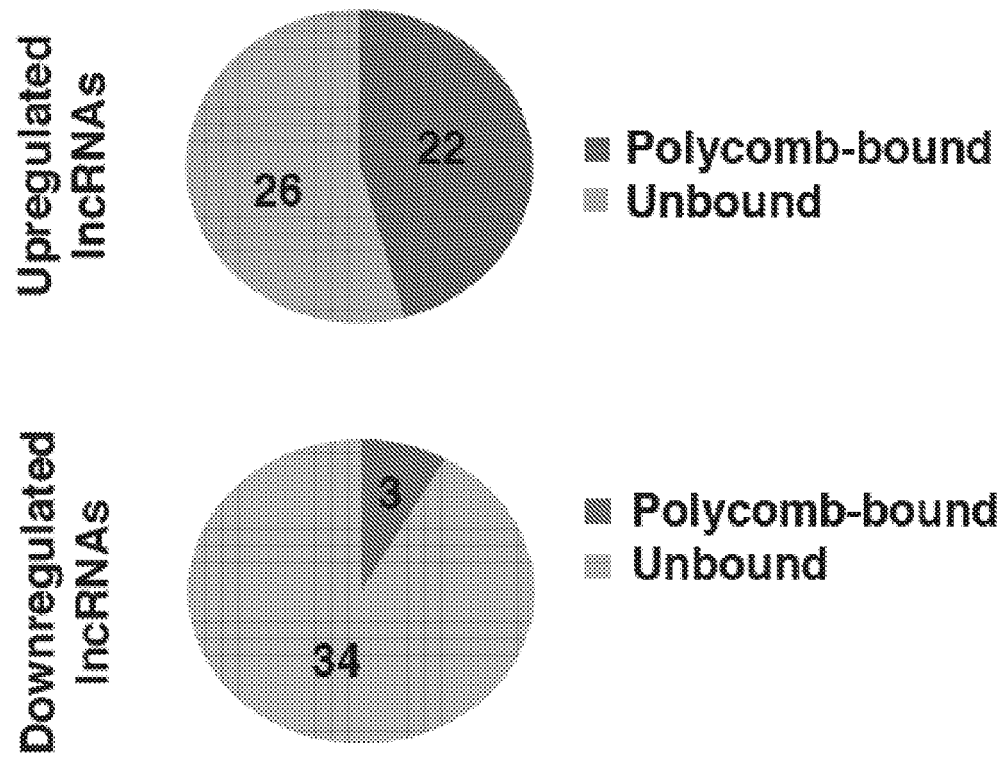
FIG. 16F shows two graphs indicating the fraction of upregulated or downregulated lncRNAs that associated with Polycomb proteins in ES cells, as described herein.

When the differential expression of all Ensembl-annotated lncRNAs was analyzed in populations of ES cells and TTFs, Ladr37 and Ladr80 were among the 48 most significantly upregulated lncRNAs in ES cells versus TTFs (FIG. 16E). Of these 48 upregulated lncRNAs, 22 lncRNAs (46%) associate with Polycomb in ES cells (Guttman et al., 2011; Zhao et al., 2010, supra), whereas of the 37 lncRNAs that are significantly upregulated in TTFs (downregulated in ES cells), only 3 lncRNAs (8%) associate with Polycomb in the pluripotent state (FIG. 16F). These results suggest that additional Polycomb-associated Ladr lncRNAs have functional roles in silencing lineage-specific genes.

Example 6

2i Induces a PGC-Like State in the lncRNA Transcriptome of Late-Stage iPS Cells

Figure 17A:
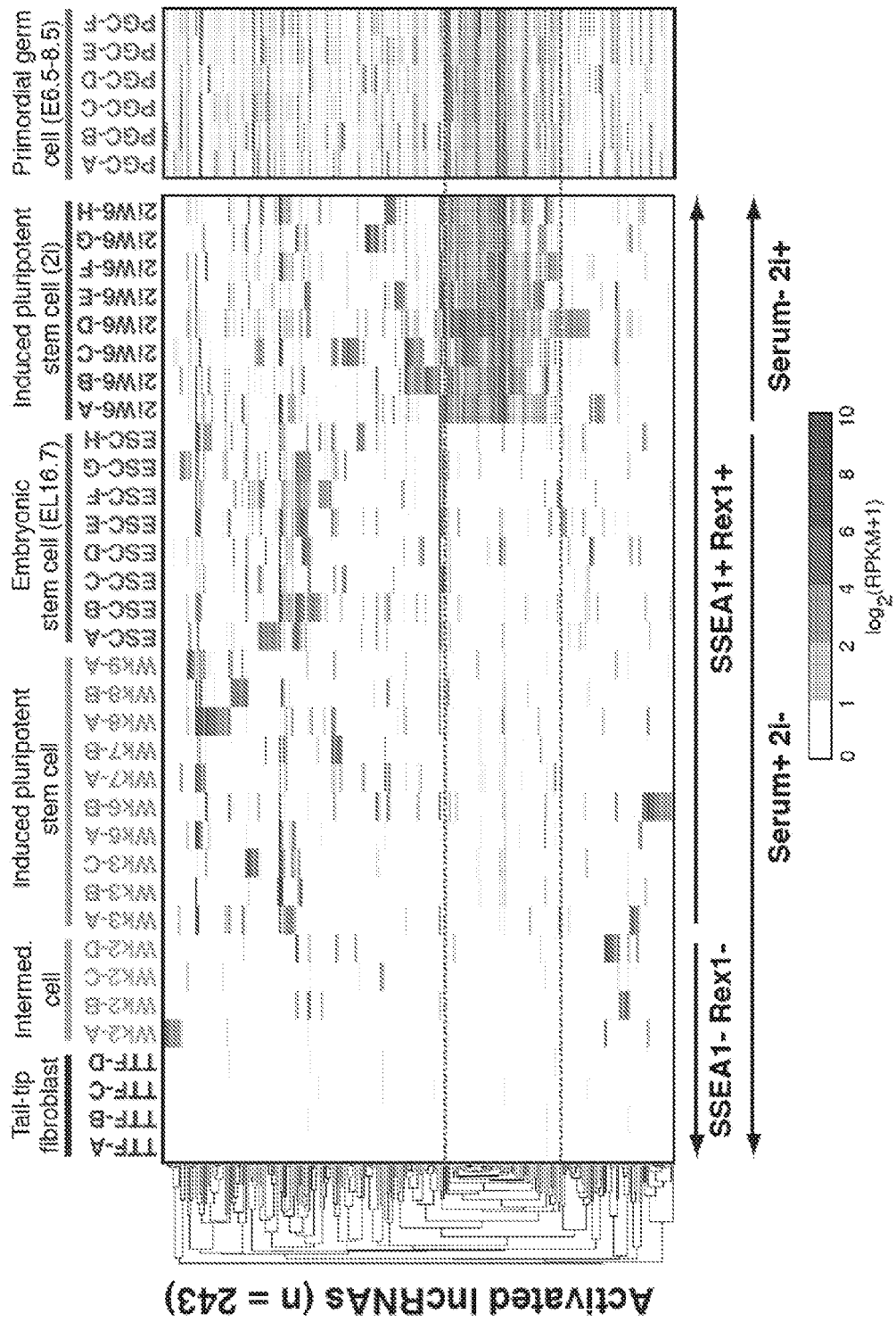
FIG. 17A shows long noncoding RNAs (lncRNAs) that are activated during reprogramming (Ladr) in iPS cells, ES cells, and primordial germ cells (PGC), as determined by single-cell RNA-seq, as described herein.
Figure 17B:
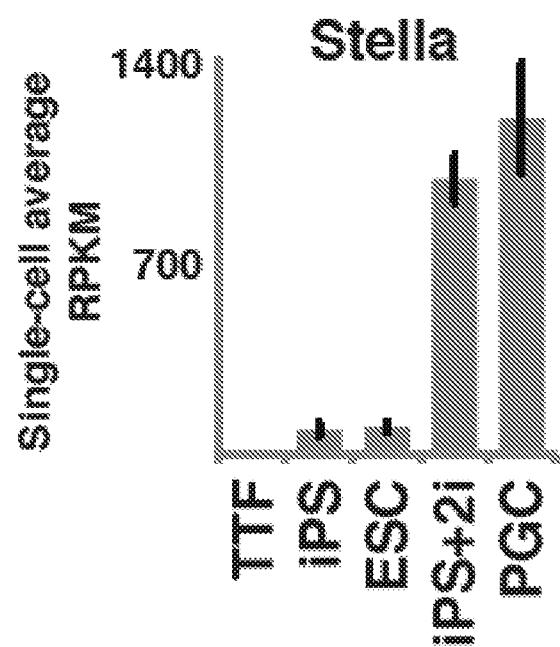
FIG. 17B is a graph showing single-cell average expression levels of Stella in the indicated cell types, as determined by single-cell RNA-seq, as described herein.

It was next examined whether 2i conditions altered the lncRNA landscape in late-stage iPS cells at Wk6. For example, 2i conditions produced a coherent activation of 92 additional lncRNAs (FIG. 17, Tables 1 and 3). Given the delayed activation kinetics of germ cell-related genes in late-stage iPS cells, it was examined whether 2i conditions might enhance their germ cell-like character. Single-cell RNA-seq data from E6.5-E8.5 PGCs was analyzed (Magnusdottir, E. et al., 2013, Nat Cell Biol 15, 905-915, the entire contents of which are herein incorporated by reference) and it was found that a coherent cluster of 2i-activated lncRNAs in iPS cells was also coherently expressed at high levels in PGCs (FIG. 17A). The 2i conditions also resulted in a significant upregulation of Stella (FIG. 17A, FIG. 17B), which is the definitive marker of PGC specification (Leitch, H. G. et al., 2013, Development 140, 2495-2501; and Saitou, M. et al., 2002, Nature 418, 293-300, the entire contents of which are herein incorporated by reference). These results show that iPS cells treated with 2i adopt a more germ cell-like character, similar to ES cells (Hayashi, K. et al., 2008, Cell Stem Cell 3, 391-401, the entire contents of which are herein incorporated by reference), that is especially prominent in their lncRNA transcriptome.

TABLE 6A

Early activation: Wk 2/Wk 3

| SEQ ID NO: | Ladr No | lncRNA |
| --- | --- | --- |
| 34 | Ladr34 | 4930461G14Rik |
| 142 | Ladr142 | Gm16761 |
| 130 | Ladr130 | Hoxa11as |
| 49 | Ladr49 | Gm10143 |
| 158 | Ladr158 | Snord123 |
| 125 | Ladr125 | A930029G22Rik |
| 131 | Ladr131 | Gm17477 |
| 79 | Ladr79 | Gm17279 |
| 94 | Ladr94 | Gm13830 |
| 91 | Ladr91 | Gm12898 |
| 141 | Ladr141 | Gm17344 |
| 107 | Ladr107 | 1110020A21Rik |
| 136 | Ladr136 | 1700028E10Rik |
| 147 | Ladr147 | 4933431E20Rik |
| 144 | Ladr144 | A230056P14Rik |
| 133 | Ladr133 | A330040F15Rik |
| 132 | Ladr132 | C030037D09Rik |
| 137 | Ladr137 | Gm10575 |
| 143 | Ladr143 | Gm11538 |
| 128 | Ladr128 | Gm11818 |
| 113 | Ladr113 | Gm12059 |
| 138 | Ladr138 | Gm15545 |
| 115 | Ladr115 | Gm16244 |
| 145 | Ladr145 | Gm16685 |
| 117 | Ladr117 | Gm16845 |
| 148 | Ladr148 | Gm17565 |
| 146 | Ladr146 | Gm17690 |
| 114 | Ladr114 | Gm17716 |
| 135 | Ladr135 | Gm4890 |
| 134 | Ladr134 | Mir155 |
| 37 | Ladr37 | 4930500J02Rik |
| 17 | Ladr17 | 4930566F21Rik |
| 46 | Ladr46 | Gm17300 |
| 36 | Ladr36 | 2410003L11Rik |
| 41 | Ladr41 | 2500002B13Rik |
| 30 | Ladr30 | Vax2os1 |
| 16 | Ladr16 | 2310043M15Rik |
| 29 | Ladr29 | 9230114K14Rik |
| 122 | Ladr122 | Nespas |
| 80 | Ladr80 | Gm16096 |
| 70 | Ladr70 | C430002E04Rik |
| 127 | Ladr127 | Gm15522 |
| 35 | Ladr35 | Gm16957 |
| 54 | Ladr54 | Gm16986 |
| 129 | Ladr129 | 1700016P03Rik |
| 116 | Ladr116 | 3110045C21Rik |
| 69 | Ladr69 | 4930509G22Rik |
| 40 | Ladr40 | 9530027J09Rik |
| 22 | Ladr22 | 9830144P21Rik |
| 111 | Ladr111 | D030068K23Rik |
| 68 | Ladr68 | Gm17561 |
| 71 | Ladr71 | Gm17605 |
| 55 | Ladr55 | Gm17656 |
| 66 | Ladr66 | Gm17710 |
| 110 | Ladr110 | Gm807 |

TABLE 6B

Late activation: Wk 6+

| SEQ ID NO: | Ladr No | lncRNA |
| --- | --- | --- |
| 18 | Ladr18 | Meg3 |
| 21 | Ladr21 | Rian |
| 3 | Ladr3 | 1810019D21Rik |
| 23 | Ladr23 | 4930513N10Rik |
| 95 | Ladr95 | C330013F16Rik |
| 150 | Ladr150 | 2410133F24Rik |
| 57 | Ladr57 | Abhd1 |
| 39 | Ladr39 | Gm13110 |
| 26 | Ladr26 | Gm16641 |
| 108 | Ladr108 | Gm16723 |
| 25 | Ladr25 | Gm17250 |

TABLE 6B-continued

Late activation: Wk 6+

| SEQ ID NO: | Ladr No | lncRNA |
|---|---|---|
| 38 | Ladr38 | Gm17335 |
| 97 | Ladr97 | 2010300F17Rik |
| 96 | Ladr96 | 4930467K11Rik |
| 99 | Ladr99 | 9530080O11Rik |
| 119 | Ladr119 | A930011O12Rik |
| 4 | Ladr4 | B230208H11Rik |
| 100 | Ladr100 | BC046401 |
| 83 | Ladr83 | Gm13657 |
| 102 | Ladr102 | Gm14817 |
| 86 | Ladr86 | Gm16827 |
| 81 | Ladr81 | Gm17440 |
| 103 | Ladr103 | Gm17501 |
| 82 | Ladr82 | Gm17594 |
| 85 | Ladr85 | Gm17637 |
| 65 | Ladr65 | Gm17659 |
| 98 | Ladr98 | Gm2464 |
| 14 | Ladr14 | 4930526L06Rik |
| 2 | Ladr2 | 4930444M15Rik |
| 19 | Ladr19 | 3110056K07Rik |
| 27 | Ladr27 | 2310010G23Rik |
| 28 | Ladr28 | 2810442I21Rik |
| 42 | Ladr42 | 4933404O12Rik |
| 139 | Ladr139 | A030009H04Rik |
| 90 | Ladr90 | Gm16159 |
| 77 | Ladr77 | Gm16283 |
| 62 | Ladr62 | Gm16880 |
| 109 | Ladr109 | Gm16972 |
| 72 | Ladr72 | Gm17362 |
| 53 | Ladr53 | Gm17418 |
| 33 | Ladr33 | Gm17491 |
| 104 | Ladr104 | Gm17502 |
| 76 | Ladr76 | Gm17597 |
| 124 | Ladr124 | Gm17713 |
| 43 | Ladr43 | Gm2694 |
| 61 | Ladr61 | Gm2788 |
| 63 | Ladr63 | Gm4419 |
| 74 | Ladr74 | Mirg |
| 47 | Ladr47 | Xist |
| 87 | Ladr87 | Atp10d |
| 84 | Ladr84 | C330018A13Rik |
| 149 | Ladr149 | 1700030C12Rik |
| 24 | Ladr24 | 4930404I05Rik |
| 10 | Ladr10 | A330048O09Rik |
| 5 | Ladr5 | Gm15728 |
| 48 | Ladr48 | 4930558J18Rik |
| 64 | Ladr64 | 9330185C12Rik |
| 123 | Ladr123 | Gm10492 |
| 20 | Ladr20 | Gm15441 |
| 1 | Ladr1 | Gm17586 |
| 7 | Ladr7 | 2700086A05Rik |
| 121 | Ladr121 | 4833407H14Rik |
| 12 | Ladr12 | 4930481B07Rik |
| 93 | Ladr93 | 6030442K20Rik |
| 13 | Ladr13 | A730011C13Rik |
| 126 | Ladr126 | Gm16046 |
| 92 | Ladr92 | Gm16973 |
| 9 | Ladr9 | Gm17291 |
| 101 | Ladr101 | Gm17481 |
| 73 | Ladr73 | Gm17525 |
| 11 | Ladr11 | Gm17698 |
| 6 | Ladr6 | Gm2529 |
| 8 | Ladr8 | C430039J16Rik |
| 112 | Ladr112 | Gm8378 |
| 140 | Ladr140 | 0610005C13Rik |
| 75 | Ladr75 | 1010001B22Rik |
| 50 | Ladr50 | 1110002J07Rik |
| 31 | Ladr31 | 1700007L15Rik |
| 105 | Ladr105 | 1700023H06Rik |
| 51 | Ladr51 | 1700086O06Rik |
| 32 | Ladr32 | 4632427E13Rik |
| 106 | Ladr106 | 4930480K23Rik |
| 78 | Ladr78 | 4933407K13Rik |
| 88 | Ladr88 | 5730457N03Rik |
| 58 | Ladr58 | 5930412G12Rik |
| 52 | Ladr52 | 6720401G13Rik |
| 44 | Ladr44 | A230072C01Rik |
| 56 | Ladr56 | B230206L02Rik |
| 120 | Ladr120 | C030010L15Rik |
| 45 | Ladr45 | C330046G13Rik |
| 151 | Ladr151 | C530005A16Rik |
| 59 | Ladr59 | E130018N17Rik |
| 118 | Ladr118 | Gm10658 |
| 67 | Ladr67 | Gm10785 |
| 89 | Ladr89 | Gm11714 |
| 60 | Ladr60 | Gm14022 |
| 15 | Ladr15 | Gm15787 |

TABLE 6C 2i-induced activation: Wk 6

| SEQ ID NO: | Ladr No | lncRNA |
|---|---|---|
| 220 | Ladr220 | 1110046J04Rik |
| 224 | Ladr224 | 1110019D14Rik |
| 212 | Ladr212 | 1700007J10Rik |
| 159 | Ladr159 | 1700023L04Rik |
| 239 | Ladr239 | 2010110K18Rik |
| 183 | Ladr183 | 2310031A07Rik |
| 219 | Ladr219 | 2610027K06Rik |
| 223 | Ladr223 | 2610206C17Rik |
| 164 | Ladr164 | 2810011L19Rik |
| 237 | Ladr237 | 2810425M01Rik |
| 187 | Ladr187 | 2810429I04Rik |
| 182 | Ladr182 | 2900052L18Rik |
| 177 | Ladr177 | 3010001F23Rik |
| 236 | Ladr236 | 3100003L05Rik |
| 214 | Ladr214 | 4833417C18Rik |
| 184 | Ladr184 | 4930506C21Rik |
| 217 | Ladr217 | 6430562O15Rik |
| 155 | Ladr155 | 9530059O14Rik |
| 188 | Ladr188 | A230004M16Rik |
| 211 | Ladr211 | A330032B11Rik |
| 178 | Ladr178 | A330076H08Rik |
| 222 | Ladr222 | A730081D07R1k |
| 191 | Ladr191 | A730099G02Rik |
| 176 | Ladr176 | A930007I19Rik |
| 174 | Ladr174 | AY512931 |
| 203 | Ladr203 | BC051077 |
| 169 | Ladr169 | C330002G04Rik |
| 157 | Ladr157 | Dio3os |
| 172 | Ladr172 | F630040L22Rik |
| 160 | Ladr160 | Gdap10 |
| 180 | Ladr180 | Gm10425 |
| 194 | Ladr194 | Gm17638 |
| 192 | Ladr192 | Gm17644 |
| 221 | Ladr221 | Gm17675 |
| 162 | Ladr162 | Gm17692 |
| 190 | Ladr190 | Gm17699 |
| 153 | Ladr153 | Gm17701 |
| 233 | Ladr233 | Gm2366 |
| 199 | Ladr199 | Gm3906 |
| 175 | Ladr175 | Gm6410 |
| 218 | Ladr218 | Gm7782 |
| 241 | Ladr241 | Gm9917 |
| 216 | Ladr216 | Mir706 |
| 213 | Ladr213 | Gm11542 |
| 186 | Ladr186 | Gm11574 |
| 230 | Ladr230 | Gm11602 |
| 197 | Ladr197 | Gm11934 |
| 167 | Ladr167 | Gm12592 |
| 163 | Ladr163 | Gm12784 |
| 200 | Ladr200 | Gm12976 |
| 168 | Ladr168 | Gm13261 |
| 198 | Ladr198 | Gm15396 |
| 154 | Ladr154 | Gm15489 |
| 179 | Ladr179 | Gm15850 |
| 242 | Ladr242 | Gm16568 |
| 165 | Ladr165 | Gm16618 |

TABLE 6C-continued 2i-induced activation: Wk 6

| SEQ ID NO: | Ladr No | lncRNA |
|---|---|---|
| 243 | Ladr243 | Gm16624 |
| 181 | Ladr181 | Gm16629 |
| 231 | Ladr231 | Gm16684 |
| 196 | Ladr196 | Gm16702 |
| 225 | Ladr225 | Gm16706 |
| 185 | Ladr185 | Gm16733 |
| 229 | Ladr229 | Gm16739 |
| 195 | Ladr195 | Gm16755 |
| 201 | Ladr201 | Gm16862 |
| 170 | Ladr170 | Gm16869 |
| 227 | Ladr227 | Gm16889 |
| 166 | Ladr166 | Gm16912 |
| 171 | Ladr171 | Gm16938 |
| 156 | Ladr156 | Gm17102 |
| 238 | Ladr238 | Gm17238 |
| 152 | Ladr152 | Gm17254 |
| 193 | Ladr193 | Gm17255 |
| 205 | Ladr205 | Gm17275 |
| 215 | Ladr215 | Gm17282 |
| 226 | Ladr226 | Gm17317 |
| 207 | Ladr207 | Gm17327 |
| 210 | Ladr210 | Gm17336 |
| 189 | Ladr189 | Gm17392 |
| 173 | Ladr173 | Gm17445 |
| 235 | Ladr235 | Gm17451 |
| 228 | Ladr228 | Gm17452 |
| 202 | Ladr202 | Gm17496 |
| 240 | Ladr240 | Gm17499 |
| 161 | Ladr161 | Gm17500 |
| 209 | Ladr209 | Gm17517 |
| 234 | Ladr234 | Gm17529 |
| 232 | Ladr232 | Gm17548 |
| 206 | Ladr206 | Gm17596 |
| 208 | Ladr208 | Gm17599 |
| 204 | Ladr204 | Gm17632 |

Figure 18A:
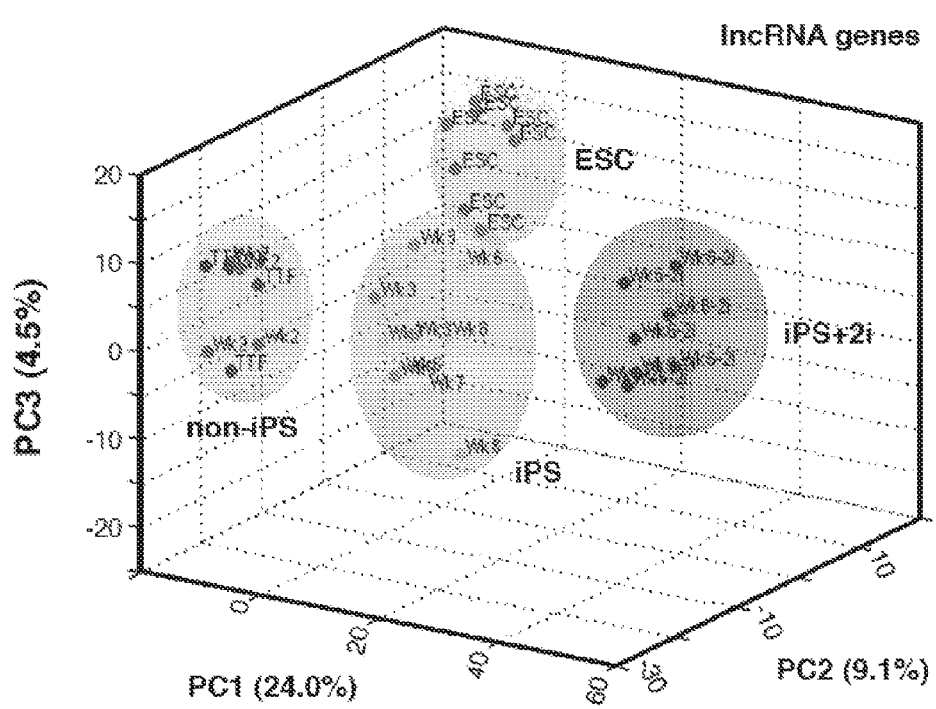
FIG. 18A is graph comparing Ladr lncRNAs with lncRNAs in ES cells, as described herein.
Figure 18B:
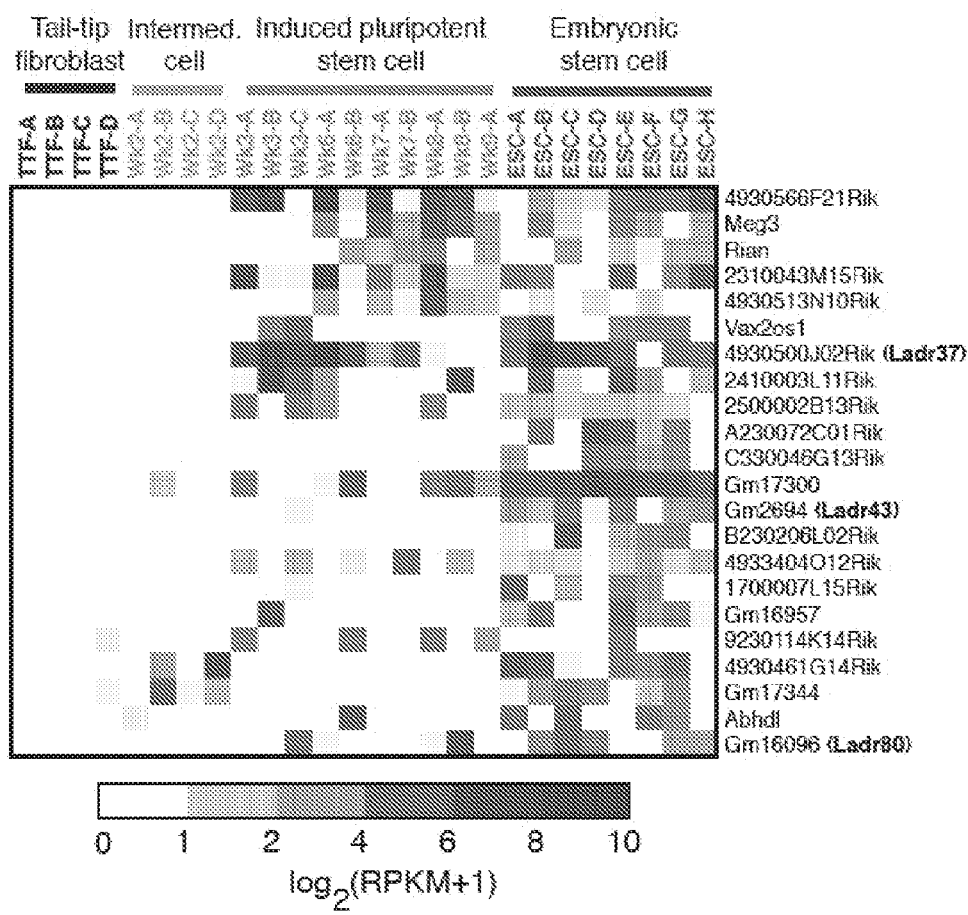
FIG. 18B shows the expression patterns of the indicated lncRNAs in the indicated cell types, as described herein.
Figure 18C:
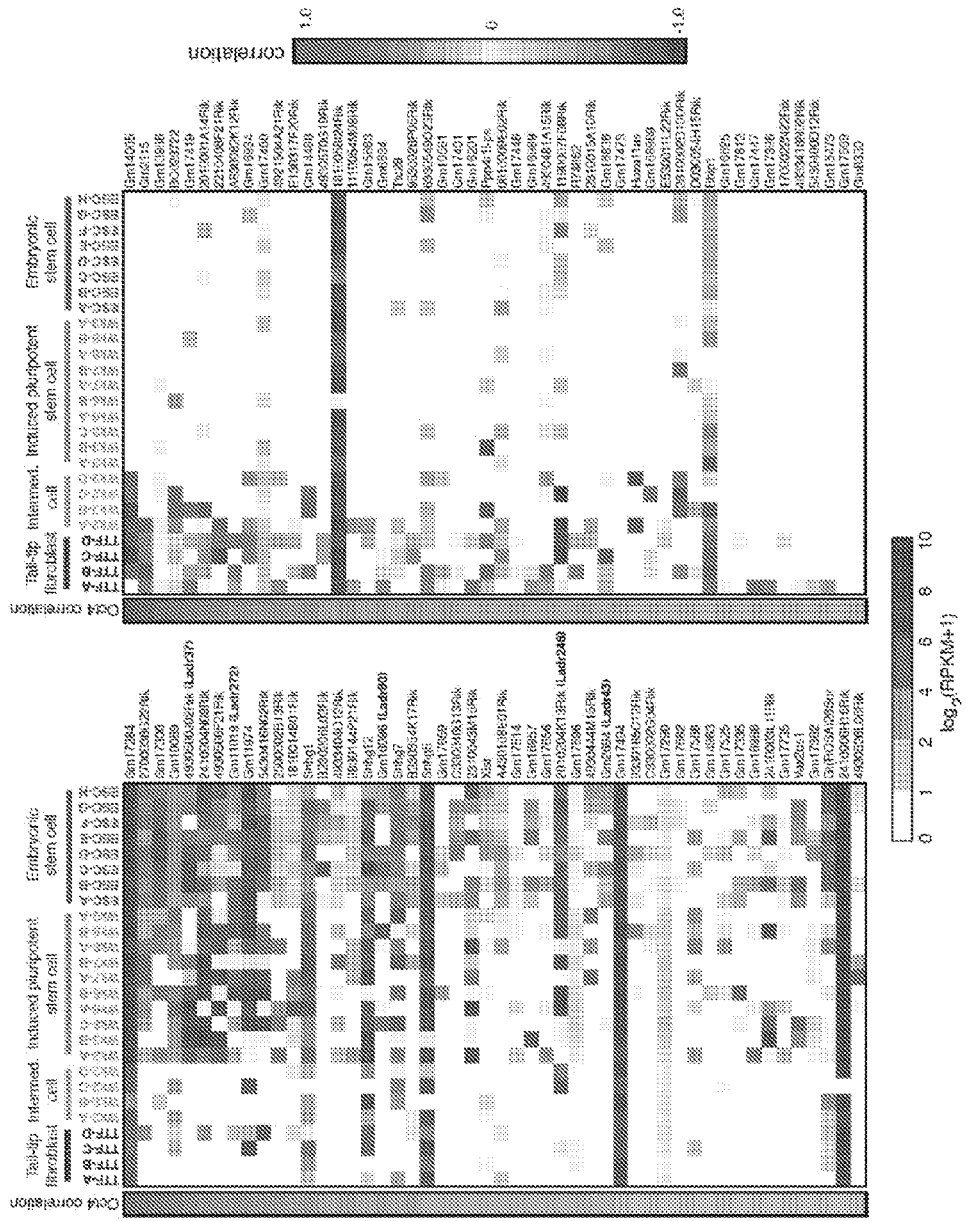
FIG. 18C shows the expression patterns of the indicated lncRNAs in the indicated cell types including relative Oct4 correlation as indicated, as described herein.
Figure 19B:
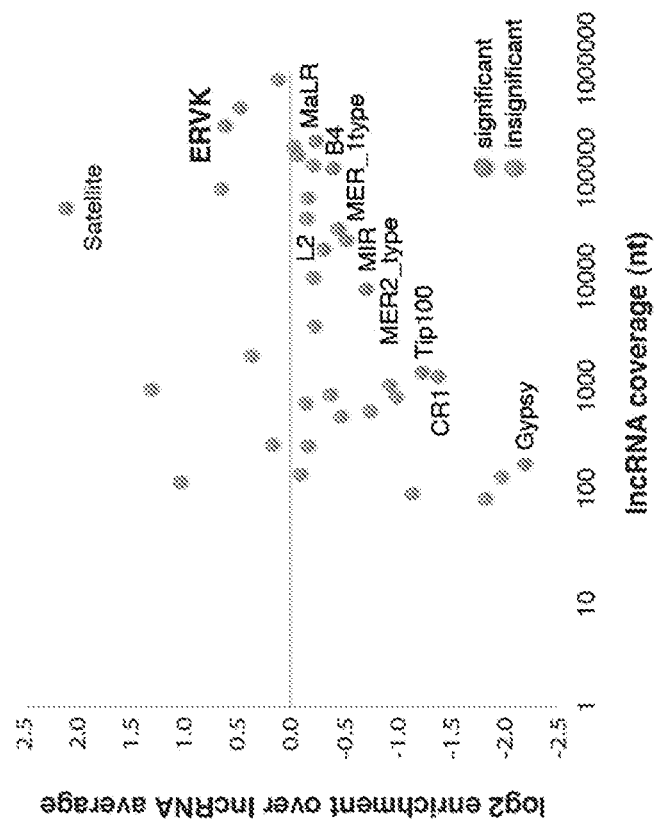
FIG. 19B is a graph showing the enrichment of elements (e.g., ERVK) in Ladr lncRNAs versus, as described herein.
Figure 19A:
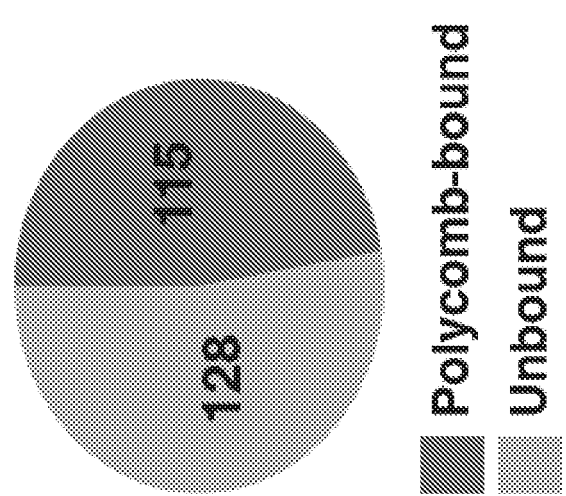
FIG. 19A shows a graph indicating the fraction of the Ladr lncRNAs (115) that associate with Polycomb proteins (Polycomb-bound) in ES cells, as described herein.
Figure 19C:
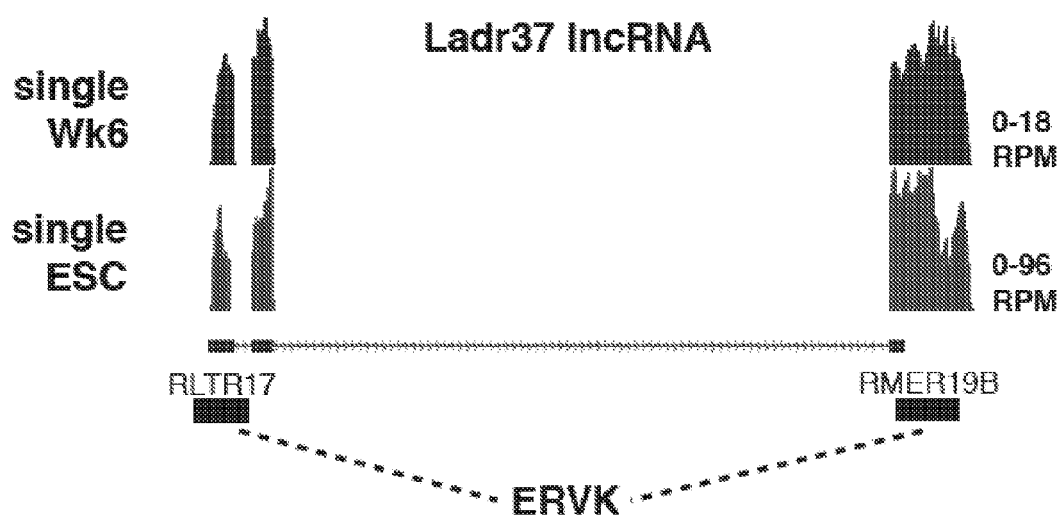
FIG. 19C is a schematic showing that Ladr37 is flanked by two different ERVK elements whose sequences overlap with its 5' and 3' exons, as described herein.

Ladr lncRNAs have both common and distinctive characteristics when compared with lncRNAs expressed in ES cells (FIG. 18A, 18B, 18C). Of the 243 Ladr lncRNAs, 115 (47%) associate with Polycomb proteins in ES cells (FIG. 19A) (Guttman et al., 2011; Zhao et al., 2010, supra). Ladr lncRNAs are also enriched for the LTR transposable element ERVK, an endogenous retrovirus (FIG. 19B). It was previously shown that lncRNAs containing endogenous retroviral elements are expressed at higher levels in ES cells relative to somatic cells (Kelley, D. et al., 2012, Genome Biol 13, R107, the entire contents of which are herein incorporated by reference). Although Ladr80 was not comprised of any ERVK sequence, Ladr37 was flanked by two different ERVK elements whose sequences overlapped with its 5' and 3' exons (FIG. 19C), which may contribute to its high levels of expression in both ES and iPS cells (FIG. 12) (Kelley and Rinn, 2012, supra). Of the 92 Ladr lncRNAs that were strongly upregulated in response to 2i, more than half (n=47) were associated with ERVK elements. Taken together with results from a previous study (Kelley and Rinn, 2012, supra), the results suggest that endogenous retroviral elements are involved in Ladr lncRNA regulation during reprogramming.

Example 7

Ladr lncRNA Regulation by ES Cell and PGC Transcriptional Networks

Figure 20A:
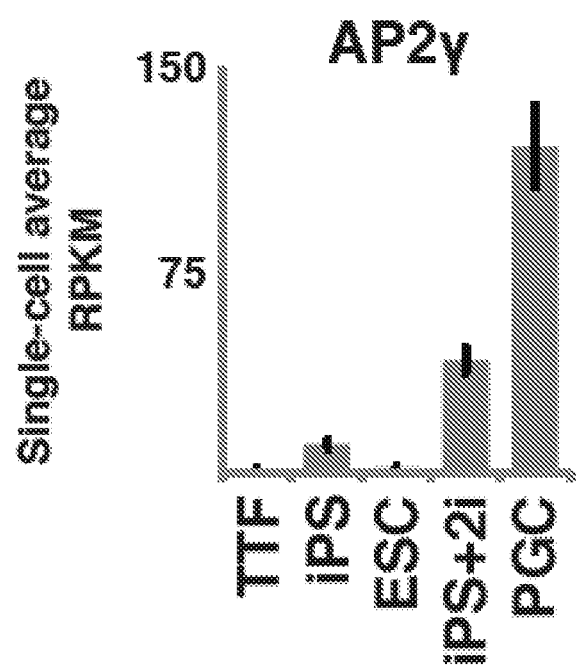
FIG. 20A is a graph showing expression of AP2γ (in RPKM) in the indicated cell types, as described herein.
Figure 20C:
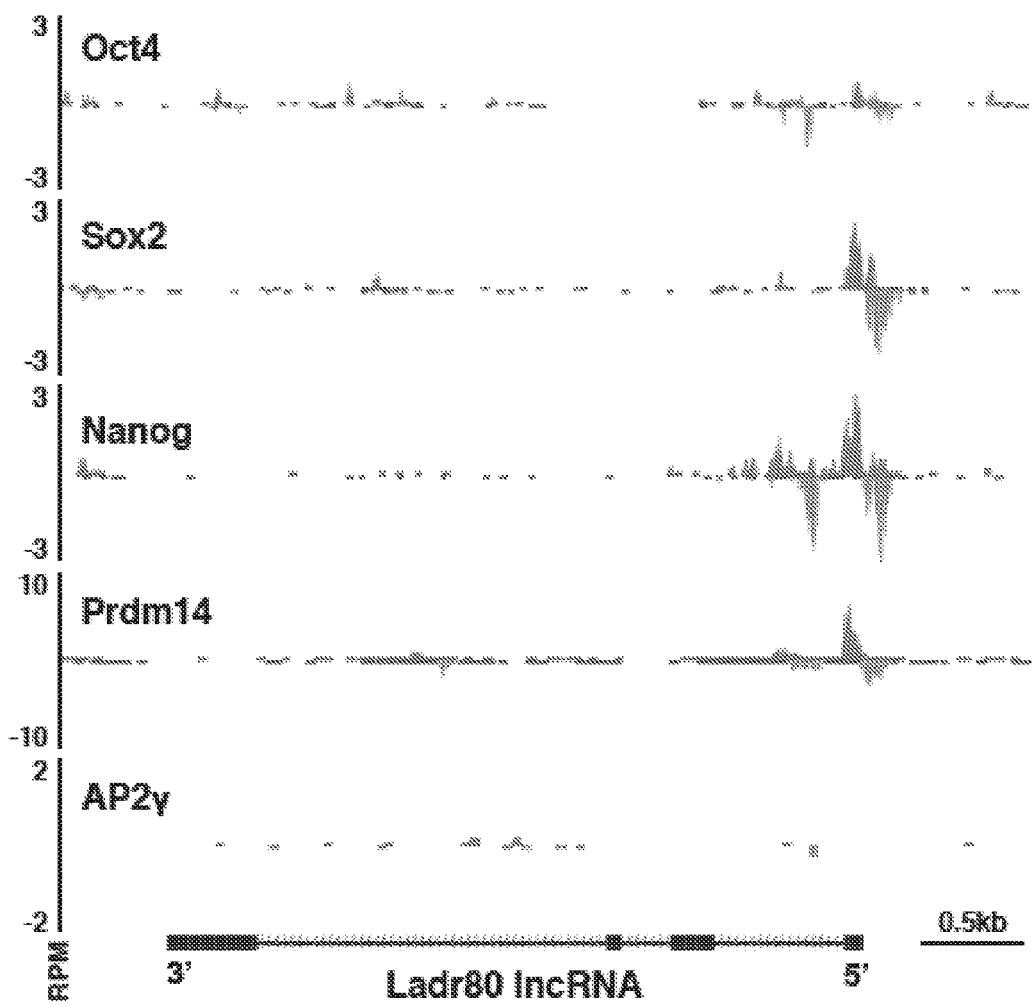
FIG. 20C shows ChIP sequence data for Ladr80 lncRNA, Ladr169 lncRNA, Ladr37 lncRNA, or Ladr43 lncRNA, as indicated, analyzed with respect to Oct 4, Sox2, Nanog, Prdm14 and AP2γ, as described herein.
Figure 20C:
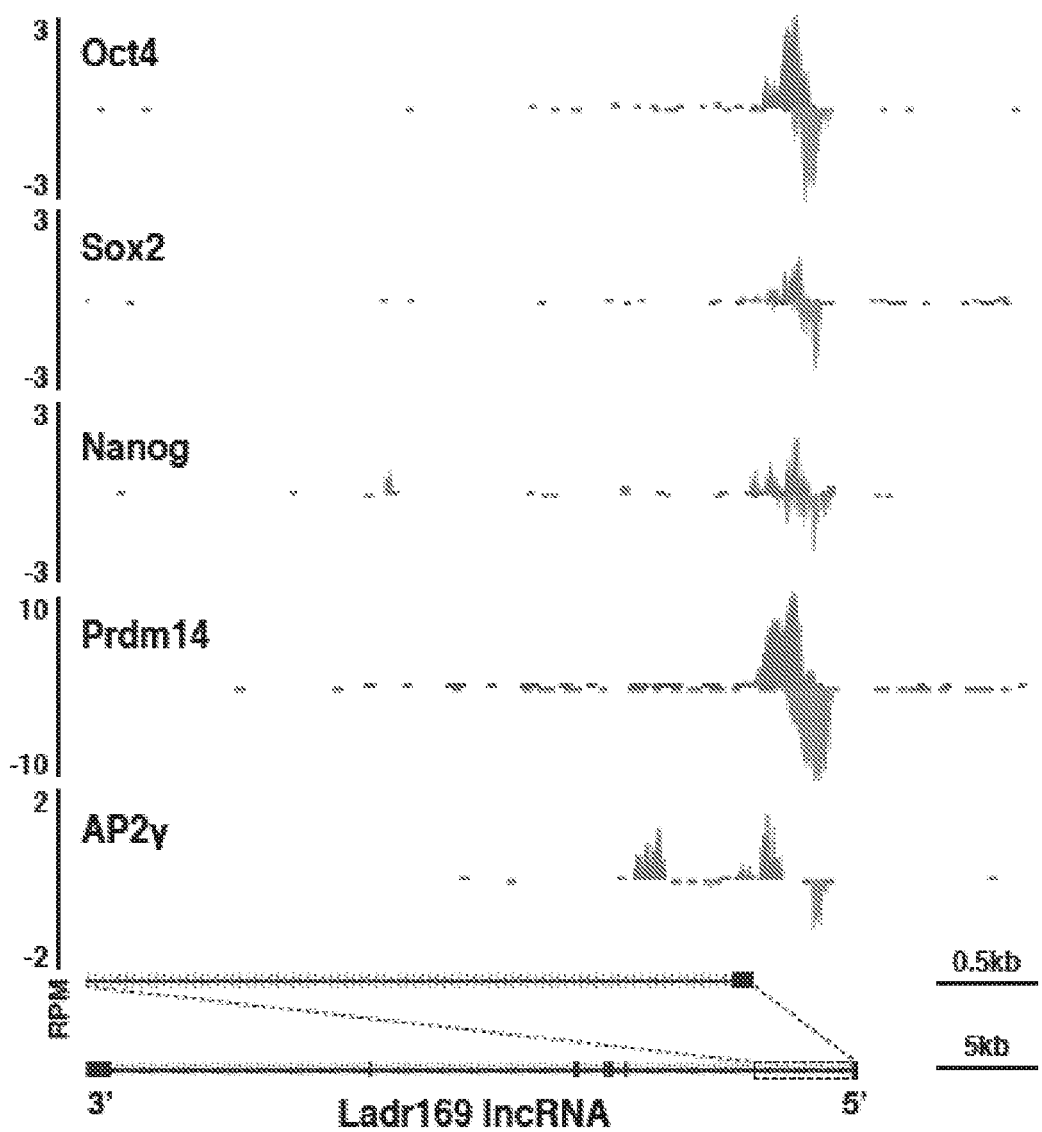
Figure 20C:
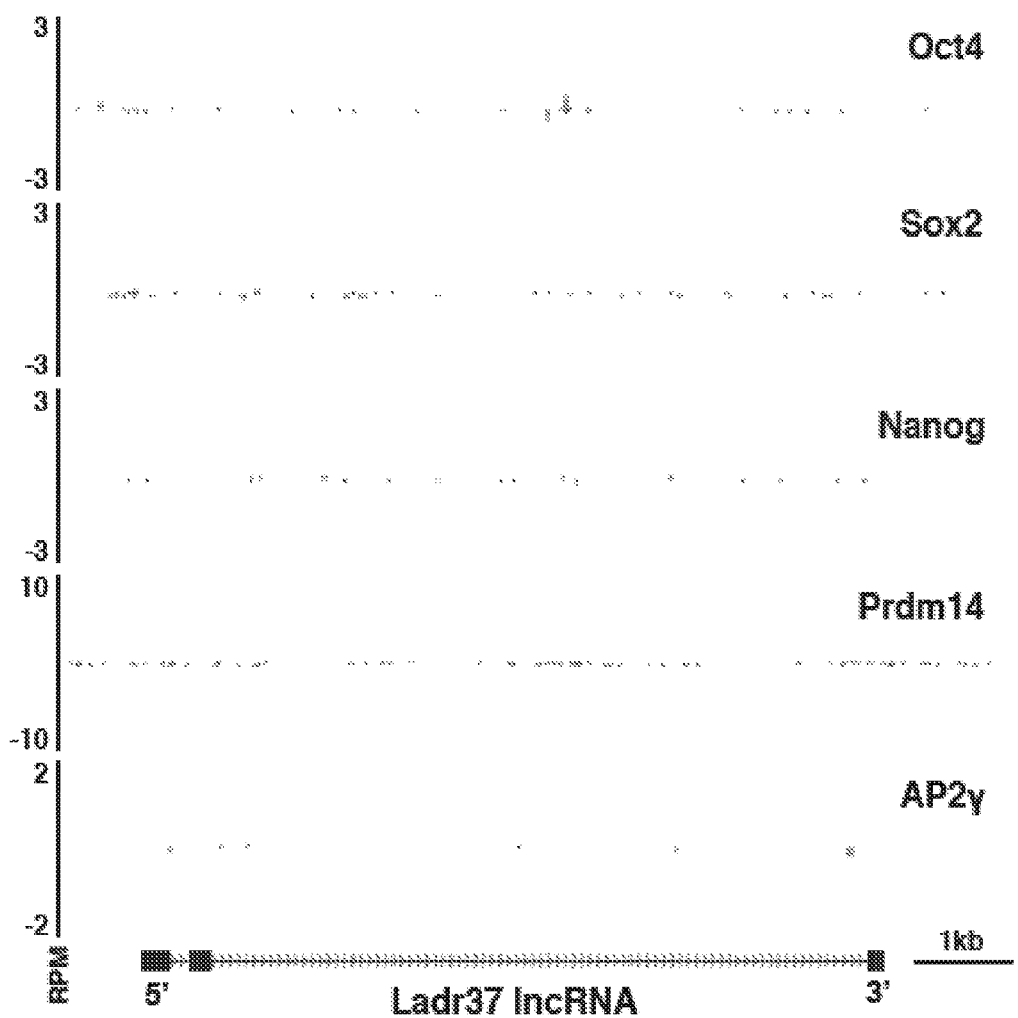
Figure 20C:
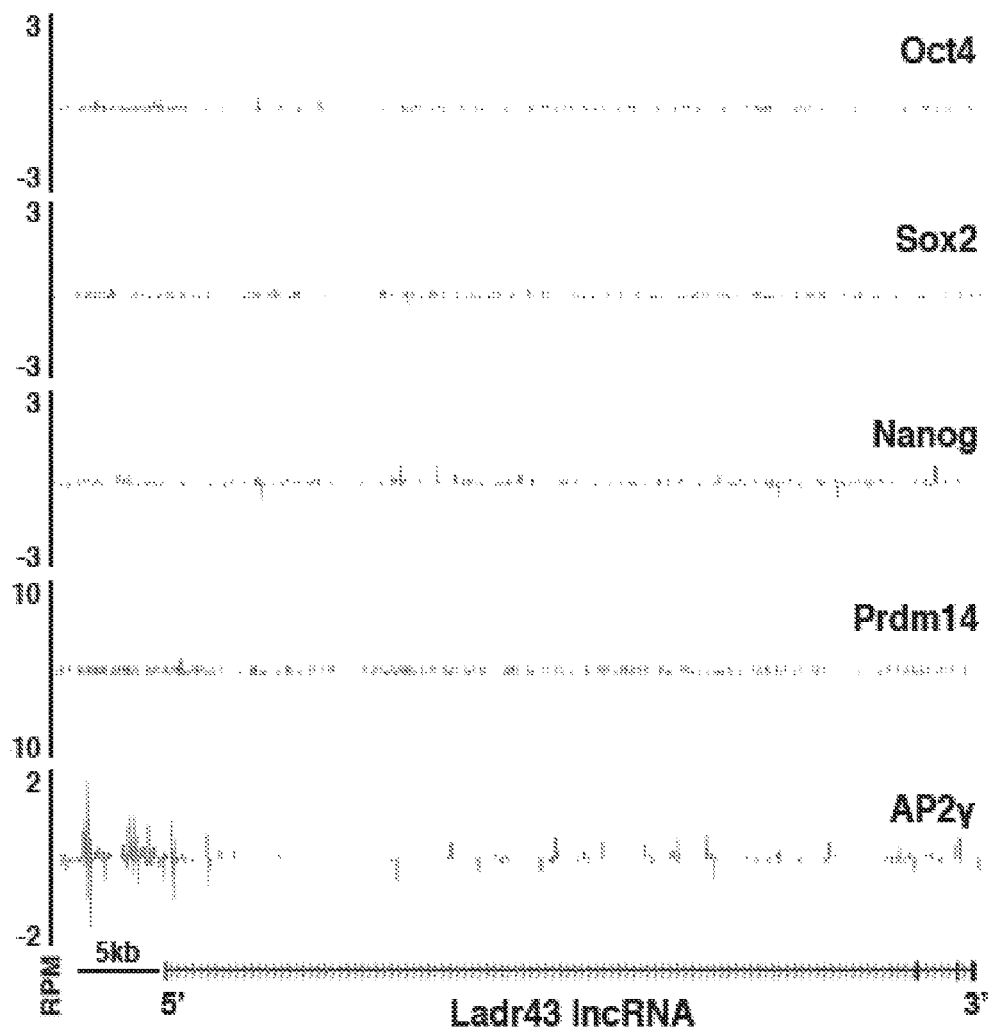

In order to examine whether Ladr lncRNAs were regulated by ES cell or PGC transcription factor networks, chromatin immunoprecipitation high-throughput sequencing (ChIP-seq) data was analyzed for the core pluripotency factors Oct4/Sox2/Nanog (Marson, A. et al., 2008, Cell 134, 521-533, the entire contents of which are herein incorporated by reference) and for Prdm14/AP2γ, which initiate the specification of PGCs (Magnusdottir et al., 2013, supra). Late-stage iPS cells, both in the absence and presence of 2i, expressed 5- to 20-fold higher levels of AP2γ relative to ES cells (FIG. 20A). Moreover, of the 243 Ladr lncRNAs, AP2γ had the highest number of binding sites within lncRNA promoters (n=86) (FIG. 20B). Prdm14 and Oct4 exhibited the second (n=71) and third (n=31) highest number of binding sites, respectively (FIG. 20B). Ladr lncRNAs whose expression patterns correlated most strongly with Oct4 were generally expressed in ES cells, while lncRNAs that were anti-correlated with Oct4 tended to be expressed in TTFs (FIG. 18C). It was also observed that many of the Ladr lncRNA genes were bound by multiple transcription factors. For example, the Ladr80 promoter region was bound by Sox2, Nanog, and Prdm14, while a 2i-induced lncRNA, Ladr169, was bound by Oct4/Sox2/Nanog and Prdm14/AP2γ (FIG. 20C). However, the Ladr37 promoter was not bound by any of these factors, while Ladr43 was bound by AP2γ (FIG. 20C). These findings suggest that both ES cell and PGC transcriptional networks regulate Ladr activation during iPS cell reprogramming.

Example 8

Ladr lncRNA Suppression of Lineage-Specific Genes

Figure 21B:
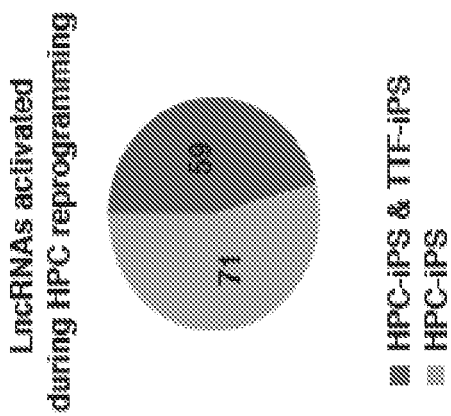
FIG. 21B is a graph showing the fraction of lncRNAs activated during HPC reprogramming, as described herein.
Figure 21A:
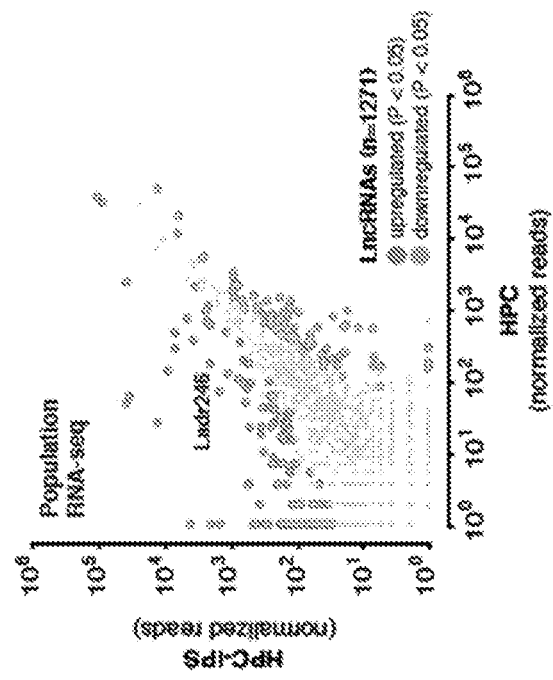
FIG. 21A is a graph showing the amount of upregulated lncRNAs or downregulated lncRNAs, as indicated, in iPS cells derived from hematopoietic progenitor cells (HPC-iPS cells) compared to HPC cells, as described herein.
Figure 21C:
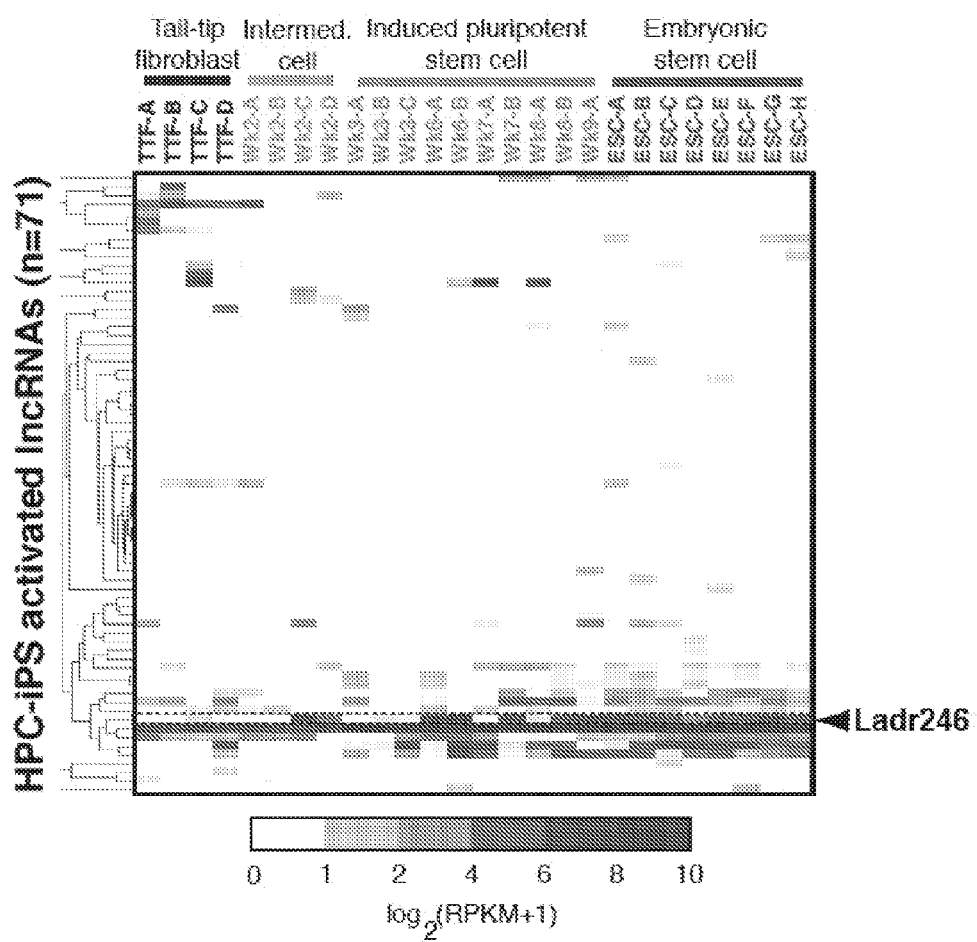
FIG. 21C shows long noncoding RNAs (lncRNAs) that are activated in HPC-iPS cells during reprogramming, according to embodiments of the invention.
Figure 21D:
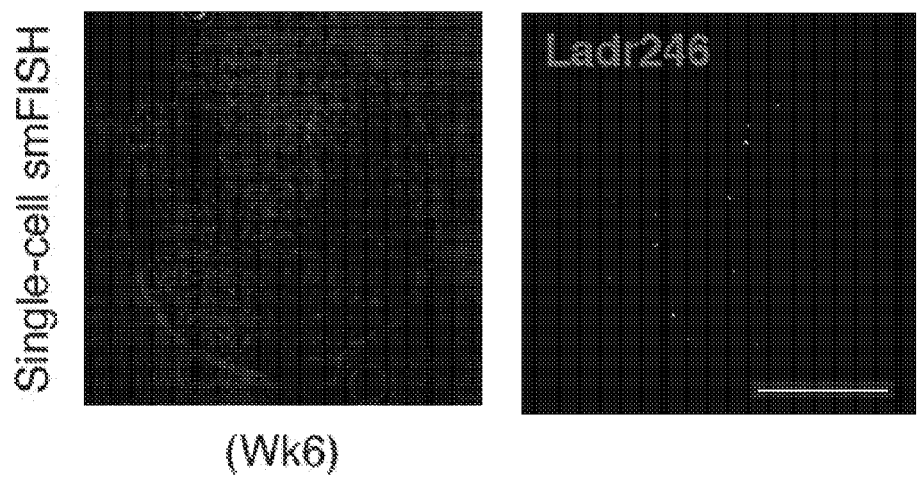
FIG. 21D is a fluorescent image of a single cell at week 6 (Wk6) of iPS cell reprogramming using smFISH, with Ladr246 probe, as described herein.
Figure 21E:
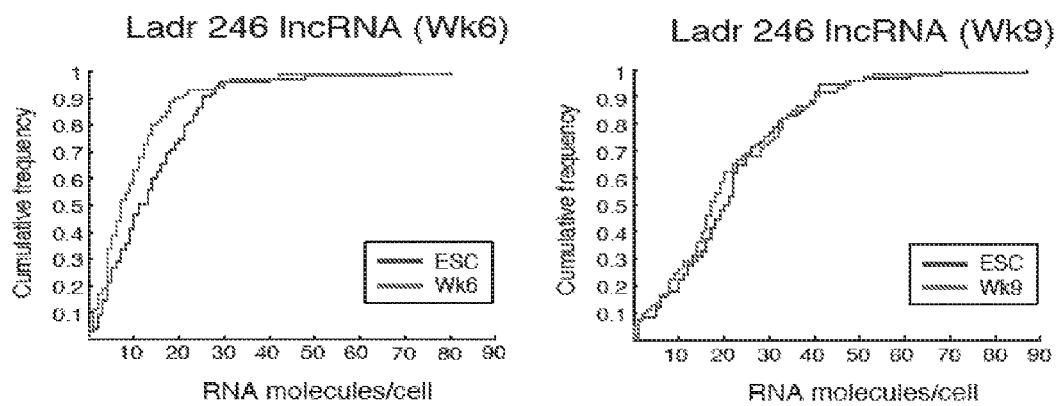
FIG. 21E shows two graphs of cumulative frequency of Ladr246 lncRNAs at week 6 (Wk6) and week 9 (Wk9) compared with ESC (embryonic stem cells), as described herein.
Figure 21F:
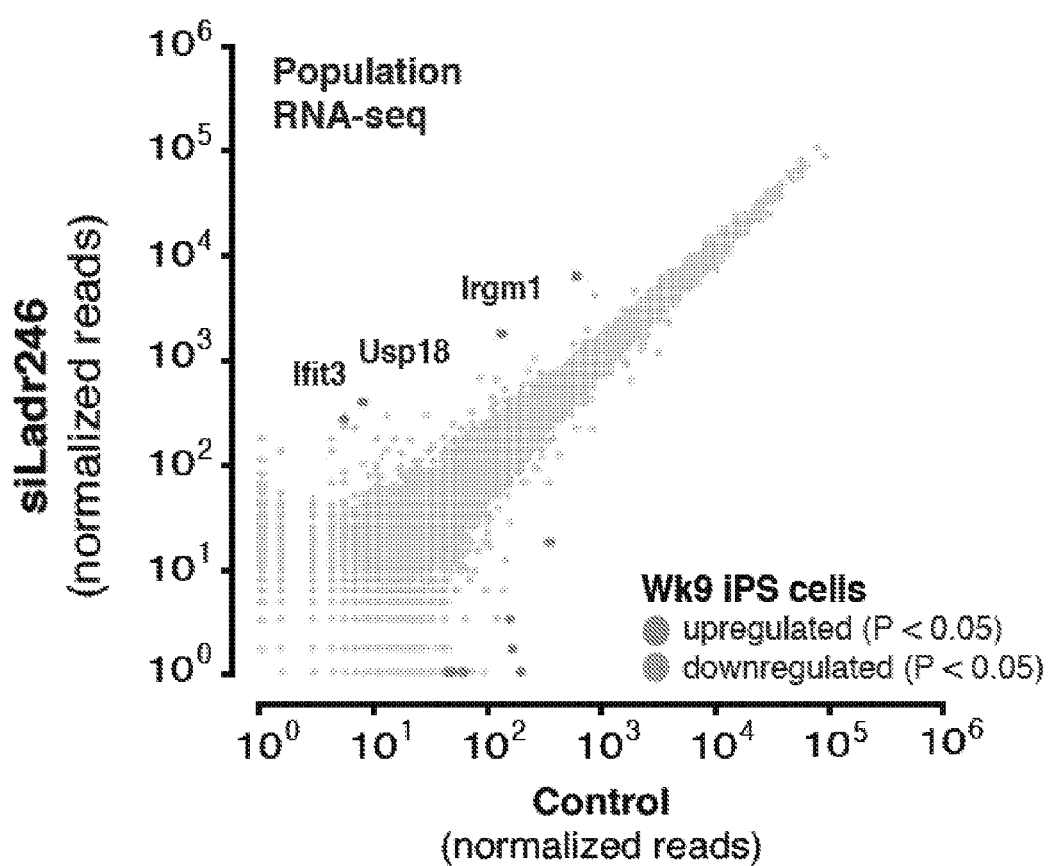
FIG. 21F is a graph showing differential expression analysis of upregulated or downregulated genes, as indicated, in week 9 (Wk9) iPS cells in the presence (siLadr246) or absence (control) of Ladr246 siRNA, as described herein.

To search for additional lineage-specific Ladr lncRNAs, upregulated genes were analyzed in iPS cells derived from hematopoietic progenitor cells (HPC) (Chang, G. et al., 2014, Cell Res 24, 293-306, the entire contents of which are herein incorporated by reference). This analysis revealed that 130 lncRNAs were activated during HPC reprogramming into iPS cells, and more than half (n=71) were upregulated specifically in HPC-iPS cells, while the remaining lncRNAs (n=59) were activated during both HPC and TTF reprogramming (FIGS. 21B and 12). Of the 71 HPC-iPS lncRNAs, most were not expressed in ES or TTF-iPS cells (FIG. 21C). However, a small number of HPC-iPS lncRNAs were prominently expressed in ES cells, while exhibiting apparent heterogeneity in our iPS cells and TTFs (FIG. 21C). One of these lncRNAs (Ladr246) was examined using smFISH, which showed that Wk6 iPS cells expressed Ladr246 at aberrantly low levels relative to ES cells (FIG. 21D). In Wk9 iPS cells, however, the distribution of Ladr246 expression was indistinguishable from that of ES cells, indicating relatively late activation kinetics for Ladr246 (FIG. 21D, 21E). Additionally, when Ladr246 loss-of-function studies were performed in Wk9 iPS cells (FIGS. 15A, 15B), it was observed that Ladr246 was required to repress three genes involved in interferon signaling: Irgm1, Usp18, and Ifit3 (FIG. 21F). These results are consistent with a lineage-specific role for Ladr246 in repressing hematopoietic genes during HPC reprogramming.

Example 9

Knockdown Analysis of Ladr272 and Ladr43

Mouse Ladr 272 and Mouse Ladr 43 having orthologous sequences in the human genome as determined by liftOver analysis were analyzed in knockdown experiments. Specifically, differential expression analysis of significantly upregulated or downregulated genes in week 9 (Wk9) iPS cells were made deficient for the Ladr272 or Ladr43 using siLadr272 and siLadr43, as indicated in FIGS. 22A and 22B, respectively. Gene expression was determined by population level RNA-seq as described herein, and gene ontology (GO) analysis for significantly enriched GO terms in downregulated genes. Bonferroni-corrected P-values are shown in FIGS. 22A and 22B. Individually labeled points are a common set of genes downregulated in both Ladr 272 and Ladr43 loss-of-function experiments.

Example 10

Figure 23:
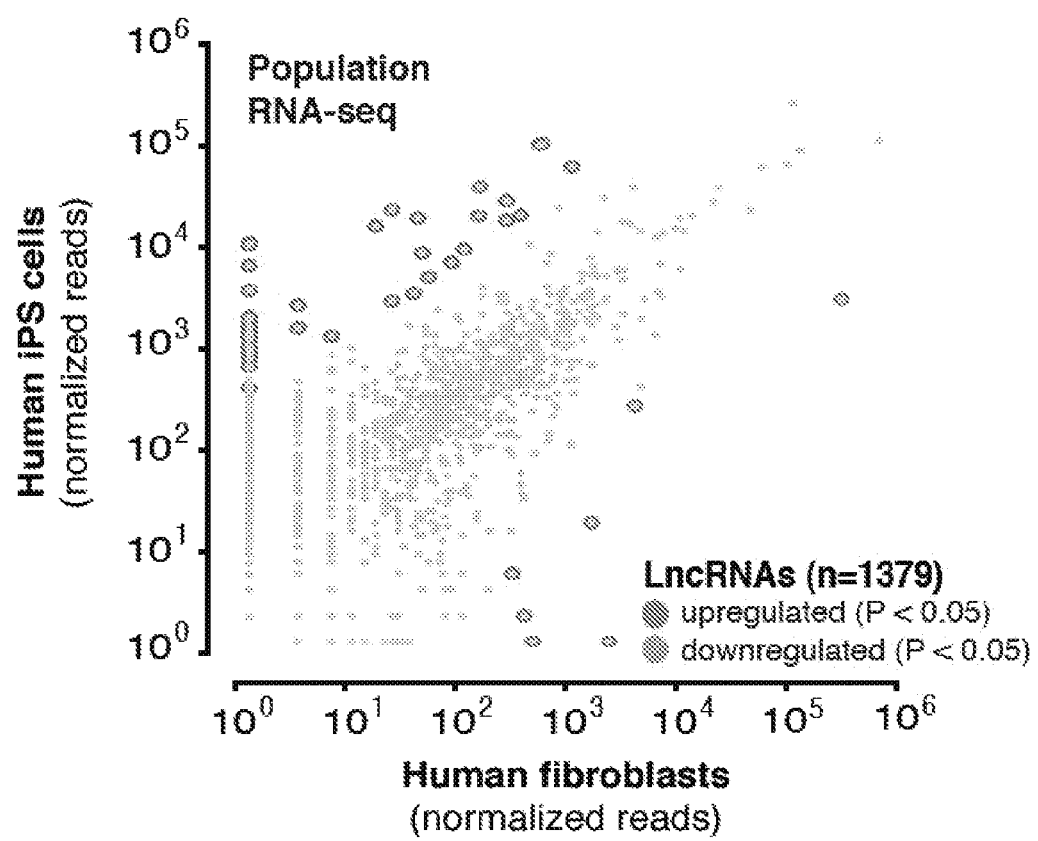
FIG. 23 is a graph showing differential expression analysis of upregulated or downregulated genes in human iPS cells compared to human fibroblasts, as described herein.

FIG. 23 shows a graph of human lncRNAs that are significantly upregulated or downregulated during reprogramming of human primary skin fibroblasts into induced pluripotent stem (IPS) cells. The upregulation or downregulation of genes in the human fibroblasts and the human IPS cells was determined by population RNA-seq (GEO accession #:GSE41716).

Materials and Methods

Example 11 iPS Cell Reprogramming

Tail-tip fibroblast (TTF) cultures were established from 3-8 day old reprogrammable mice homozygous for both the tet-inducible OSKM polycistronic cassette and the ROSA26-M2rtTA allele (Carey, B. W. et al., 2010, supra). Maintenance of animals and tail tip excision were performed according to a mouse protocol approved by the Caltech Institutional Animal Care and Use Committee (IACUC). TTFs (+doxycycline), iPS cells, and ES cells were cultured in ES medium (DMEM, 15% FBS, sodium bicarbonate, HEPES, nonessential amino acids, penicillin-streptomycin, L-glutamine, b-mercaptoethanol, 1000 U/ml LIF) and grown on 6-well plates coated with 0.1% gelatin and irradiated MEF feeder cells (GlobalStem). For "2i" conditions, iPS cells were grown in ESGRO-2i medium (Millipore). For lncRNA loss-of-function, iPS cells were transfected with siRNAs (IDT) using Lipofectamine RNAiMAX (Life). For SSEA-1 detection, StainAlive SSEA-1 DyLight 488 antibody (Stemgent) was used to detect SSEA-1 positive cells at specified time-points during reprogramming, which were isolated using flow cytometry on an iCyt Mission Technology Reflection Cell Sorter inside a Baker Bioguard III biosafety cabinet.

Example 12

Single-Cell and Bulk Sample cDNA Synthesis and Amplification cDNA synthesis was performed using the Smart-Seq protocol as previously described (Ramskold et al., 2012, supra). Specifically, the SMARTer Ultra Low RNA kit for Illumina sequencing (Clontech) was used to generate and amplify cDNA from single cells isolated using a micromanipulator or from bulk samples. Intact single cells were deposited directly into hypotonic lysis buffer. Poly(A)+RNA was reverse transcribed through oligo dT priming to generate full-length cDNA, which was then amplified using 20-22 cycles. cDNA length distribution was assessed using High Sensitivity DNA kits on a Bioanalyzer (Agilent), and only samples showing a broad length distribution peak centered at 2 kb were subsequently used for library generation.

Example 13

Single-Cell and Bulk Sample RNA-Seq Library Generation and Sequencing

Single-cell and bulk sample RNA-seq libraries were constructed using the Nextera DNA Sample Prep kit (Illumina). Briefly, cDNA was 'tagmentated' at 55° C. with Nextera transposase, and tagmented DNA was purified using Agencourt AMPure XP beads (Beckman Coulter). Purified DNA was amplified using 5 cycles of Nextera PCR, and library quality was assessed using High Sensitivity DNA kits on a Bioanalyzer (Agilent). Libraries were sequenced on the Illumina HiSeq2000. Single-end reads of 50 bp or 100 bp length were obtained.

Example 14

Read Mapping and Analysis

All reads were trimmed down to 50 bp (if necessary) and mapped to the mouse genome (version mm9) with TopHat (Trapnell, C. et al., 2009, Bioinformatics 25, 1105-1111, the entire contents of which are herein incorporated by reference) (version 1.2.1) while supplying splice junctions annotated in the ENSEMBL63 set of transcript models. RPKMs for the ENSEMBL63 annotation were obtained using Cufflinks (Trapnell, C. et al., 2010, Nat Biotechnol 28, 511-515, the entire contents of which are herein incorporated by reference) (version 1.0.3) with otherwise default settings. For downstream analysis, the biotype classification of genes and transcripts in the ENSEMBL annotation was used to identify noncoding genes. Hierarchical clustering was carried out using Cluster 3.0 (de Hoon, M. J. et al., 2004, Bioinformatics 20, 1453-1454, the entire contents of which are herein incorporated by reference) and visualized using Java Treeview (Saldanha, A. J., 2004, Bioinformatics 20, 3246-3248, the entire contents of which are herein incorporated by reference). For differential expression analysis, reads were aligned against the refSeq mouse transcriptome using Bowtie version 0.12.7 (Langmead, B. et al., 2009, Genome Biol 10, R25, the entire contents of which are herein incorporated by reference). Expression levels were then estimated using eXpress (Roberts, A. et al., 2013, Nat Methods 10, 71-73, the entire contents of which are herein incorporated by reference) (version 1.3.0), with gene-level effective counts and RPKM values derived from the sum of the corresponding values for all isoforms of a gene. The effective count values were then used as input to DESeq (Anders, S. et al., 2010, Genome Biol 11, R106, the entire contents of which are herein incorporated by reference) to assess differential expression. LncRNA transposon enrichment/depletion analysis was performed as previously described (Kelley, 2012, supra). For ChIP-seq analysis, sequencing data were downloaded from accession numbers GSM307140, GSM623989, GSM307137, GSM307138, E-MTAB-1600, GSM307155, and GSM623991. Reads were extracted using the fastq-dump program in the SRA ToolKit and mapped to the mm9 version of the mouse genome using Bowtie 0.12.7 with the following settings: "-v 2 -k 2 -m 1 -t --best --strata", i.e. retaining only unique reads and allowing for up to 2 mismatches in a read. Enriched regions were called using ERANGE 3.2 (Johnson, D. S. et al., 2007, Science 316, 1497-1502, the entire contents of which are herein incorporated by reference) with the following settings: "-minimum 2 -ratio 3 -shift learn -revbackground".

Example 15

Small RNA Sequencing and Analysis

Oxidation and beta-elimination of small RNAs were performed as previously described (Ameres, S. L. et al., 2010, Science 328, 1534-1539, the entire contents of which are herein incorporated by reference). The Illumina-compatible NEBNext Small RNA Sample Prep Set 1 (New England Biolabs) was used to prepare small RNA libraries for sequencing on the Illumina platform. Sequencing adapters were removed from reads by finding the 3'-most complete match to the adapter sequence and trimming the read after that position. The resulting were first mapped to the collection of ribosomal repeats (annotated using the RepeatMasker file downloaded from the UCSC genome browser), snoRNAs and snRNAs in the mouse genome (version mm9) using Bowtie version 0.12.7 in order to remove common contaminant reads. The unmapped reads from this filtering step were then aligned against the mm9 genome to determine the number of mappable reads. Both bowtie mapping steps were carried out with the following settings: '-v 0 -a -t --best --strata', i.e. no mismatches and an unlimited number of locations to which a read could map to. Enrichment of repeat classes in sequencing was estimated by calculating RPM (Reads Per Million mapped reads) scores for each individual repeat annotated in the UCSC RepeatMasker file, then summing over all the instances of each repeat class in order to derive a total repeat class RPM score.

Example 16

Single-molecule fluorescence in situ hybridization (smFISH)

smFISH was performed as previously described ((Raj et al., 2008, supra). Up to 48 DNA probes per target mRNA or lncRNA were synthesized and conjugated to Alexa fluorophore 488, 555, 594, or 647 (Life Technologies) and then purified by HPLC. Cells were trypsinized, fixed in 4% Formaldehyde, and permeabilized in 70% ethanol overnight. Cells were then hybridized with probe overnight at 30° C., in 20% Formamide, 2×SSC, 0.1 g/ml Dextran Sulfate, 1 mg/ml E. coli tRNA, 2 mM Vanadyl ribonucleoside complex, 0.1% Tween 20 in nuclease free water. Samples were washed twice in 20% Formamide, 2×SSC, and Tween 20 at 30° C., and then twice in 2×SSC+0.1% Tween at RT. 1 µl of hybridized cells was placed between #1 coverslips and flattened. Automated grid-based acquisition was performed on a Nikon Ti-E with Perfect Focus System, Semrock FISH filtersets, Lambda LS Xenona Arc Lamp, 60×1.4 NA oil objective, and Coolsnap HQ2 camera. Semi-automated dot detection and segmentation was performed using custom-built MATLAB software with a Laplacian-of-Gaussian Kernel, using Otsu's method to determine "dotness" threshold across all cells in the dataset.

Example 17

Self-Organizing Maps (SOM)

The 5000 genes with the greatest variance among the libraries were used for training a self-organizing map. Prior to SOM training, the data vectors were normalized on a gene-by-gene basis by subtracting each vector mean and dividing by its standard deviation. The SOM was constructed using the R package 'kohonen.' The total number of map units was set to the heuristic value 5*sqrt(N), where N is the number of data vectors. The map grid was initialized with the first two principal components of the data multiplied by a sinusoidal function to yield smooth toroidal boundary conditions. Training lasted 200 epochs (presentations of the data) during which the radius within which units were adapted toward the winning unit decreased linearly from h/8 to 2 units, where h is the map height (always chosen as the direction of largest length). Further analysis, including clustering and visualization, was performed with custom python code. Clusters were seeded by the local minima of the u-matrix, with a value for each unit defined as the average of the vector difference between that unit's prototype and its six neighbors on the hexagonal grid. All other unit prototypes were then assigned to clusters according to the minimum vector distance to a seed unit. The lists of clustered genes were submitted to the Princeton GO TermFinder (Boyle, E. I. et al., 2004, Bioinformatics 20, 3710-3715, the entire contents of which are herein incorporated by reference) server (http://go.princeton.edu) in order to determine enriched terms.

Example 18 lncRNA Analysis of Induced Pluripotent Stem (iPS) Cells

Raw RNA sequencing data were downloaded from the National Center for Biotechnology Information (NCBI) Gene Expression Omnibus (GEO) and analyzed for differential expression of lncRNAs during mouse hematopoietic progenitor cell (FIG. 21A) and human skin fibroblast (FIG. 23) reprogramming into induced pluripotent stem (iPS) cells. The GEO accession number for FIG. 21A is GSE36290. The GEO accession number for FIG. 23 is GSE41716.

As disclosed throughout and as evidenced by, for example, FIGS. 15A, 15B, 16A-16F, 20A-20C, 21A-21F and 22A, 22B, and Tables 1-4, the disclosed lncRNAs participate in modulating pluripotency reprogramming and pluripotent cell differentiation, and may be utilized to enhance these cell fate methodologies.

While the present invention has been illustrated and described with reference to certain exemplary embodiments, those of ordinary skill in the art will understand that various modifications and changes may be made to the described embodiments without departing from the spirit and scope of the present invention, as defined in the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09441224B1). An electronic copy of the "Sequence Listing" will also be available from the USPTO upon request and payment of the fee set forth in 37 CFR 1.19(b)(3).

What is claimed is:

1. A method of enhancing reprogramming of a somatic cell to a pluripotent cell in a human or mouse, comprising:
    upregulating in the somatic cell at least one long noncoding RNA (lncRNA) selected from SEQ ID NOs. 43, 272, 304, 334, 345, 395, and homologs thereof having at least 85% homology to the at least one lncRNA, the upregulating comprising adding or activating the at least one lncRNA.

2. The method of claim 1, wherein the adding or activating comprises contacting the somatic cell with the at least one synthetic lncRNA and/or a vector encoding the at least one lncRNA.

3. The method of claim 1, further comprising downregulating in the somatic cell at least one lncRNA selected from SEQ ID NOs. 361, 408, 414, 415, 418, 419, and homologs thereof having at least 85% homology to the at least one lncRNA, the downregulating comprising contacting the somatic cell with antisense oligonucleotides and/or interfering RNA (RNAi) targeting the at least one lncRNA.

4. The method of claim 3, wherein the somatic cell is human and the upregulating of the at least one lncRNA comprises upregulating lncRNAs selected from SEQ ID NOs. 334, 345, 395, and the homologs thereof having at least 85% homology to the at least one lncRNA, and the downregulating of the at least one lncRNA comprises contacting the somatic cell with antisense oligonucleotides and/or interfering RNAi targeting the at least one lncRNA selected from SEQ ID NOs. 361, 408, 414, and the homologs thereof having at least 85% homology to the at least one lncRNA.

5. The method of claim 1, further comprising expressing Oct 4, Sox2, Klf4, and c-Myc transcription factors in the somatic cell.

6. The method of claim 1, wherein the homologs have at least 90% homology.

7. A method of enhancing differentiation of a cell in a pluripotent state in a human or mouse, comprising:
    downregulating in the cell at least one long noncoding RNA (lncRNA) selected from SEQ ID NOs. 272, 304, 334, 395, and homologs thereof having at least 85% homology to the at least one lncRNA, the downregulating comprising contacting the cell with antisense oligonucleotides and/or interfering RNA (RNAi) targeting the at least one lncRNA.

8. The method of claim 7, further comprising upregulating at least one lncRNA selected from SEQ ID NOs. 361, 408, 414, 415, 418, 419, and homologs thereof having at least 85% homology to the at least one lncRNA, the upregulating comprising adding or activating the at least one lncRNA.

* * * * *